United States Patent [19]
Rittershaus et al.

[11] Patent Number: 5,426,029
[45] Date of Patent: Jun. 20, 1995

[54] THERAPEUTIC AND DIAGNOSTIC METHODS USING LEUKOCYTE SURFACE ANTIGENS

[75] Inventors: Charles W. Rittershaus, Malden; Wei-Tao Tian, Allston; Patrick C. Kung, Lexington, all of Mass.

[73] Assignee: T Cell Diagnostics, Inc., Woburn, Mass.

[21] Appl. No.: 610,494

[22] Filed: Nov. 7, 1990

Related U.S. Application Data

[63] Continuation-in-part of Ser. No. 434,398, Nov. 9, 1989, Pat. No. 5,292,636, which is a continuation-in-part of Ser. No. 254,551, Oct. 6, 1988, abandoned, which is a continuation-in-part of Ser. No. 20,819, Mar. 2, 1987, Pat. No. 5,006,459, which is a continuation-in-part of Ser. No. 846,230, Mar. 31, 1986, abandoned.

[51] Int. Cl.$^6$ .................. G01N 33/536; G01N 33/543
[52] U.S. Cl. .................. 435/7.21; 435/7.24; 435/7.9; 435/7.94; 436/501; 436/506; 436/518; 436/536
[58] Field of Search .............. 435/5, 7.21, 7.23, 7.24, 435/7.9, 7.94, 961, 974; 436/501, 503, 506, 518, 536, 548, 811, 813

[56] References Cited

U.S. PATENT DOCUMENTS

| | | | |
|---|---|---|---|
| 4,376,110 | 3/1983 | David et al. | 436/513 |
| 4,707,443 | 11/1987 | Nelson et al. | 435/7 |
| 4,810,632 | 3/1989 | McMillan | 435/7.24 |
| 4,845,026 | 7/1989 | Kung et al. | 435/5 |
| 5,006,459 | 4/1991 | Kung et al. | 435/5 |
| 5,059,524 | 10/1991 | McKenzie et al. | 435/7.24 |
| 5,100,777 | 3/1992 | Chang | 435/7.24 |
| 5,168,044 | 12/1992 | Joyce et al. | 435/7.24 |

FOREIGN PATENT DOCUMENTS

| | | |
|---|---|---|
| 8705398 | 9/1987 | WIPO. |
| 8909220 | 10/1989 | WIPO. |
| WO90/04180 | 4/1990 | WIPO. |

OTHER PUBLICATIONS

M. G. Scott et al, *Trends in Biotechnol.*, 3, 170–175, 1985.
S. H. Yoon et al, *Journ. Immunol.*, 134, 3332–3338, 1985.
Berthier et al., "Lymphocyte Surface Molecules in Healthy or HIV Infected Children and Adults" and Capcellia CD4/CD8 Kit for the Immunoassay of CD4/CD8 markers, Diagnostics Pasteur product literature, 1990.
Chem Abstracts, vol. 113 No. 9, 27 Aug. 1990.
(List continued on next page.)

*Primary Examiner*—David Saunders
*Attorney, Agent, or Firm*—Pennie & Edmonds

[57] ABSTRACT

The present invention is directed to the measurement of soluble leukocyte surface markers, soluble T cell growth factor receptors, soluble complement receptors, soluble T cell differentiation antigens, or related soluble molecules or fragments thereof, and the use of such measurements in the diagnosis and therapy of diseases and disorders. The invention is also directed to the measurement of soluble CD35 (sCD35) or fragments thereof, and the use of such measurements in detecting disease or disorders. A polyclonal sandwich assay is provided for the detection and/or measurement of soluble CD35. The invention further relates to the measurement of total leukocyte markers or fragments thereof, and the use of such measurements in the detection and diagnosis of diseases or disorders. The term "total" leukocyte marker used herein refers to the total amount of a leukocyte marker in a sample, including that present in membrane and intracellular compartments and extracellular soluble compartments. Measurements of a total leukocyte marker can be used to determine the approximate amount in a body fluid sample of leukocytes positive for the leukocyte marker. In a further embodiment, the invention relates to the measurement of both the amount of total leukocyte marker and the amount of the soluble form of the leukocyte marker and a comparison of the measured levels.

18 Claims, 12 Drawing Sheets

OTHER PUBLICATIONS

Weisman et al. (1990, Science 249:146-151).
Weis et al. (1987, J. Immunol 138:312-315).
Wong et al. (1985, Proc. Natl. Acad. Sci. U.S.A. 82:7711-7715).
Sim (1985, Biochem. J. 233:883-889).
Dykman et al. (1983, Proc. Natl. Acad. Sci. U.S.A. 80:1698-1702).
Iida et al. (1982, J. Exp. Med. 155:142-1438).
Fearon (1979, Proc. Natl. Acad. Sci. U.S.A. 16:5867-5871).
Kung et al., Science 206:347-349 (1979).
Reinherz et al, Proc. Natl. Acad. Sci. U.S.A. 76:4061-4065 (1979).
Reinherz et al., Proc. Natl. Acad. Sci. U.S.A. 77:1588-1592 (1980).
Verbi et al., Eur. J. Immunol. 12:81-86 (1982).
Kanellopoulos et al., The EMBO J. 2:1807-1814 (1983).
Kung et al., Int. of Dermatol. 22:67-74 (1983).
Krensky and Clayberger, Transplantation 39:339-348 (1985).
McDougal et al., Science 231:382-385 (1986).
Miller et al., Bood 58(1):78-86 (1981).
Falcao et al., J. Clin. Lab. Immunol. 13:141-143 (1984).
Oh et al., Scan. J. Immunol. 22:51-60 (1985).
Acuto et al., Cell 34:717-726 (1983).
Brenner et al., J. Exp. Med. 160:541-551 (1984).
Meuer et al., Proc. Natl. Acad. Sci. U.S.A. 81:1509-1513. (1984a).
Meuer et al., Ann. Rev. Immunol. 2:23-50 (1984b).
McKenzie and Parish, J. Exp. Med. 144:847-851 (1976).
Parish et al., Immunogenetics 3:129-137 (1976).
Parish and McKenzie, Cellular Immunol. 33:134-144 (1977).
Parish et al, Infection and Immunity 26:422-426 (1979).
Wilson et al., J. Immunol. 122:1967-1971 (1979).
Sandrin et al., J.N.C.I. 66:279-283 (1981).
Mier and Gallo, Proc. Natl. Acad. Sci. U.S.A. 77:6134-6138 (1980).
Smith, Immunol. Rev. 51:337-357 (1980).
Arya et al., Science 233:1086-1087 (1984).
Lotze et al., J. Immunol. 135:2865-2875 (1985).
Touw et al., Blood 66:556-561 (1985).
Robb et al., J. Exp. Med. 154:1455-1474 (1981).
Uchiyama et al., J. Immunol. 126:1393-1397 (1981).
Leonard et al., Nature 300:267-269 (1982).
Korsmeyer et al., Proc. Natl. Acad. Sci. U.S.A. 80:4522-4526 (1983).
Depper et al., J. Immunol. 133:1691-1695 (1984).
Sugamura et al., Proc. Natl. Acad. Sci. U.S.A. 81:7441-7445 (1984).
Tsudo et al., J. Expl. Med. 160:612-617 (1984).
Waldman et al., J. Exp. Med. 160:1450-1466 (1984).
Dower et al., J. Exp. Med. 162:501-515 (1985).
Ebert et al., Clin Immunol. and Immunopathol. 37:283-297 (1985).
Rubin et al., Hybridoma 4:91-102 (1985).
Uchiyama et al., J. Clin. Invest. 76:446-453 (1985).
Greene and Leonard, Ann. Rev. Immunol. 4:69-95 (1986).
Gupta, Clin. Immunol. and Immunopathol. 38:93-100 (1986).
Mutsuoka et al., Leukemia Res. 10:597-603 (1986).
Tsudo et al., Blood 67:316-321 (1986).
Tuow et al., Blood 68:1088-1094 (1986).
Chilosi, et al., Int. J. Biological Markers 2:101-104 (1986).
Durno et al., Blood 68 Suppl. #1,124a (1986).
John et al., Sixth Int. Cong. Immunol. Toronto, Canada (1986).
Keller et al., Am. Diabetes Assoc. (1986).
Nelson et al., Pediatric Res. 20:136-139 (1986).
Pizzolo et al., Blood 68 Suppl. #1, 228a (1986).
Reuben et al., Blood 68 Suppl. #1, 213a (1986).
Rubin et al., J. Immunol. 137:3841-3844 (1986).
Saadeh et al., Fed. Proc. 45:378 (1986).
Treiger et al., J. Immunol. 136:4099-4105 (1986).
van Es et al., Transplantation 37:65-69 (1984).
Austen and Cosimi, N. Engl. J. Med. 311:1436-1438 (1984).
Hancock et al., Transplantation 39:430-438 (1985).
Magrath et al., Blood 63:1102-1111 (1984).
Pui et al., Blood 66:778-782 (1985).
Murphy et al., J. Clin. Oncol. 4:1732-1739 (1986).
Arseneau et al., Am.J.Med. 58:314-321.
Gay et al., Nature 328:626-629, (1987).
Dagleish et al., Immunol. Today 7:142-143 (1986).
Sattentau et al., Cell 52:631-633, (1988).
Fisher et al., Nature 331:76-78, (1988).
Germain et al., Cell 54:441-444, (1988).
Weiss et al., Nature 331:15, (1988).
Siliciano et al., Cell 54:561-575, (1988).
Hussey et al., Nature 331:78-81, (1988).
Maddon et al., Cell 42:93-104, (1985).
Littman et al., Nature 325:453-455, (1987).
Traunecker et al., Nature 331:84-86, (1987).
Smith et al., Science 238:1704-1707, (1987).

(List continued on next page.)

OTHER PUBLICATIONS

Maddon et al., PCT International Publication No. WO88/01304 published Feb. 25, 1988.
Deen et al., Nature 331:82–84, (1988).
Doyle et al., Nature 330: 256–259, (1987).
Booth et al., News & Comment, Science 239:341–343, (1988).
Meuer et al., Proc. Natl. Acad Sci USA 79:4395–4399, (1982).
Biddison et al., J. Exp. Med. 159:783, (1984).
Hoxie et al., J. Immunol, 137:1194–1201, (1986).
Snow et al., J. Biol. Chem. 258:14675–14681, (1983).
Doumerc et al., 1986 6th Intl. Congress of Immunology, Toronto, Ontario, Canada, Jul. 1986, Abstr. 5.54.6, p. 768.
Kung et al., Clin. Chem. 34:1340 (1988).
Swain et al., Proc. Natl. Acad. Sci. U.S.A. 78:7101–7105 (1981).
Francus et al., J. Immunol. 140:1823–1829 (1988).
Greene et al., Ann. Intern. Med. 105:560–572 (1986).
Rubin et al., in Leukocytes and Host Defense, Oppenheim, J. J., and D. M. Jacobs, eds., Alan R. Liss, Inc., New York, pp. 95–120, (1986).
Yasuda et al., Blood 71:1021–1026 (1988).
Steis et al., Blood 71:1304–1309 (1988).
Pui et al., Blood 71:1135–1137 (1988).
Wolf et al., Arth. Rheum. 31:729–735 (1988).
Stolc et al., Diag. Clin. Immunol. 5:171–174 (1987).
Tomkinson et al., J. Immunol. 139:3802–3807 (1987).
Rubin et al., vol. 104 No. 21, p. 489 abstract No. 184611, (May 26, 1986).
Cerretti et al., EP-A-0 162 699, Immunex Corp., (1985).
Nelson et al., EP-A-O 202 975 (The United States of America), (1986).
Rubin et al., (1985), Federation Proceedings, 69th Annual Mtg., Anaheim Calif., vol. 44, No. 4, Apr. 21–26. 1985, Abstract 3131, pp. 946, Mar. 5, 1985.
Fujimoto et al., J. Exp. Med. 160:116–124, Jul. 1984.
Snow et al., The Journal of Biological Chemistry 260:2700–2708 (1985).
Snow et al., The Journal of Immunology 135:3172–3177, (Nov. 1985).
Rubin et al., The Journal of Immunology 135:3172–3177, Nov. 1985.
Rubin et al., Clin Research, vol. 33, No. 2, p. 388A, (Apr. 1986).
Osawa et al., Eur. J. Immunol., :467–469, (1986).
Nelson et al., Journal of Clinical Immunology 6:114–120, (1986).
Bayer et al., DT, A, 3628718, (Jun. 4, 1987).
Nelson et al., U.S. Patent No. 4,707,443, (1987).
Kung et al.., WO A, 8705912, PCT, (Oct. 8, 1987).
Mackeen et al., Fed. Proc., 45:457, Ab. No. 1746, (1986).
Nelson et al., Fed. Proc., vol. 45, No. 3, Abs. 1294, Mar. 1, 1986.
Rubin et al., Clin. Res., 33, 457A, Apr. 1986.
Saadeh et al., Fed. Proc., vol. 45, No. 3, Abs. 1298 (1986).
De Moyos et al., FASEB Abstract Form Received at Society Office by Tuesday, Dec. 8, 1987.
Rao et al., Cell Immunol. 80:310, (1983).
Knowles et al., USA, 4,645,738, (Feb. 24, 1987).
Baldwin et al., Monoclonal Antibodies for Cancer Detection and Therapy, p. 20, Karl Erik Hellstrom and Hellstron, (1985).
Litman et al., U.S. patent No. 4,391,904, (Jul. 5, 1983).
Litman et al., U.S. patent No. 4,299,916, (Nov. 10, 1981).
David et al., U.S. patent No. 4,376,110 (Mar. 8, 1983).
Ruppert, et al. "IL–4 Decreases the Expression of the Monocyte Differentiation Marker CD14, Paralleled by an Increasing Accessory Potency", Immunobiol. 182:449–464 (1991).
Prince, et al. "Depressed Interleukin 2 Receptor Expression in Acquired Immune Deficiency and Lymphadenopathy Syndromes", J. Immunol. 133:1313–1317 (1984).
Robbins, et al., "Immune Recognition of HLA Molecules Downmodulates CD8 Expression on Cytotoxic T Lymphocytes", J. Exp. Med. 173:221–230 (1991).
Endl et al., "A New ELISA–Based Assay for Quantitation of Human T-Lymphocyte Subpopulations", J. Immunol. Meth. 102:77–83 (1987).
Hessian, et al., "Development of an Enzyme Immunoassay for the Quantitation of Cellular Antigen Expression:, J. Immunol. Meth. 91:29–34 (1986).
Morris, et al., "Cellular Enzyme–Linked Immunospecific Assay (CELISA)—A New Micromethod that Detects Antibodies to Cell-Surface Antigens", Human Immunol. 5:1–19 (1982).

THERAPEUTIC AND DIAGNOSTIC METHODS USING LEUKOCYTE SURFACE ANTIGENS

This application is a continuation-in-part of application Ser. No. 07/434,398, filed on Nov. 9, 1989 and now Pat. No. 5,292,636, which is a continuation-in-part of application Ser. No. 07/254,551, filed on Oct. 6, 1988 and now abandoned, which is a continuation-in-part of application Ser. No. 07/020,819, filed on Mar. 2, 1987 and now Pat. No. 5,006,459, which is a continuation-in-part of application Ser. No. 06/846,230, filed on Mar. 31, 1986 and now abandoned.

INTRODUCTION

The present invention is directed to the measurement of soluble leukocyte surface molecules, such as soluble T cell growth factor receptors, complement receptors and T cell differentiation antigens or fragments thereof, and the application of such measurements in the diagnosis and therapy of diseases and disorders. The present invention is also directed to the measurement of total leukocyte molecules, such as T cell receptors and T cell differentiation antigens or fragments thereof, and the application of such measurements in the diagnosis and therapy of diseases and disorders. The measurement of such molecules, and preferably a plurality of such molecules, can be used in monitoring the effect of a therapeutic treatment, detecting and/or staging disease or in differential diagnosis of a physiological condition.

BACKGROUND OF THE INVENTION

2.1. LEUKOCYTE SURFACE MOLECULES

Clusters of differentiation (CD) have been established which define human leukocyte differentiation of antigens (Bernard and Boumsell, 1984, Hum. Immunol. 11:1-10; Knapp et al., 1989, Immunol. Today 10:253:258; Gebel et al., 1988, ASHI Quarterly 12:11; Leukocyte Typing III: White Cell Differentiation Antigens. Ed., McMichael, A. J. 1987. Oxford University Press. Oxford), by the comparison of reactivities of monoclonal antibodies directed against the differentiation antigens. The T cell surface antigens, their classification into epitope-defined subgroups, and their distributions on T cells have been studied by use of monoclonal antibodies directed against human T cells (Clark et al., 1983, Immunogenetics 18:599-615; Hansen et al., 1984, in Leucocyte Typing, Bernard, A., et al., eds., Springer-Verlag, New York, pp. 195-212). Some of the T cell clusters of differentiation and other T cell surface molecules are listed in Table I.

These T cell surface markers serve as markers of the cell lineage, the identity of the functional T cell subset to which the T cell belongs, and the activation state of the T cell. Several of the cell surface molecules have been studied in great detail, have been found to be important in initiating and regulating immune functions and are critical to communication processes between immune cells.

TABLE I

LEUKOCYTE SURFACE MOLECULES

| Leukocyte Surface Marker | Expression | Detection Monoclonal Antibodies | References |
|---|---|---|---|
| T cell Antigen Receptor | All T cells and T cell subsets | T40/25, αF1, βF1, δTCS1 TCRδ1, CγM1 | 1, 2, 3, 4, 5, 6 |
| CD1 | Thymocytes & Langerhans Cells, Leukemia Cells | OKT6 NAI/34 | |
| NK cell receptor | NK cells | NC-37 specific antibodies | 7 |
| Cell Adhesion Molecules | | | |
| CD2 | All T cells | OKT11 Leu5 B67.1 | 8, 9, 10 |
| CD58 (LFA-3) | Leukocytes, epithelial | TS2/9 | 11 |
| CD3 | Pan T cell | OKT3 Leu4 | 12 |
| CD4 | Helper/Inducer Subsets of T cells | OKT4 Leu3a | 12 |
| CD5 | T. B subsets | UCHT2 T1 | 11 |
| CD7 | T Cells | 3AI | 11 |
| CD8 | Supressor/Cytotoxic Subsets of T cells | α Chain: OKT8 Leu2a | 13, 14 |
| | | β Chain: T8/2T8 | 14a |
| β2 integrins | | | |
| LeuCAM | leukocyte cell adhesion molecules | | 11 |
| CD11a (LFA-1) | myeloid, lymphoid | | 11.15 |
| CD11b (MAC-1 (CR3)) | myeloid | | 11, 15, 16, 17, 18, 19 |
| CD11c (CR4) | myeloid | | 11, 15 |
| CD16 (FcR111) | Natural Killer, Macrophages Granulocytes | HUNK2 3G8 | 11 |
| CD21 (CR2) | B subset | B2 HB5 | 11, 20 |
| CD23(FCεR11) | B subset | MHM6 Blast-2 | 11 |
| CD25 | TAC, IL-2 Receptor (Activated T Cells) | Anti-TAC 7G7/B6 | 21 |
| CD30 | Activated T, B Cells Reed-Steinberg Cells | Ki-1 HSR4 | 11 |
| CD35(CR1) | Granulocytes, B cells, | YZ-1 | 11, 22 |

TABLE I-continued

LEUKOCYTE SURFACE MOLECULES

| Leukocyte Surface Marker | Expression | Detection Monoclonal Antibodies | References |
|---|---|---|---|
| | monocytes | J3D3 | |
| β3 integrins | | | |
| CD41 | | | 11, 23 |
| CD51 | | | 11, 23 |
| Homing Receptors | | | |
| CD44 | Leukocytes, brain | 33-3B3 | 24 |
| Mel-14 | | GRHL1 | 25, 26 |
| β1 Integrins | | | |
| CD49a-f(VLA-1, VLA-2, VLA-3, VLA-4, VLA-5, VLA-6) | Extracellular Matrix (ECM) | | 27, 23 |
| CD56(NKH1, NCAM) | Natural Killer Activated lymphocytes | NKH1 Leu19 | 11 |
| CD71 | Transferrin Receptor, Proliferating cells | | 11, 28 |

List of References for Table I

1. Brenner et al., 1984, J. Exp. Med. 160:541–551.
2. Henry et al., 1989, Hybridoma, 8:577.
3. Brenner et al., 1987, J. Immunol., 138:1502.
4. Wu et al., 1988, J. Immunol., 141:1476.
5. Band et al., 1987, Science 238:682.
6. Hochstenbach et al., 1988, J. Exp. Med. 168:761.
7. Evans, International patent publications #WO89/03394, #WO88/03395, & #WO88/03396 published Apr. 20, 1989
8. Bierer et al., 1989, Annu. Rev. Immunol. 7:579-99.
9. Verbi et al., 1982, Eur. J. Immunol. 12:81–86.
10. Perussia et al., 1983, J. Immunol. 133:180.
11. Knapp et al., 1989, Immunol. Today 10:253.
12. Kung et al., 1979, Science 206:347–349.
13. Reinherz et al., 1979, Proc. Natl. Acad Sci. USA 76:4061–4065.
14. Ledbetter et al., 1981, Monoclonal Antibodies and T cell Hybridoma, Elsevier, North Holland, N.Y. pp 16–22.
14a. Shieu, L., et al., 1988, J. Exp. Med. 168(6):1993-2005.
15. Kishimoto et al., 1989, Adv. Immunol. 46:149–182.
16. Altieri & Edgington, 1988, J. Biol. Chem 263:7007-15.
17. Wright et al., 1988, Proc. Natl. Acad. Sci. USA 85:7734–38.
18. Wright et al., 1989, J. Exp. Med. 169:175–83.
19. Russell & Wright, 1988, J. Exp. Med. 168:279–92.
20. Nemerow et al., 1985, J. Virol. 55:347–351.
21. Uchiyawa et al., 1981, J. Immunol. 126(4):1393–1397.
22. Klickstein et al., J. Exp. Med. 165:1095–1112.
23. Hemler, 1990, Annu. Rev. Immunol. 8:365–400.
24. Berg et al., 1989, Immunol. Rev. 108:1–18.
25. Lasky et al., 1989, Cell 56:1045–55.
26. Haynes et al., 1989, Immunol. Today 10:423.
27. Hynes, 1987, Cell 48:549.
28. Reinherz et al., 1980, Proc. Natl. Acad. Sci. USA, 77:1588–1592.

2.1.1. T CELL ANTIGEN RECEPTOR COMPLEX

T cell antigen receptor, a surface molecule which comprises a disulfide-linker dimer of approximately 90 kilodaltons (kd), recognizes specific antigens and is responsible for initiating a complex series of biochemical events which constitute the T cell activation process (Meuer, S. C., et al., 1984, Ann. Rev. Immunol. 2:23–50; Acuto, O. et al., 1983, Cell 34:717–726).

T cell antigen receptors (TCR) are remarkably similar to B cell antigen receptors, which are cell surface immunoglobulins (Igs). Both Igs and TCRs are glycoproteins, and both create an antigen binding site from the association of two different protein chains: heavy and light chains for Igs, and $\alpha$ and $\beta$ or $\gamma$ and $\delta$ chains for TCR so Both Igs and TCRs also share some of the genetic mechanisms which create the diversity of antigen binding sites necessary to recognize all potential antigens. In the case of T cells, recombination events at the genomic level produce a mature mRNA for a complete e TCR chain by combining discrete gene segments for the variable (V), joining (J), and constant (C) regions of the protein. Similarly, mRNA coding for the $\beta$ TCR chain protein is constructed using V, J, C, gene segments plus an additional gene segment termed diversity (D). Currently in humans, the $V\alpha$ pool of gene segments is estimated to contain approximately 100 members and the $V\beta$ pool approximately 70 members which can be assembled with D, J, and C gene segments. The number of permutations created in mature $\alpha$ and $\beta$ chains by these events, and the association of the different $\alpha$ and $\beta$ chains into mature heterodimers leads to a huge number of potential TCRs, each with a unique antigen specificity. For $\gamma\delta$ TCRs, the story is much the same, except the pool of $V\gamma$ and $V\delta$ gene segments is smaller.

Based on similarities at the nucleic acid level, the $V\beta$ pool of gene segments has been grouped into 18 "families." Likewise, the $V\alpha$ pool of gene segments has been grouped into 19 "families" (Klein et al, 1987, Proc. Natl. Acad. Sci. USA 84:6884–6888; Toyonaga et al., 1987, Ann. Rev. Immunol. 5:585–620). Each family can contain between 1 and 10 members.

The human $\gamma\delta$ TCR occurs in three biochemically distinct forms. A 40 kd TCR-$\gamma$ chain is disulfide linked to the TCR-$\delta$ chain in one form, whereas 40 kd or 55 kd TCR-$\gamma$ polypeptides are non-covalently associated with the TCR-$\delta$ chains in the other two forms. Sequential analyses of TCR-$\gamma$ cDNA clones indicate that the first form utilizes the C$\gamma$1 gene segment while the other two forms appear to use allelic C$\gamma$2 gene segments. The C$\gamma$1 and the two allelic C$\gamma$2 gene segments differ primarily in the sequence and number of copies of the constant region exon. This region encodes the peptide segment connecting the transmembrane and the extracellular, Ig-like domain (Band et al., 1989, J. Immunol. 142:3627). The human γδ TCR is found on 0-8% of peripheral blood lymphocytes from most normal individuals. The percentage of T cells bearing the γδ TCR may vary significantly in tissues of lymphoid origin, as well as in lymphoid malignancies (Groh et al., 1989, J. Exp. Med. 169:1277).

The T cell antigen receptor exists in a complex with at least three other proteins, known as the CD3 complex. Immunoprecipitation with anti-CD3 antibodies using non-ionic detergents has revealed three proteins (γ, δ, ε) of the CD3 complex as well as a clonotypic heterodimer that has been shown to be the α and β chains or γ and δ chains of the T cell antigen receptor (Kannellopoulos, J. M., et al., 1983, EMBO J. 2:1807; Borst, J., et al., 1983, Eur. J. Immunol. 13:576; Van Den Elsen, P, et al., 1984, Nature 312:413; Meuer, S. C., et al., 1983, J. Exp. Med. 157:705).

2.1.2. T CELL GROWTH FACTORS & RECEPTORS

T cells secrete a variety of polypeptides affecting immunoregulation of hematopoietic cells and are themselves subject to regulation by hormone peptides interacting with specific receptors on their cell surface. Interleukin-2 (IL-2), originally termed T cell growth factor, is synthesized and secreted by antigen- or lectin-activated T lymphocytes in the presence of macrophage-derived interleukin-1 and must interact with specific high-affinity membrane receptors to exert its biological effects (Smith, K. A., 1980, Immunol. Rev. 51:337–357; Leonard, W. J., et al., 1983, Proc. Natl. Acad. Sci. U.S.A. 80:6957–6961).

Lymphokine receptors, e.g. interleukin 2 (IL-2) receptor and interleukin 1 (IL-1) receptor, are essential for the activation and proliferation of T cells (Smith, K. A. 1984, Ann. Rev. Immunol. 2:319–333; Dower, S. K., et al., 1985, J. Exp. Med. 162:501–515).

The interleukin-2 receptor (IL-2R, Tac antigen) is not present on the surface of resting T or B lymphocytes. Upon activation by specific antigens or mitogens, T cell proliferation is mediated by an autocrine mechanism whereby activated cells secrete IL-2 and also express cell surface receptors for IL-2 (IL-2R) (Leonard, W. J., et al., 1982, Nature 300:267; Meuer, S. C., et al., 1984, Proc. Natl. Acad. Sci. U.S.A. 81:1509). In addition to T cells, B cells (Mingari, M. C., et al., 1984, Nature 312:641-3; Pike, B. L. et al., 1984, Proc. Natl. Acad. Sci. U.S.A. 81:7917-21; Saiki, O., et al., 1988, J. Immunol. 140:853-8), NK cells (Ortaldo, J. R., et al., 1984, J. Immunol. 133:779–83; Kehrl, J. H., et al., 1988, J. Clin. Invest. 81:200-5) and possibly monocytes (Herrmann, F., et al., 1985, J. Immunol. 162:1111-6; Holter W., et al., 1986, J. Immunol. 136:2171-75) express a membrane-bound IL-2R.

The high affinity IL2R that functions to signal T cell cycle progression is composed of two distinct polypeptides chains, each of which contains an IL-2 binding site (Teshigawara, K., et alo, 1987, J. Exp. Med 165:223). The larger IL-2 binding protein (75 kD molecular weight) is designated as the beta chain, whereas the smaller protein (55 kD molecular weight) is termed the alpha chain (Smith, K. A., 1988, Adv. Immunol. 42:165–78). The alpha chain was the first IL-2 binding protein to become recognized as an "activation antigen" on the surface of activated T cells (hence the name anti-Tac for "T activated") (Uchiyama, T., et al., 1981, J. Immunol. 126:1393-7).

Most T cells do not express the high affinity IL-2 receptor or the p75 chain without prior activation. NK (natural killer) cells appear to constitutively express the intermediate affinity p75 IL-2 receptor (Caligiuri et al., 1990, J. Exp. Med. 171:1509-26).

Interaction of IL-2 with its cell surface receptor results in a continuous T cell proliferation (Greene, W. C. and Leonard, W. J., 1986, Ann. Rev. Immunol. 4:69-95; Smith, K. A., 1984, Ann. Rev. Immunol. 2:319-333). Measurement of IL2R provides information on the state of immune activation of the lymphoid population. This has been accomplished by measuring IL2R on cell surfaces using flow cytometry or fluorescence microscopy. Using monoclonal antibodies which define the IL-2 receptor, altered IL-2 receptor expression has been reported in a number of immune abnormalities (Greene and Leonard, supra; Depper, J. M., et al., 1984, J. Immunol. 133:1691–1695). Membrane IL2R has been found on certain B- or T-cell malignancies including Burkitt's lymphoma (Waldmann, T. A., et al., 1984, J. Exp. Med. 160:1450–1466), hairy cell leukemia (Waldmann et al., supra; Korsmeyer, S. J., et al., 1983, Proc. Natl. Acad. Sci. U.S.A. 80:4522-4526), and human T cell leukemia virus (HTLV) -I-associated adult T cell leukemia (Depper, J. M., et al., 1984, J. Immunol. 133:1691–1695). The function of cellular IL2R in lymphoid malignancies has not been fully elucidated. Several cases of common, pre-B or T cell acute lymphoblastic leukemia (ALL) have been induced to express IL2R after in vitro activation (Touw, I., et al., 1985, Blood 66:556-561, Touw, I., et al., 1986, Blood 68:1088-1094; Matsuoka, M., et al., 1986, Leuk. Res. 10:597-603) and, in some cases, interleukin 2 stimulated subsequent colony formation of neoplastic progenitor cells in vitro (Touw, 1985 supra; Touw, 1986, supra).

Leukemia cells from some patients with T cell chronic lymphocytic leukemia were shown to have the receptors and a good proliferative response to exogenous interleukin 2 (Uchiyama, T., et al., 1985, J. Clin. Invest. 76:446–453; Tsudo, M., 1986, Blood 67:316–321). However, HTLV-1 associated adult T cell leukemia constitutively expressed high levels of cell surface IL2R but had no or very poor proliferative responses to interleukin 2 (Uchiyama, 1985, supra; Arya, S. K., et al., 1984, Science 223:1086-1087). Ebert et al., (1985, Clin. Immunol. Immunopath. 37:283–297) have reported that T cells from patients with AIDS virus lack the ability to express IL2R on their surface even when the cell is activated.

Utilizing immunohistochemical staining, Kurnick reported high numbers of IL2R and HLA-DR positive cells in lung tumor infiltrating lymphocytes (Kurnick, J. T., et al., 1986, Clin. Immunol. Immunopath. 38:367–380).

2.1.3. CD ANTIGENS

CD8 (OKT8 antigen) is a T cell specific surface glycoprotein expressed on the surface of approximately 30% of T lymphocytes associated with suppression and cytotoxic functions and the ability to recognize antigen in the context of class I MHC antigens (Swain, S. L., 1983, Immunol. Rev. 74:129–42). CD8 cells have been shown to be able to control HIV-1 infection in vitro (Walker et al., 1986, Science 234:1563–66). Homology between CD4 and CD8 is quite low. CD8 exists on the cell surface as dimeric or multimeric structures composed of a 33KD monomer (Snow, P. M., et al., 1983, J. Biol. Chem 258:14675–14681).

CD56 is a pan-NK antigen that is expressed on cultured T cells and neuroectodermal cells. CD56 was previously designated NKH1 antigen which was an isoform of the neural cellular adhesion molecule, N-CAM. CD30 is a glycoprotein selectively expressed on subpopulations of activated T and B cells and in Reed-Steinberg cells. CD23, the Fce R11 receptor, is present on B cell subsets; activated macrophages and eosinophils. CD23 has been produced as a soluble recombinant form that may be useful for treatment of IgE induced allergic reactions (European Patent Publication #EP324879 published Jul. 26, 1989). CD16 is the FcR111 receptor and is a marker for natural killer cells, granulocytes and monocytes. CD7 is a T cell specific antigen that may be useful for immunophenotyping lymphomas (Haynes et al., 1989. Immunol. Today 10:87–91). CD44 is involved in cell attachment to extracellular matrix components or specific cell surface ligands. It has been produced as a recombinant soluble CD44-immunoglobulin fusion protein which was used to demonstrate that CD44 is the principal cell surface receptor for hyaluronate (Aruffo et al., 1990, Cell 61:1303–1313).

CD4 (OKT4 antigen) is a 55 kd glycoprotein expressed on the surface of approximately 60% of all T lymphocytes. It is found primarily on T cells associated with helper/inducer regulatory functions (Reinherz et al., 1979, Proc. Natl. Acad. Sci. USA 76:4061–4065), and to a lesser degree, on cells of the monocyte/macrophage population. It serves as a signal to activate B cells, and induces CD8+ T cells to become cytotoxic/suppressor cells. CD4+. cytotoxic/suppressor cells are also known to exist. Recent research suggests that CD4 can be further defined based on its ability to recognize antigen in the context of type II major histocompatibility complex (MHC), (Swain, 1983, Immunol. Rev. 74:129–142; Meuer et alo, 1982, Proc. Natl. Acad. Sci. U.S.A. 79:4395-99; Dagleish, 1986, Immunol. Today 7:142; Sattentau & Weiss, 1988, Cell 52:631–33). CD4 may play a role as an adhesion molecule, binding the non-polymorphic region of the class II (MHC) and anchoring the MHC II/T cell receptor complex. Beyond acting as a stabilizing force, it is speculated that CD4 may function to transduce signals across the T cell membrane (Gay, et al., 1987, Nature 328:626–29).

The cloning of the gene encoding CD4 reveals that it, like CDS, is a member of the immunoglobulin supergene family, containing both amino acid (32%) and structural ($\beta$ sheets held together by disulfide bridges) homology at the V (variable)-like domain of CD4 to the V region of immunoglobulin (Maddon, P. J. et al., 1985, Cell 42:93–104). This V-like region of the molecule is followed by a stretch of 263 amino acids with no known homology to other molecules, followed by a transmembrane domain and highly charged cytoplasmic tail, containing serines which are phosphorylated upon activation (Littman, D. R., et al., 1984, Nature 325:453–55).

It has been established that the CD4 molecule is the cell surface receptor for HIV-1 (McDougal et al., 1986, Science 231:382–385) and much current research is focused on elucidation of its role in AIDS. Recombinant soluble CD4 has been shown to block HIV infection in vitro, (Fisher et al., 1988, Nature, 331:77; Weiss, 1988, Nature 331:15). Currently, clinical trials of recombinant CD4 treatments in AIDS patients are underway to test whether rCD4 might inhibit HIV-1 infection by binding gp120, an outer envelope protein of the virus. It is postulated that free gp 120 mediates its toxic effect in at least two ways:

a) by gaining entry into the thymus where it binds to CD4+ thymocytes, creating subsets of CD4+ cells which are "non-immune"; and, b) by inducing HIV-1 directed cytotoxic T cells to kill un-infected CD4+ T cells expressing Class II molecules (Germain, 1988, Cell 54:441–44). Following the circulating levels of CD4+ cells is key among the various prognostic indicators for evaluating progression of AIDS (Fahey, et al., 1990, N. Engl. J. Med., 322:3; ibid, pp. 166–72).

2.1.4. COMPLEMENT RECEPTORS

CR1 (CD35) is the receptor for C3b and C4b and can inhibit the C3/C5 convertases of the classical and alternative complement pathways. It can also act as a cofactor for the cleavage of C3b and C4b by factor I. CD35 is a glycoprotein comprising multiple short consensus repeats (SCRs) arranged in 4 long homologous repeats (LHRs). The C-terminal LHR, called LHR-D, is followed by 2 additional SCRs, a transmembrane region consisting of a hydrophobic stretch of amino acids, and a hydrophilic stretch of amino acids forming the cytoplasmic region (Klickstein et al., 1987, J. Exp. Med., 165:1095; Klickstein et al). Erythrocyte CD35 appears to be involved in the removal of circulating immune complex in autoimmune patients, and its levels may correlate with the development of AIDS (Inada et al., 1986, AIDS Res. 2:235; Inada et al., 1989, Ann. Rheu. Dis. 4:287). Solid phase assay methods for detecting human C3b receptor have been disclosed (U.S. Pat. No. 4,672,044, dated Jun. 9, 1987).

CR2 (CD21) is also a transmembrane glycoprotein with an extracellular domain of 15–16 SCRs, a transmembrane region and a cytoplasmic domain (Weiss et al., 1988, J. Exp. Med., 167:1047–1066; Moore et al., 1987, Proc. Natl. Acad. Sci. 84:9194). CR2 is the B cell receptor for Epstein Barr Virus as well as a complement pathway receptor.

Complement receptor CR3 binds iC3b which results in adhesion of cells during inflammation (Marks et al., 1989, Nature 339:314). CR4 (CD11) also appears to be involved in leukocyte adhesion (Kishimoto et al., 1989, Adv. Immunol. 46:149–82).

A recombinant soluble form of CD35 has been produced which is able to inhibit activation of both the classical and alternative pathways in vitro. It also can suppress complement activation in vivo and is effective in animal models of inflammation and reperfusion injury associated with myocardial infarction (International Patent Application number PCT/US89/01358, published Oct. 5, 1989 as WO89/09220 and entitled "The Human C3b/C4b Receptor (CD35)"; Weissman et al., 1990, Science 249:146-151). A form of recombinant soluble CR2 has been produced by the deletion of transmembrane and cytoplasmic domains. It is reported to bind C3$\delta\gamma$ at low levels (Moore et al., 1989, J. Biol. Chem. 264:20576).

2.1.5. ADHESION MOLECULES AND HOMING RECEPTORS

There are multiple receptor systems involved in leukocyte adhesion. These include (1) homing receptors (CD44, Haynes et al., 1989, Immunol. Today, 10:423-8; Picker et al., 1989, J. Immunol. 142:2046–2051) involved in tissue specific migration and recirculation of lymphocytes, (2) cell-cell interaction molecules (CD2, LFA-3) that augment antigen-specific interactions, (3) β 82 integrin molecules (LeuCAMs) involved in leukocyte cell-cell interactions, and (4) receptors for extracellular matrix (ECM) interactions (β1 integrins) involved in leukocyte differentiation, inflammation, and tissue localization. Complement receptors, CR3 and CR4, are members of the β integrin subfamily and are involved in leukocyte adhesion (Hemler, 1990, Ann. Rev. Immunol. 8:365–400; Hynes, 1987, Cell 48:549–54; Wright et al., 1988, Proc. Natl. Acad. Sci. USA 85:7734-38; Detmers et al., 1988, J. Cell Biol. 105:1137-45; Hermanowski-Vosatka et al., 1988, J. Biol. Chem. 263:17822-27).

2.1.6. LEUKOCYTE SURFACE MOLECULE SPECIFIC ANTIBODIES

Over the last several years, antibodies to determinants of murine and human TCRs have been developed. Some of these antibodies appear to recognize all members of a V region family, some a subset of V regions within a family, and some a particular V region only (TABLE II).

TABLE II

These TCR antibodies identify minor populations of peripheral blood T cells (1–5%) and subdivide T cells in a new way based on TCR V region usage.

| Name | Clone | Specificity | Immunogen | Reactivity | Reference* |
|------|-------|-------------|-----------|------------|------------|
| βV5(a) | 1C1 | Vβ5.2 and Vβ5.3 Subfamilies | HPB | 1-5% of PBL | 1 |
| βV5(b) | W112 | Vβ5.3 Subfamily subset of βV5(a) | HPB | 0-3% of PBL | 2 |
| βV8(a) | 16G8 | Vβ8 family | JURKAT | 1-5% of PBL | 2 |
| βV12(a) | S511 | Vβ12 family | SEZARY | 1-5% of PBL | 3 |
| βV6(a) | OT145 | Vβ6 family Allotypic Vβ6.7 epitope | T-CLL | 0-5% of PBL | 4 |
| αV2(a) | F1 | Vα2 Subfamily | T-CLL | 1-5% of PBL | 5 |
| αβV(a) | LC4 | Vβ5.1 Subfamily | SUP-T13 | 1-5% of PBL | 6 |

List of References for Table II

1. Boylston et al., 1986, J. Immunol. 137:741–744.
2. Tian et al., 1989, FASEB J. 3:A486 Abstr.
3. Bigler et al., 1983, J. Exp. Med. 158:1000–1005.
4. Posnett et al., 1986, Proc. Natl. Acad. Sci. U.S.A. 83:7888–7892.
5. Janson et al., 1989, Canc. Immunol. Immunother. 28:225–232.
6. Maecker & Levy, 1989, 1989 J. Immunol. 142:1395–1404.

These reagents have proven valuable in studying the repertoire of TCRs expressed under many in vivo and in vitro conditions. For example, in vitro stimulation of mononuclear cells with certain bacterial enterotoxins (superantigens) leads to the expansion of T cells expressing a limited number of TCR Vβ families (Kappler et al., 1989, Science 244:811–813). In vivo expansion of T cells bearing particular Vβ regions has been detected in certain animal models of autoimmune diseases, and manipulation of these cells with anti-V region specific monoclonal antibodies has modified and reversed disease progression. Murine experimental encephalomyelitis (EAE), a model of autoimmune disease, is characterized by the expansion of T cell populations expressing Vβ8 TCRs. Administration of monoclonal antibodies specific for murine Vβ8 TCRs reversed established clinical EAE (Acha-Orbea et al., 1988, Cell 54:263–273; Urban et al., 1988, Cell 54:577–592). In humans, analysis of TCR receptor usage is just beginning, yet evidence is mounting in autoimmune disorders that TCR V region usage may be disease related (Wraith et al., 1989, Cell 57:709–715). Elevated levels of T cells bearing selected Vβ's or Vα's have been reported in Crohn's disease (Vβ8), sarcoidosis, cutaneous T cell lymphoma, multiple sclerosis (Vβ 12, Vβ 17, Vα 8, Vα 10, Vα 12), Uveal melanoma (Vα7) and melanoma (Vα) (Moller et al., 1988, J. Clin. Invest. 82:1183–1191; Posnett et al., 1990, J. Clin. Invest. 85:1770; Schmelkin et al., 1989, Gastroenterology 96:A449 Abst; Jack et al., 1990, Amer. J. Patho. 136:17–21; Wucherpfennig et al., 1990, Science 248:1016; Okensburg et al., 1990, Nature 345:344; Nitta et al., 1990, Science 249:672, Kumer in Lotze and Finn, Immunol. Today 11:190, 1990).

Other antibodies recognize common determinants on all αβ or γδ TCRs. These include CγM1, a monoclonal antibody which has been shown to specifically recognize the TCR-γ protein (Hochstenbach et al., 1988, J. Exp. Med. 168:761). This monoclonal antibody was generated against a constant-region encoded peptide and reacts with both Cγ1 and Cγ2 encoded TCR-γ chains. It appears to possess framework reactivity against all TCR-γ polypeptides.

TCRδ1 (Band et al., 1987, Science 238:682) and δ TCS1 (Wu et al., 1988, J. Immunol. 141:1476) are monoclonal antibodies specific for the δ chain of the human γδ TCR. Unlike clone specific or idiotypic anti-TCR antibodies, TCRδ1 appears to identify all T cells which express the γδ TCR. δ TCS1 identifies a minor subset of these γδ T cells.

Additional monoclonal antibodies to the T cell receptor gamma and delta chains have also been reported (European Patent Publication #EP289252 Published Nov. 2, 1988; International Patent Publication #WO88/00209 published Jan. 14, 1988).

βFI (Brenner et al., 1987, J. Immunol. 138:1502–1509) is a murine monoclonal antibody specific for a framework, i.e., common or nonpolymorphic determinant on the β chain of the αβ TCR and identifies all T cells expressing the αβ TCR. αF1 (Henry et al., 1989, Hybridoma 8:577) is a monoclonal antibody specific for a framework determinant of the α chain and identifies all T cells expressing the αβ TCR.

Antibodies to CD4 have been widely described (Kung, P. C., et al., 1979, Science 206:347–349) and are commercially available. A series of such antibodies reacting with non-competing epitopes on the CD4 molecule have been described. Such a set has been termed OKT4, OKT4A, OKT4B, OKT4C, OKT4D, OKT4E, and OKT4(Rao, P. E., et al., 1983, Cell. Immunol. 80:310).

Antibodies directed against the CD4 or CD8 antigens have been shown to block cell function. Antibodies against CD4 block most helper T functions, mixed lymphocyte reactions and induction of T helper activity (Biddison et al., 1984, J. Exp. Med. 159:783). Antibodies against CD8 block the cytotoxic activity of CD8 positive cytotoxic T lymphocytes (Swain, S. L., 1981, Proc. Natl. Acad. Sci. U.S.A. 78:7101-7105). Antibodies against CD4 have also been described that are capable of activating CD4-positive T cells. CD4 is internalized upon treatment of the cells with phorbol esters and resulting phosphorylation (Hoxie, J. A., et al., 1986, J. Immunol. 137:1194-1201).

Numerous antibodies to adhesion molecules and other leukocyte surface receptors have been described (Hemler, 1990, Ann. Rev. Immunol. 8:365-400; Hynes, 1987, Cell 48:549-54; Haynes et al., 1989, Immunol. Today 10:423-8; Knapp et al., 1989, Immunol. Today 10:253-8). Complement receptor antibodies to CR2 (Nemerou et al., 1989, J. Virol. 55:347; European Patent Application #EP358130 published Mar. 14, 1990) are able to block binding of EBV. Antibodies to CD35 (Wong et al., 1985, J. Immunol. Methods 82:303; Yoon & Fearon, 1985, 134:3332; Schrieber, U.S. Pat. No. 4,672,044 issued Jun. 9, 1987), CR3 (International Patent Publication #WO 89/04174 published May 18, 1989), CD56, CD30, CD16 and CD23 (Knapp et al., 1989, Immunol. Today 10:253-8) have also been reported.

Homing receptor specific antibodies have been shown to inhibit the binding of leukocytes to endothelial cells or to block leukocyte homing to synovium (Butcher & Jalkanen, European Patent Publication #EP 303463, Published Feb. 15, 1989). Interleukin 2 receptor antibodies may be therapeutically useful (International Patent Publication Number WO89/09622 published Oct. 19, 1986; European Patent Publication #EP241811 published Oct. 21, 1987; International Patent Publication #WO88/09671 published Dec. 15, 1988). Antibodies to the interleukin 1 receptor may be obtained by using the protein expressed from the cloned gene (European Patent #EP318296 published May 31, 1989).

2.1.7. CLINICAL APPLICATIONS

These various lymphocyte cell surface markers have enormous clinical application potentials for the identification of lymphocyte populations and their functional status (Krensky, A. M. and Clayberger, C., 1985, Transplant. 39 (4) :339-348; Kung, P. C., et al., 1984, Monoclonal Antibodies in Clinical Investigations, Clinical Biochemistry-Contemporary Theories and Techniques, Vol. 3, Academic Press, pp. 89-115; Kung, P. C., et al., 1983, Int. J. Dermatol. 22 (2): 67-733; Cosimi et al., 1981, N. Engl. J. of Med. 305: 308; Knowles et al., 1983, Diagnostic Immunol. 1:142; Hoffman, 1984, Amer. Biotechnol. Lab 2:39).

Existing clinical methods of T cell typing involve the use of monoclonal antibodies which define T cell surface markers to detect the presence of specific cell surface markers on the T cell surface. Measuring the total numbers of T cells expressing a marker on the surface or membrane has been useful for the characterization and classification of lymphoid malignancies (Greaves, M., et al., 1981, Int. J. Immunopharmac. 3 (3) :283-300). Changes in the relative percentage of T helper and T suppressor/cytotoxic cells were found to be associated with immune events in renal transplantation due to viral infection (Colvin, R. B., et al., 1981, Proc. 8th Int. Congr. Nephrol., Athens, pp. 990-996), autoimmune diseases (Veys, E. M., et al., 1981, Int. J. Immunopharmac. 3(3):313-319), and AIDS (Gupta, S., 1986, Clin. Immunol. Immunopathal. 38:93-100; Ebert, E. C., et al., 1985, Clin. Immunol. Immunopathol. 37-283-297).

The expression of T cell surface markers has also been used for the assessment of the immune status of patients. It has been established that by measuring the relative number of distinct, functional T cell subsets, and/or the relative number of activated T cells in peripheral blood or tissues, an assessment of the immunological condition of a patient is possible. The activation antigens (e.g. IL-2 receptor) appear to be involved in T cell growth and differentiation processes.

2.2. SPONTANEOUSLY RELEASED SOLUBLE IMMUNE CELL SURFACE MOLECULES sHLA

Several immune cell surface markers have been detected in the serum. The molecules of the human major histocompatibility complex (HLA molecules) are sets of cell surface glycoproteins involved in immune recognition. These macromolecular antigens have also been found to be present in body fluids such as serum (Pellegrino, M. A., et al., 1984, Meth. Enzymol. 108:614-624). The serum levels of class I HLA-A and HLA-B have been shown to be present in sufficient quantity to perform HLA-typing in sera (Russo, C., et al., 1983, Transplant. Proc. 15(1):66-68; Pellegrino, M. A., et al., 1981, Transplant. Proc. 13(4):1935-1938). The presence of Class II HLA-DR in serum has also been detected (Sandrin, M. S., et al., 1981, J. Natl. Cancer Inst. 66(2):279-283; Russo, C., et al., 1983, Transplant. Proc. 15(1):57-59). The serum HLA-DR (Ia) has been shown to be markedly depressed in tumor patients.

SIL-2R

A soluble form of IL2R has been detected (Rubin et al., 1985, J. Immunol. 135:3172-3177; Rubin et al., 1985, Fed Proc. 44:946; U.S. Pat. No. 4,707,443 by Nelson et al.) that is released by activated normal peripheral blood mononuclear cells and synthesized in large amounts in vitro by HTLV-I-infected leukemic cell lines. A sandwich enzyme immunoassay was used to quantitate the soluble IL2R.

Little is known about the functional significance of soluble IL2R. Since soluble IL2R is capable of binding interleukin 2 (Rubin, L. A., et al., 1985, J. Immunol. 135:3172-3177), it may have an immunoregulatory role by competing with cellular IL2R for the ligand and thus down-regulating the immune response. In this regard, the soluble IL2R has been suggested to be a "blocking factor" produced by the malignant cells to inhibit the host's immune response to the tumor (id.).

Subsequent studies have disclosed comparable levels of soluble IL2R in cord blood and peripheral blood from normal adults (Nelson, D. L., et alo, 1986, Pediatr. Res. 20:136-139). Increased serum levels of IL2R have been found in patients with certain B or T cell malignancies (Nelson, D. C., 1986, Fed. Proc. 45:377; Saadeh, C., et al., 1986, Fed. Proc. 45:378; MacKeen, L., et al., 1986, Fed. Proc. 45:454; Reuben, J. M., et al., 1986, Blood 68(5), Supp. 1:213a). Elevated levels of soluble IL2R have also been reported present in the serum of aged subjects (Saadeh, C., et al., 1986, Fed. Proc. 45:378), and in patients with AIDS (Saadeh, supra).

Soluble CD Antigens

Several other cell surface markers which are primarily present on T cells have also been found in soluble form. CD2, a T cell surface molecule present in all normal T cells and a receptor for sheep red blood cells, has been detected at higher levels in the sera of certain cancer patients than those found in normal control patients (Falcao, R. P., et al., 1984, Clin. Lab. Immunol. 13:141-143; Oh, S. K., et al., 1985, Scand. J. Immunol. 22:51-60). CD8 (Leu 2, OKT8), a surface marker found on the surface of suppressor/cytotoxic T cells and which may be involved in cellular recognition, has also been reported at highly elevated levels in the serum of patients with T cell leukemia (Fujimoto, J., et al., 1983, J. Exp. Med. 159:752-766). Leu-1, another T cell surface molecule, was measured in serum following anti-Leu-1 monoclonal antibody treatment (Miller, R. A., et al., 1982, New Engl. J. of Med. 306:517-520). Oh et al. (1985, supra) reported that less than half of the patients with malignancies in their study presented elevated levels of soluble CD2 receptor in their serum.

A soluble form of CD35 has been detected in human plasma (Yoon & Fearon, 1985, J. Immunol. 134:3332) from normal individuals and in patients with systemic lupus erythematosus (SLE). It is reported to be functionally active and structurally similar to intact CD35 on membranes. Soluble CD30 has been found in sera from patients with Hodgkin's disease (Gause et al., 1990, ASCO Proceedings, ASCO Annual Meeting, Washington, D.C., Abst.), lymphoma, adult T cell leukemia, infectious mononucleosis (Pfreundschuh et al., 1990, Int. J. Cancer, Vol 45), and malignant lymphoma (Josimovic-Alasevic et al., 1989, Eur. J. Immunol. 19:157-162). Soluble CD44 has been shown to circulate in serum (Dalchau et al., 1980, Eur. J. Immunol. 10:745; Telen et al., 1983, 1983, J. Clin. Invest. 71:1978; Haynes et al., 1989, Springer Semino Immunopathol. 11:163-185). CD23 is the low affinity receptor that is normally found in a membrane bound form on B cells. It is found in a soluble form in various pathological conditions such as bone marrow transplantation (Bengtsson et al., 1989, Blood 73:2139-2144; Knoller et al., 1989, Immunol. 66:368-375; Pene et al., 1989, J. Cell. Biochem. 39:253-264; Pfeil et al., 1989, Immunol. 68:37-44; Billaud et al., 1989, J. Virol. 63:4121-4128; Sarfati & Delepesse, 1988, J. Immunol. 141:2195-2199).

However, not all T cell surface molecules are released into the serum (Fujimoto, J., et al., 1983, J. Exp. Med. 159:752-766). Leu 1 antigen was not detectable in the serum of normal or leukemic patients who have not received antibody therapy. Leu 3 antigens were also not detectable in soluble form in T cell culture supernatants (id.).

Fujimoto et al. (1983, J. Exp. Med. 159:752-766) were unable to find evidence of released CD4 using a sandwich enzyme immunoassay based on Leu3b and Leu3a (Becton-Dickinson). This assay worked well with detergent lysates of cells but did not detect released CD4 in culture supernatants of CD4+ and CD8+ leukemic T cells which could be shown to release CD8, or in culture supernatants of CD4+ T cells.

sTCR

Coassigned, U.S. Pat. No. 4,845,026 issued Jul. 4, 1989, entitled "Assay Systems for Detecting Cell Free T Cell Antigen Receptor Related Molecules and Clinical Utilities of the Assays" concerns methods for diagnosing diseases and for monitoring diseased conditions by measuring the amount of soluble T cell antigen receptor in a subject's body fluid.

2.3. DISEASES AND DISORDERS INVOLVING COMPLEMENT

The complement activation pathways play a fundamental role in many human diseases and disorders. Some complement mediated diseases and disorders are discused infra.

Autoimmune Disease

Diminished expression of CD35 on erythrocytes of patients with SLE has been reported by investigators from several geographic regions, including Japan, the United States, and Europe. Taken as a group, patients have an average number of receptors per cell that is 50-60% that of normal populations, although there is considerable overlap because of the genetically determined marked variation in this characteristic among normal individuals.

An early report noted that CD35 number on erythrocytes varied inversely with disease activity, with lowest numbers occurring during periods of most severe manifestations of SLE, and higher numbers being observed during periods of remission in the same patient (Inada, et al, 1982, Clin. Exp. Immunol. 50:189-197; Tayler et al., 1983; Arthritis Rheum, 26:736-44).

Recently acquired loss of erythrocyte CD35 in the setting of active SLE and hemolytic anemia was demonstrated by observing the rapid loss of the receptor from transfused erythrocytes (Walport et al., 1987, Clin. Exp. Immunol. 69:501-7).

Immune complexes are found in many pathological states including but not limited to autoimmune diseases such as rheumatoid arthritis or SLE, hematologic malignancies such as AIDS (Tayler et al., 1983, Arthritis Rheum. 26:736-44; Inada et al., 1986, AIDS Research 2:235-247) and disorders involving autoantibodies and/or complement activation (Ross et al., 1985, J. Immunol. 135:2005-14).

Erythrocyte CD35 is reported to have a functional role in the removal of circulating immune complexes in autoimmune patients and may thereby inhibit the deposition of immune complexes within body tissue constituents (Inada et al., 1989, Ann. Rheum. Dis. 4:287). Additional findings suggest detrimental loss of CD35 activity progressing from asymptomatic seropositive homosexual volunteers to the prodromal spectrum of ARC and finally progressing to a total disappearance in overt AIDS (Inada et al., 1986, AIDS Res. 2:235).

Hemodialysis

In vitro studies have demonstrated that CD35 can be elicited from the intracellular vesicular compartment to the plasma membrane within seconds following stimulation of neutrophils with chemotactic peptides, such as C5a and formylmethionylleucylphenylalanine, certain cytokines and endotoxin. In studies of patients undergoing hemodialysis for chronic renal failure in whom there was a three-to five- fold increase in the amount of CD35 at the cell surface of neutrophils taken during dialysis with membranes that activated complement but not with non-complement activating membranes.

The use of a hemodialyzer also activates the alternative pathway. Levels of Bb, iC3b, C3a and C5a increase, but C4d levels do not change (Oppermann et al., 1988, Klin. Wochenscher 66:857-864; Kojima et al., 1989; Nippon Jenzo Gakkai Shi 31:91-97; Ueda et al., 1990, Nippon Jenzo Gakkai Shi 32:19-24). Terminal complement complex was demonstrated in the plasma (Kojima et al., 1989, supra), and on the membranes of granulocytes during dialysis (Deppisch et al., 1990, Kidney. Int. 37:696–706).

Cardiopulmonary Bypass

Elevated C3a has been demonstrated in patients undergoing prolonged extra corporeal circulation (Chenoweth et al., 1981, Complement 3:152–165). Increased plasma levels of SC5b-9 (Dalmasso et al., 1981, Complement Inflamm. 6:36–48), and terminal C5b-9 complex deposits on erythrocytes and polymorphonuclear cells (Salama et al., 1988, N. Engl. J. Med. 318:408–414) have been observed in these patients.

Several lines of evidence showed that the complement system in cardiopulmonary bypass is activated primarily via the alternative pathway: (1) C3a level was increased, but not C4a, suggesting that alternative pathway was predominantly responsible (Cavarocchi et al., 1986, Circulation 74: III 130–133; Chenoweth et al., 1986. Complement 3:152–165). However, protamine sulfate (a heparin antagonist) administration after cardiopulmonary bypass activated the classical pathway (Chenoweth et al., 1986, supra; Kirklin et al., 1986, Ann. Thorac. Surg. 41:193–199; Weiler et al., 1990, J. Allergy. Clin. Immunol. Methods, 108:77–84) showed that although C3a des arg was generated, C1-C1-inhibitor complexes, an indicative of classical pathway activation, did not increase.

Two types of oxygenators (bubble and membrane) have been used for cardiopulmonary bypass. The bubble oxygenator generated more C3a production than the membrance oxygenator (Cavarocchi et al., 1986, J. Thorac. Cardiovasc. Surg. 91:252–258). In an experimental model, the dogs which had bubble oxygenator developed higher risk of infection with *Staphylococcus aureus* than those with the membrane oxygenator, suggesting the decreased complement levels may impair the host defense during cardiopulmonary bypass (van Oeveren et al., 1987 Ann. Thorac. Surg. 44:523–528).

Thermal Injury (burn)

It has been shown that massive activation of the alternative complement pathway, but not the classical pathway, was observed in a model of burn injury in mice; cobra venom factor (CVF) pretreatment reduced burn mortality (Gelfand et al., 1982, J. Clin. Invest. 70:1170–1176). Elevations of plasma C3a des Arg and C4a des Arg were also detected in burn patients (Davis et al., 1987, Surgery 102:477–484).

Activated C3 was detected in plasma of a guinea pig model of thermal injury (Bjornson et al., 1986, J. Infect. Dis. 153:1098-1107). Complement-depletion diminished the generation of C5a (Oldham et al., 1988, Surgery 104:272-279) and burn edema (Friedl et al., 1989, Am. J. Pathol. 135:203-217) in a rat cutaneous burn model. In another rat model, complement depletion also attenuated the systemic hemodynamics depression (Schirmer et al., 1989, J. Trauma 29:932–938). Furthermore, it has been suggested that neutrophil sequestration occurs very early in a sheep thermal injury animal model, probably as a result of oxidant initiated complement activation (Demling et al., 1989, Surgery 106:52–59).

Neutrophil activation was also demonstrated in patients with thermal injury whose neutrophils have increased expression of CD35 for up to three weeks following the initial burn, and in whom infectious disease complications, such as sepsis or pneumonia, were associated with transient, further increases in CD35 expression by neutrophils.

Adult Respiratory Distress Syndrome (ARDS)

ARDS is a fulminant form of respiratory failure affecting many critically ill patients. It has been reported that in the first 48 hours, complement activation occurred via the alternative pathway only and was later followed by activation via the classical pathway (Zilow et al., 1990, Clin. Exp. Immunol 79:151–157). Clr Cls-Cl inhibitor complex, C3b-P complex (Langlois et al., 1989, Heart Lung 18:71–84), and terminal complement complex (Langlois et al., 1988, Am. Rev. Respir. Dis. 138:368–375) were suggested to be useful to distinguish patients with ARDS from those without ARDS. Moreover, the amounts of C3a and C5a in patients with respiratory failure correlated with the severity of the eventual pulmonary insult (Weigelt et al., 1988, J. Trauma 28:1013–1019).

Decomplementation with cobra venom factor (CVF) in an animal model of ARDS protected against lung injury (Guice et al., 1989, Ann. Surg. 210:740–747). Similarly, complement-depletion by CVF in a porcine model produced by infusion of live *Pseudomonas aeruginosa* developed less septic acute respiratory disease (Dehring et al., 1987, J. Trauma 27:615–625). When cynomolgus monkeys (Macaca fascicularis) were made acutely septic with infusions of E. coli, severe sepsis and ARDS resulted (Stevens et al., 1986, J. Clin. Invest. 77:1812–1816). Three major early events occurred: generation of C5a, decrease in peripheral leukocyte counts, and increase in the sequestration of leukocytes in the lungs (Hangen et al., 1990, J. Surg. Res. 48:196–203). In this model, ARDS was prevented with a rabbit anti-human polyclonal antibody to C5a des arg (Stevens et al., 1986, supra); the C3a and C4a levels were elevated, but not C5a (Hangen et al., 1989, J. Surg. Res. 46:195–199). This antibody was also shown to be able to inhibit polymorphonuclear chemotaxis and reduce the release of lysosomal enzymes (Hatherill et al., 1989, J. Biol. Response Mod. 8:614–624).

Sepsis

Activation of the complement system via the classical pathway is suggested to be involved in the development of fatal complications in sepsis (Hack et al., 1989, Am. J. Med. 86:20–26).

Barotrauma

It has been hypothesized that the phenomena of decompression sickness (DCS) are mediated by complement. The complement system is activated in rabbits with DCS. When these rabbits were pharmacologically decomplementing in vivo, they did not develop DCS (Ward et al., 1990, Undersea Biomed. Res. 17:51–66).

It has been demonstrated that a recombinant produced soluble complement receptor type I (sCD35) functions as an in vivo inhibitor of complement and acts to suppress post-ischemic myocardial inflammation and necrosis (Weisman et al., 1990, Science, 340:146–151).

SUMMARY OF THE INVENTION

The present invention is directed to the measurement of soluble leukocyte surface markers, soluble T cell growth factor receptors, soluble complement receptors, soluble T cell differentiation antigens, or related soluble molecules or fragments thereof, and the use of such measurements in the diagnosis and therapy of diseases and disorders. The measurement of such molecules can be valuable in monitoring the effect of a therapeutic treatment on a subject, detecting and/or staging a disease in a subject, and in differential diagnosis of a physiological condition in a subject. These measurements can also aid in predicting therapeutic outcome and in evaluating and monitoring the immune status of patients.

The invention is also directed to immunoassays which preferentially detect soluble CD4 (sCD4) over the cell-surface CD4.

An increase in soluble CD4 antigen levels in a sample from a patient can be used to diagnose a state of immune activation. Such an increase in soluble CD4 antigen levels in synovial fluid can be used to diagnose rheumatoid arthritis. Soluble CD4 measurements can also be used to stage adult T cell leukemia, or determine the phenotype of a cell in culture. Soluble CD4 measurements can also be used to monitor AIDS patients undergoing therapy.

The invention is also directed to the measurement of soluble CD35 (sCD35) or fragments thereof, and the use of such measurements in detecting disease or disorders. A polyclonal sandwich assay is provided for the detection and/or measurement of soluble CD35. The measurement of soluble CD35 may also be valuable in monitoring the effect of a therapeutic treatment on a subject, in predicting therapeutic outcome and in evaluating and monitoring the immune status of patients. Monitoring soluble CD35 levels may be especially useful in disorders associated with inappropriate complement activation, including but not limited to AIDS and diseases characterized by inflammation and immune complex disorders.

The invention also relates to the measurement of a plurality of soluble leukocyte surface markers for the detection, staging, or monitoring of a disease or disorder. In particular embodiments, the measurement of a plurality of soluble T cell surface markers and their change relative to one another can be superior to the measurement of any soluble T cell surface marker alone, for the detecting, staging, or monitoring of treatment of a disease or disorder.

In particular embodiments, measurements of the soluble T cell surface molecules can be accomplished by sandwich enzyme immunoassays.

The invention further relates to the measurement of total leukocyte markers or fragments thereof, and the use of such measurements in the detection and diagnosis of diseases or disorders. The term "total" leukocyte marker used herein refers to the total amount of a leukocyte marker in a sample, including that present in membrane and intracellular compartments and extracellular soluble compartments. Measurements of total leukocyte markers can be used to determine the approximate amount in a body fluid sample of leukocytes positive for the leukocyte marker. Measurements of total leukocyte markers are useful in monitoring the effectiveness of a treatment on a subject, in predicting therapeutic outcome or disease prognosis, and in evaluating and monitoring the immune status of patients. Measurements of total leukocyte surface molecules can be accomplished by sandwich enzyme immunoassays where the samples are treated so that the total amount of a leukocyte marker present in membrane, intracytoplasmic and/or soluble compartments can be measured.

In particular embodiments, the invention concerns the measurement of amounts of total CD4. Total CD4 measurements are particularly useful in diseases where the absolute number of CD4+ cells is the best indicator of disease prognosis or treatment outcome. Such diseases include, but are not limited to, AIDS.

In another embodiment, the invention concerns the measurement of the total amount of CD8. Total CD8 measurements are especially useful in diseases associated with modulation of the CD8+ subset of leukocytes. These include but are not limited to infectious diseases.

In yet another embodiment, the invention relates to the measurement of the total amount of T cell antigen receptor present in a sample. Total TCR measurements can include the measurement of total TCR on all cells expressing any $\alpha\beta$ or $\gamma\delta$ TCR or can include the measurement of total TCR on particular subsets of cells including, but not limited to, subsets expressing specific V$\alpha$, V$\beta$, V$\delta$ and/or V$\gamma$ peptides.

In a further embodiment, the invention relates to the measurement of both the amount of total leukocyte marker and the amount of the same soluble leukocyte marker and a comparison of the measured levels. The change in the total levels and soluble levels relative to one another during disease progression or disease treatment can be superior to the measurement of either total or soluble levels alone, for the detection, diagnosis or monitoring of treatment of a disease or disorder.

In a specific embodiment, the change in the level of a total marker or of a soluble marker can be more sensitive than the absolute level of the total marker or of the soluble marker at any one time in the detecting, diagnosing or monitoring of treatment of a disease or disorder.

In other embodiments, the levels of total marker can be measured in samples obtained from body fluids, including but not limited to whole blood, synovial fluid, spinal fluid, pleural effusions, tumor and tissue infiltrates.

3.1. DEFINITIONS

As used herein, the following terms will have the meanings indicated:

| | |
|---|---|
| Total Marker = | the total amount of a marker (including membrane-associated, intra- and extracellular) present in a sample. |
| Staging a disease = | determining the degree of severity of a disease |
| AZT = | azido-deoxythymidine |
| B-cell ALL = | B-cell acute lymphoblastic leukemia |
| CsA = | cyclosporin A |
| HTLV III/LAV/HIV = | Human T cell Leukemia Virus Type I/Lymphadenopathy Associated Virus/Human Immunodeficiency Virus |
| OPD = | O-phenylenediamine |
| IL-1 = | interleukin-1 |
| IL-2 = | interleukin-2 |
| IL2R = | interleukin-2 receptor |
| mAb = | monoclonal antibody |
| NHL = | non-Hodgkin's lymphoma |
| PBMC = | peripheral blood mononuclear cell |
| PHA = | phytohemagglutinin |
| RF = | rheumatoid factor |
| Spontaneous release = | release by normal or pathologic physiological processes of the cell |
| AIDS = | Acquired immunodeficiency disease syndrome |
| CD35 = | Complement receptor 1 |
| TCR = | T cell antigen receptor. |

DETAILED DESCRIPTION OF THE INVENTION

Figure 1:
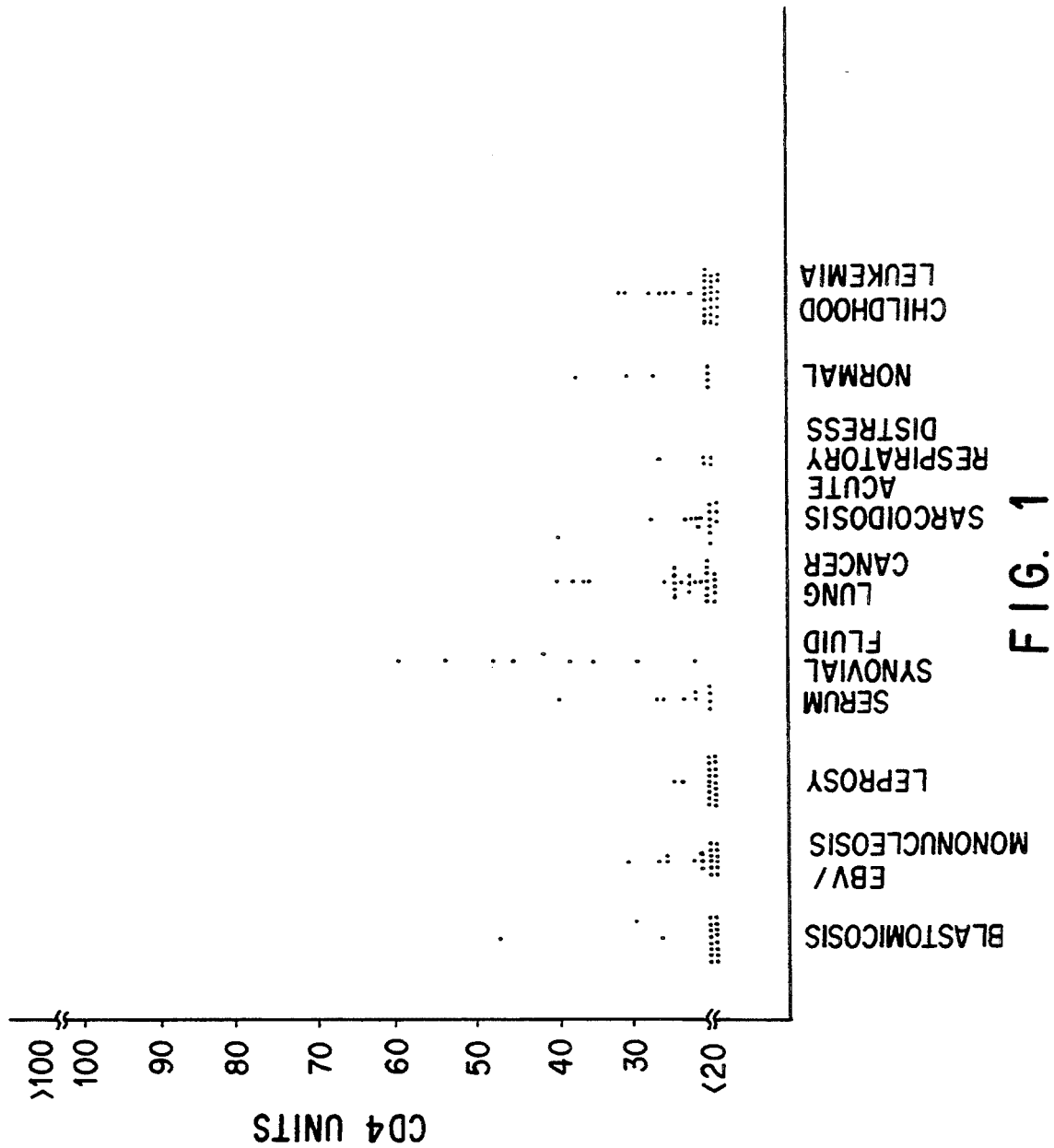
FIG. 1. Levels of soluble CD4 in sera of normal individuals and patients from a number of disease groups. The assay used was as described in Section 6.1.2.1, infra. CD4 antigen was detected using mAb 8F4 as capture reagent and mAb R2B7 as detection reagent in a sandwich immunoassay. The limit of sensitivity for the assay was 20 units.

The present invention is directed to the measurement of soluble leukocyte surface markers, soluble T cell growth factor receptors, soluble complement receptors, soluble T cell differentiation antigens, or related soluble molecules or fragments thereof, and the use of such measurements in the diagnosis and therapy of diseases and disorders.

As used herein, the term "soluble" shall mean those molecules that are "spontaneously released"; i.e., released by normal or pathologic physiological processes of the cell, and those molecules present in soluble form in a body fluid by virtue of their in vivo administration to the patient. Such molecules are to be distinguished from "solubilized" cell surface forms of the molecules, whose solubilization is brought about by in vitro manipulation such as cell lysis by detergent. The soluble leukocyte cell markers (antigens and receptors) of the invention are molecules which carry antigenic determinants of their cell-surface counterparts.

Proteinaceous molecules, or fragments thereof, derived from the surface of leukocytes, and proteinaceous molecules which have immunologically similar counterparts present on the surface of leukocytes or activated leukocytes, which are present in a body fluid and not associated with the surface of a cell are soluble leukocyte molecules of the invention. These molecules can be either glycosylated or nonglycosylated and may be soluble by themselves or considered soluble by virtue of their association with other soluble molecules.

The measurement of the soluble molecules of the invention can be valuable in monitoring the effect of a therapeutic treatment on a subject, detecting and/or staging a disease in a subject and in differential diagnosis of the physiological condition of a subject. These measurements can also aid in predicting therapeutic outcome and in evaluating and monitoring the immune status of patients. More than one type of soluble molecule can be measured. The soluble molecules can be measured in any body fluid of the subject including but not limited to serum, plasma, urine, saliva, pleural effusions, synovial fluid, spinal fluid, tissue infiltrations and tumor infiltrates.

The present invention is also directed to the measurement of total leukocyte surface markers, total T cell growth factor receptors, total complement receptors, total T cell differentiation antigens, or related total markers or fragments thereof, and the use of such measurements in the diagnosis and therapy of diseases and disorders.

As used herein, the term "Total" shall mean the total amount of the marker present in the sample. For example, in a particular sample such as a sample that comprises whole blood, the total marker includes the amount of marker present in the membrane, intracytoplasmic and soluble compartments of the sample. The soluble compartment can include both spontaneously released soluble marker as well as soluble recombinant markers that may have been administered as a therapeutic treatment. In another sample such as in a sample that comprises cells, the total marker includes the amount of marker present in the membrane, intracytoplasmic and cell culture media compartments of the sample. Total marker can include the amount of marker present in any one compartment or in any combination of compartments depending upon the nature of the sample. The markers of the invention are molecules (antigens and receptors) or fragments thereof, which carry antigenic determinants detected by specific antibodies.

The measurement of total markers according to the invention can be valuable in monitoring the effect of a therapeutic treatment on a subject, detecting and/or staging a disease in a subject, in predicting therapeutic outcome or disease prognosis and in evaluating and monitoring immune status of patients. A plurality of total markers can be measured. Total markers can be measured in many body fluids including, but not limited to whole blood, synovial fluid, spinal fluid, saliva, pleural effusions, tumor and tissue infiltrates.

Any of numerous immunoassays can be used in the practice of the instant invention, such as those described in Section 5.6.1, infra. Antibodies, or antibody fragments containing the binding domain, which can be employed include but are not limited to suitable antibodies among those in Section 2.1.6 supra and other antibodies known in the art or which can be obtained by procedures standard in the art such as those described in Section 5.6.2 infra.

5.1. MONITORING THE EFFECT OF A THERAPEUTIC TREATMENT

The present invention provides a method for monitoring the effect of a therapeutic treatment on a subject who has undergone the therapeutic treatment. This method comprises measuring at suitable time intervals the amount of a soluble molecule or soluble fragment thereof, or the amount of a total marker or fragment thereof, either of which comprises, or is immunologically related to, a leukocyte growth factor receptor, leukocyte surface molecule, complement receptor or T cell differentiation antigen. Any change or absence of change in the amount of the soluble molecule or in the amount of the total marker can be identified and correlated with the effect of the treatment on the subject. In a specific embodiment of the invention, soluble molecules immunologically related to CD35 can be measured in the serum of patients by a sandwich enzyme immunoassay (for an example, see Section 16, infra) in order to predict disease prognosis, for example, in AIDS, or to monitor the effectiveness of treatments such as AZT administration. Soluble CD35 may itself be used as a therapeutic treatment, and the course of therapy may be followed by detecting soluble CD35 (see section 5.6.4, infra). In another embodiment, soluble molecules related to the interleukin-1 receptor can be measured. In yet another embodiment, soluble molecules immunologically related to the CD4 antigen can be measured. In particular, the levels of soluble CD4 molecules can be measured in the serum of AIDS patients in order to evaluate the therapeutic efficacy of treatments such as the administration of AZT, interferon, or CD4 itself.

In further embodiments, total CD4 marker immunologically related to CD4 antigen can be measured and used in specific embodiments such as the prediction of therapeutic outcome of AIDS patients following administration of therapeutic compounds such as AZT, interferon or CD4.

In another embodiment, total CD8 antigen can be measured and correlated with disease progression or treatment outcome.

Measurement of total T cell antigen receptor can be especially useful in monitoring the effectiveness of treatment with agents such as T cell receptor specific antibodies. In specific embodiments, the total TCR antigen in a specific subset of T cells expressing specific variable regions can be measured and correlated with treatment outcome.

The therapeutic treatments which may be evaluated according to the present invention include but are not limited to radiotherapy, drug administration, vaccine administration, immunosuppressive or immunoenhansive regimens, etc. The immunosuppressant regimens include, but are not limited to administration of drugs such as Cyclosporin A, chlorambucil, cyclophosphamide, or azathioprine, and anti-T cell antibody such as anti-T3 monoclonal antibody, anti-T cell antigen receptor antibody, and anti-thymocyte globulin, etc. The immunoenhansive regimens include, but are not limited to administration of interleukin-1, interleukin-2, interleukin-4 and other T cell growth factors.

5.2. DETECTING AND/OR STAGING A DISEASE IN A SUBJECT

In another embodiment of the present invention, measurement of a soluble molecule or of a total marker either of which comprise, or is immunologically related to, a T cell growth factor receptor, leukocyte surface molecule, complement receptor, or T cell differentiation antigen can be used to detect and/or stage a disease or disorder in a subject. The measured amount of the soluble molecule or of the total marker is compared to a baseline level. This baseline level can be the amount which is established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease. Disease or disorders which may be detected and/or staged in a subject according to the present invention include but are not limited to those listed in Table III, infra and discussed in Section 5.6.4 infra.

TABLE III

DISEASES AND DISORDERS WHICH MAY BE DETECTED AND/OR STAGED AND/OR MONITORED IN A SUBJECT ACCORDING TO THE PRESENT INVENTION

I. Infectious Diseases Induced by virus
Herpesvirus
Cytomegalovirus
Epstein-Barr Virus
HTLV-I
HTLV-III/LAV/HIV (AIDS)
II. Cancer
B or T cell leukemia
HTLV-I- associated adult T cell leukemia
B or T cell lymphoma
Burkitt's lymphoma
Hairy cell leukemia
Sezary syndrome
Hodgkin's disease
Chronic lymphocytic leukemia
Non-Hodgkin's lymphoma
B-cell acute lymphoblastic leukemia
Solid tumors
III. Autoinmune Diseases

TABLE III-continued

DISEASES AND DISORDERS WHICH MAY BE DETECTED AND/OR STAGED AND/OR MONITORED IN A SUBJECT ACCORDING TO THE PRESENT INVENTION

Rheumatoid arthritis
Diabetes
Multiple sclerosis
Systemic lupus erythematosis
IV. Organ Allograft Rejection
V. Red Blood Cell Diseases Autoimmune hemolytic anemia
Transfusion
Paraxismal nocturnal hemaglobinurea
Familial Mediterranean fever In specific embodiments of this aspect of the invention, measurements of levels of the soluble molecule and/or of the total marker or related molecules can be used in the detection of disease, or to determine disease stage and assign risk. For example, patients with lymphatic diseases and cancer such as non-Hodgkin's lymphoma, B cell acute lymphoblastic leukemia, Hodgkin's disease, or adult T cell leukemia can be monitored by measuring serum levels of soluble molecules and/or of the total marker and the levels determined can be correlated with severity of the disease condition and response to therapy as well as a disease prognosis. In another example, the response of patients with non-lymphatic cancers to therapy with IL-2 can be monitored. Thijs et al. (1990, J. Immunol. 144:2419-2424) reported an activation of the complement system in patients treated with IL-2. Levels of soluble CD35 and/or of total CD35 can be used to predict a response to IL-2 therapy.

Responses to viral infections can also be monitored by measuring soluble CD8 and/or total CD8 levels in a patient. For example, patients infected with herpes virus or an AIDS virus can present modified levels of soluble CD8 or total CD8. In other embodiments, soluble and/or total levels can be measured in transplant patients; and used as a diagnostic indication of allograft rejection.

In another embodiment, CD8 may be measured; detection of increased levels of soluble CD8 (TS) antigen and/or total CD8 can be associated with various diseases and disorders such as rheumatoid arthritis and infectious diseases such as EBV-induced mononucleosis. Detection of elevated levels of a CD8 antigen can indicate the involvement of significant numbers of suppressor/cytotoxic T cells with a specific pathological event, distinct from immune activation. Soluble CD8 and/or total CD8 antigen can also be used in staging Hodgkin's disease, and in monitoring therapeutic efficacy.

In another embodiment of the invention, detection of an increase in soluble CD4 and/or total CD4 antigen in the body fluid of a patient can be used to diagnose a state of immune activation. Soluble CD4 and/or total CD4 measurements can also be used to detect and/or stage adult T cell leukemia. Elevation of CD4 antigen levels in the synovial fluid of a patient can indicate rheumatoid arthritis. In another embodiment, elevated levels of soluble CD4 in synovial fluid relative to serum is a diagnostic indication of rheumatoid arthritis. In yet another embodiment, the detection of soluble CD4 or total CD4 in cell culture supernatants can be relied on as an indication of the CD4+ phenotype of the lymphocytes present.

5.3. DIFFERENTIAL DIAGNOSIS OF A PHYSIOLOGICAL CONDITION

In another embodiment of the invention, the measurement of soluble or total T cell growth factor receptors, leukocyte surface markers, complement receptors, T cell surface antigens, or immunologically related molecules can be used to differentially diagnose in a subject a particular physiological condition as distinct as from among two or more physiological conditions. To this end, the measured amount of the soluble molecule or total molecule is compared with the amount of the soluble molecule or total molecule normally present in body fluid of a subject with one of the suspected physiological conditions. A measured amount of the soluble molecule or total molecule similar to the amount normally present in a subject with one of the physiological conditions, and not normally present in a subject with one or more of the other physiological conditions, is indicative of the physiological condition of the subject.

In a specific embodiment, measures of serum CD8 levels may be used in the differential diagnosis of rheumatoid arthritis, as distinguished from other joint diseases.

5.4. DETECTING OR STAGING OF DISEASE OR MONITORING OF RESPONSE TO TREATMENT IN PATIENTS BY MEASUREMENT OF A PLURALITY OF LEUKOCYTE SURFACE MARKERS

The present invention also provides for the detecting or staging of disease, or the monitoring of treatment by measuring a plurality (at least two) of leukocyte surface markers (receptors or differentiation antigens). For example, a plurality of T cell markers either in soluble form or in total selected from, for example but not limited to, CD35, CD4 and CD8, to mention but a few, can be measured to diagnose, stage, or monitor treatment of diseases or disorders. Such diseases or disorders include those discussed supra in Section 5.1 through 5.3 (e.g., see Table II). Soluble and/or total marker levels can represent a measure of immune system function, paralleling disease course or treatment efficacy. In a preferred embodiment, the prognostic indicator is the observed change in different marker levels relative to one another, rather than the absolute levels of the markers present at any one time. Since CD4, CD8 and CD35 (soluble or total levels) are indicators of the immune system function, they should provide a much improved measure of the relative health of the immune system during various stages of disease or disorders.

In a preferred embodiment, measurements of a plurality of leukocyte surface markers are used to detect, stage, or monitor therapeutic treatment of diseases and disorders, e.g., from Table III. In a particular embodiment, diseases and disorders caused by HIV (the causative agent of AIDS) infection may be monitored by measurements of a plurality of leukocyte surface markers.

AIDS therapies include the treatment of AIDS patients with drugs such as AZT (azido-deoxythymidine), $\gamma$ or $\beta$ interferons, and with soluble CD4, or its fragments and derivatives, and the production of potential AIDS vaccines, such as gp120 peptides. Practitioners in AIDS therapy very much need a procedure that can be used to monitor the efficacy of these treatments or vaccines. To date, the levels of the HIV antigen p24 have not proved sensitive enough. Soluble or total CD4 in particular, and soluble or total CD8 and soluble CD35 as well, can be identified and detected in HIV-infected patients with different manifestations of disease, providing a sensitive immunoassay to monitor AIDS therapies and vaccines. In a preferred embodiment, the CELL-FREE ® Test Kit (T Cell Sciences, Cambridge, Mass.) assays can be useful for monitoring AIDS therapies and treatments. The measurement of total CD4 is an inexpensive and easy immunoassay format is a valuable clinical tool for predicting disease prognosis and treatment outcome in AIDS patients. Detection of soluble CD4 would be particularly useful in following HIV infection and AIDS therapy since CD4 is so intimately involved in AIDS etiology. Soluble CD4 is produced when CD4+ cells are activated (see Section 6.2, infra), in particular during HIV infection. Measurements of other leukocyte markers, such as CD35 and CD8, which also indicate the state of immune function, will also be valuable.

In a preferred embodiment, monitoring of AIDS treatment or disease progression can be made through measuring a profile of leukocyte markers, such as CD4, CD8 and CD35, rather than any individual marker alone. Such a profile can be obtained by determining the receptor levels of a panel of receptors either soluble or total in longitudinal samples of sera from patients undergoing treatment.

In a preferred aspect, the approach that can be taken is to determine the levels of soluble or total CD4 (and soluble or total CD8 and soluble or total CD35) levels in longitudinal time studies and to compare these values with a baseline level. The baseline level can be either the level of the marker present in normal, disease free individuals; and/or the levels present prior to treatment, or during remission of disease, or during periods of stability. These levels can then be correlated with the disease course or treatment outcome.

5.5. DETECTING OR DIAGNOSING DISEASE OR MONITORING RESPONSE TO TREATMENT IN PATIENTS BY COMPARING THE MEASUREMENT OF A PLURALITY OF LEUKOCYTE SURFACE MARKERS

The present invention also provides for the detection or diagnosis of disease or the monitoring of treatment by measuring the amounts of total marker (Section 5.7.2, infra) and of soluble marker in a sample and comparing the two measurements. The change in the levels of the markers relative to one another can be an improved prognostic indicator. A comparison of the amounts of a total marker with the amount of intracytoplasmic marker or membrane-bound marker is also envisioned.

5.6. SOLUBLE LEUKOCYTE SURFACE MOLECULES

Any leukocyte surface molecule or immunologically related molecule which is present in soluble form in the body fluid at levels which correlate with a disease condition or disorder, or a stage thereof, may be used in the practice of the present invention. Leukocyte surface markers which may potentially be used include but are not limited to those listed in Table I, supra.

In specific embodiments, soluble CD4 and/or CD4 cell surface molecules may be measured.

In other embodiments, soluble CD35 may be measured. Another embodiment includes the measurement of soluble CD8 and/or CD8 cell surface molecules.

Other T cell surface molecules whose soluble forms may be measured in accordance with the present invention include but are not limited to T cell growth factor receptors or binding proteins, complement receptors, T cell receptors, homing receptors or other binding proteins. In specific embodiments, serum CD4 measurements can be used to predict therapeutic outcomes and monitor the immune status of patients with cancer, immunodeficiencies, autoimmune diseases, or allograft rejection.

5.6.1. KITS AND ASSAYS FOR MEASUREMENT

Any procedure known in the art for the measurement of soluble molecules can be used in the practice of the instant invention. Such procedures include but are not limited to competitive and non-competitive assay systems using techniques such as radioimmunoassays, ELISA (enzyme linked immunosorbent assay), "sandwich" immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays, to name but a few. U.S. Pat. No. 4,845,026, issued Jul. 4, 1989, entitled "Assay Systems for Detecting Cell-Free T Cell Antigen Receptor Related Molecules and Clinical Utilities of the Assays" teaches a preferred method of immunoassay.

In a preferred embodiment, a sandwich enzyme immunoassay can be used. One description of such an embodiment follows: An antibody (capture antibody, Ab1) directed against the soluble antigen is absorbed onto a solid substratum. The soluble antigen present in the sample binds to the antibody, and unreacted sample components are removed by washing. An enzyme-conjugated antibody (detection antibody, Ab2) directed against a second epitope of the antigen binds to the antigen captured by mAb1 and completes the sandwich. After removal of unbound Ab2 by washing, a substrate solution is added to the wells. A colored product is formed in proportion to the amount of antigens present in the sample. The reaction is terminated by addition of stop solution and absorbance is measured spectrophotometrically. A standard curve is prepared from known concentrations of the soluble antigen, from which unknown sample values can be determined. In particular embodiments, such an assay may be used to determine soluble CD35 levels or soluble T cell antigen levels. In a preferred embodiment for the measurement of CD35 levels, anti-CD35 Polyserum R1 and Polyserum R2 (quality control tested anti-CD35 polyclonal antibodies) can be used as the capture and detection antibodies, respectively, in a sandwich immunoassay (such as the CELLFREE ® assay described in Section 16 infra). In a preferred embodiment for the measurement of soluble CD8 antigen levels, anti-CD8 mAbs 4C9 and 5F4 can be used as the capture and detection antibodies, respectively, in a sandwich enzyme immunoassay (such as described in Section 8, infra.) In a preferred embodiment for the measurement of soluble CD4 antigen levels, anti-CD4 mAbs 8F4 and R2B7 can be used as the capture and detection reagents, respectively, in a sandwich enzyme immunoassay (see Sections 5.6.3 and 6, infra.)

Kits for carrying out the assays of and used in the practice of the present invention are also within the scope of the invention. For instance, such a kit can comprise a pair of antibodies to the same leukocyte marker (receptor or antigen) which do not compete for the same binding site on the marker. In another embodiment, a kit can comprise more than one pair of such antibodies, each pair directed against a different leukocyte marker, thus useful for the detection or measurement of a plurality of leukocyte markers.

5.6.2. FORMULATION OF AN IMMUNOASSAY FOR THE PREFERENTIAL DETECTION OF SOLUBLE FORMS OF T CELL SURFACE MARKERS OVER SOLUBILIZED FORMS

The present invention also provides a way of deriving immunoassay systems which preferentially detect/quantitate physiologically released (soluble) forms of cell surface markers over solubilized (e.g. detergent-treated) cell surface markers. Such a method involves the use of recombinant forms of the specific cell surface marker to be assayed, which have been genetically engineered to be physiologically soluble (i.e. by deletion of DNA sequences encoding the transmembrane region). As an example, such recombinant forms are likely to lack epitopes found on the transmembrane region, which epitopes are thus specific to the solubilized cell surface marker and which epitopes are likely also to be absent from the physiologically released form of the marker. Thus, the recombinant molecule can be used to screen anti-cell surface marker antibodies for determination of the appropriate antibodies to be used for preferential detection of the physiologically released form of the surface marker. Pairs of antibodies can be screened for optimization of a sandwich ELISA for detection of soluble cell surface marker. This aspect of the invention is illustrated by way of example in Section 6, infra, where a soluble CD4 assay is devised that preferentially detects soluble CD4 relative to solubilized CD4.

Antibodies can be produced for testing for suitability for use in the detection of soluble forms of leukocyte surface markers. Such antibodies can be polyclonal or monoclonal. Monoclonal antibodies are preferred for use in most cases, however, polyclonal antibodies can provide unexpected advantages in some cases.

Various procedures known in the art may be used for the production of polyclonal antibodies to epitopes of a given leukocyte surface molecule. For the production of antibody, various host animals can be immunized by injection with a leukocyte surface molecule, a recombinant version thereof, synthetic protein, or fragment thereof, including but not limited to rabbits, mice, rats, etc. In a preferred embodiment, the immunogen is a truncated recombinant soluble form of the leukocyte cell surface molecule. Various adjuvants may be used to increase the immunological response, depending on the host species, and including but not limited to Freund's (complete and incomplete), mineral gels such as aluminum hydroxide, surface active substance such as lysolecithin, pluronic polyols, polyanions, peptides, oil emulsions, keyhole limpet hemocyanins, dinitrophenol, liposomes, and potentially useful human adjuvants such as BCG (bacille Calmette-Guerin) and corynebacterium parvum.

A monoclonal antibody to an epitope of the leukocyte surface molecule can be prepared by using any technique which provides for the production of antibody molecules by continuous cell lines in culture. These include but are not limited to the hybridoma technique originally described by Kohler and Milstein (1975, Nature 256:495–497), and the more recent human B cell hybridoma technique (Kozbor et al., 1983, Immunology Today 4:72) and EBV-hybridoma technique (Cole et al., 1985, Monoclonal Antibodies and Cancer Therapy, Alan R. Liss, Inc., pp. 77–96).

In one embodiment, the monoclonal antibodies may be human monoclonal antibodies, chimeric human-mouse (or other species) antibodies, or humanized monoclonal antibodies. Human monoclonal antibodies may be made by any of numerous techniques known in the art (e.g. Teng et al., Proc. Natl. Acad. Sci. U.S.A. 80:7308–7312; Kozbor et al., 1983, Immunology Today 4:72–79; Olsson et al., 1982, Meth Enzymol. 92:3–16). Chimeric antibody molecules may be prepared containing a mouse (or human, or rat, or other species) antigen-binding domain with human constant regions (Morrison et al., 1984, Proc. Natl. Acad. Sci. U.S.A. 81:6851; Takeda et al., 1985, Nature 314:452). Humanized antibodies may be recombinantly prepared such that only the hypervariable domains are non-human sequences.

A molecular clone of an antibody to an epitope of a leukocyte surface molecule can be prepared by known techniques. Recombinant DNA methodology (see e.g., Maniatis et al., 1982, Molecular Cloning, A laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g. immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of F(ab')2 fragment, and the Fab fragments which can be generated by treating the antibody molecule with papain and a reducing agent.

Once specific antibodies are demonstrated to be suitable for use in the preferential detection of soluble leukocyte surface molecules, other such suitable antibodies may be selected by virtue of their having the same epitope specificity as the former antibodies. Such similar epitope specificity can be ascertained, for example, by observing the ability of a second antibody to inhibit binding of a first antibody to its antigen.

5.6.3. SOLUBLE CD4 AND ASSAY FOR ITS DETECTION

The invention is also directed to assays for measurement of soluble (released) CD4, which assays preferentially measure soluble CD4 over the solubilized membrane form of CD4. Examples of such assays are detailed infra in Section 6.

In a preferred embodiment for the detection or measurement of soluble CD4 antigen levels, anti-CD4 mAbs 8F4 and R2B7 can be used as the capture and detection reagents, respectively, in a sandwich immunoassay.

We also demonstrate infra that the physiologically released form of CD4 is physically different from that of the solubilized cell surface form, and that assays which quantitate the solubilized cell surface form do not necessarily quantitate the released form.

Soluble CD4 has been specifically quantitated, according to the present invention, and has been shown to be a reliable indicator of various pathological conditions (see Section 6, infra). Thus, detection and/or measurement of soluble CD4 can be used to diagnose, to monitor, and/or to stage various diseases, disorders and treatments involving the immune system.

5.6.4. SOLUBLE CD35 AND ASSAY FOR ITS DETECTION

The invention is directed to an improved immunoassay based upon polyclonal antibodies that is able to detect both soluble CD35 (sCD35) and soluble recombinant CD35 (see Section 5.6.1, supra). Such an immunoassay is detailed in Section 16, infra. Polyclonal anti-CD35 antibodies can be used for detecting spontaneously released CD35 in patients' sera and can also be used to monitor the effectiveness of therapeutic treatments in patients where CD35 is either spontaneously released due to the pathological condition or where recombinant CD35 has been administered to the patient as a therapeutic agent. The CD35 assay can be used to detect soluble CD35 in patients with certain diseases or disorders. The CD35 levels so obtained can then be correlated with disease stage, treatment regimen, and disease or disorder prognosis. Changes in soluble CD35 values may be more predictive than the absolute level of CD35 at any point in time. Changes in sCD35 values can be compared with predisease values, pretreatment or disease remission values, values observed in normal individuals, etc. Comparison of sCD35 values with other soluble markers, such as sCD4, sCD8 or sIL-2R are expected to give even better correlations with disease or better predictions of treatment efficacy from the monitoring of treatment outcome by the measurement of several soluble markers.

The measurement of sCD35 can be used in the diagnosis, staging, monitoring, and in the prediction of therapeutic outcome in diseases or disorders involving complement. These include but are not limited to the disorders and diseases described in more detail below, including those with circulating immune complexes, e.g., autoimmune disease such as systemic lupus erythematosis, rheumatoid arthritis, and glomerulonephritis, inflammation, infectious disease, such as AIDS, transplantation, blood transfusion, hemodialysis, cardiopulmonary bypass, thermal injury, adult respiratory distress, sepsis, barotrauma.

Autoimmune Disease

Diminished expression of CD35 on erythrocytes of patients with SLE has been reported by investigators from several geographic regions, including Japan, the United States, and Europe. Taken as a group, patients have an average number of receptors per cell that is 50–60% that of normal populations, although there is considerable overlap because of the genetically determined marked variation in this characteristic among normal individuals.

The mechanism(s) accounting for the reduction of CD35 number in SLE patients is not known and is an issue about which there is considerable discussion. An early report did not directly address the question of inheritance, but noted that CD35 number on erythrocytes varied inversely with disease activity, with lowest numbers occurring during periods of most severe manifestations of SLE, and higher numbers being observed during periods of remission in the same patient (Inada, et al, 1982, Clin. Exp. Immunol. 50:189–197; Tayler et al., 1983; Arthritis Rheum, 26:73644).

Recently acquired loss of erythrocyte CD35 in the setting of active SLE and hemolytic anemia was demonstrated by observing the rapid loss of the receptor from transfused erythrocytes (Walport et al., 1987, Clin. Exp. Immunol. 69:501-7).

These abnormalities contribute to the pathogenesis of the disease by altering the clearance of immune complexes and may be indicative of complement-dependent cellular processes, such as B cell activation, that are fundamental to SLE. Immune complexes are found in many pathological states including but not limited to autoimmune diseases such as rheumatoid arthritis or SLE, hematologic malignancies such as AIDS (Tayler et al., 1983, Arthritis Rheum. 26:73644; Inada et al., 1986, AIDS Research 2:235–247) and disorders involving autoantibodies and/or complement activation (Ross et al., 1985, J. Immunol. 135:2005–14). Erythrocytes are involved in the removal of circulating immune complexes via adherence to erythrocyte-CD35 and may function to inhibit deposition of immune complexes in body tissue. A method of treatment for the removal and immobilization of circulating immune complexes involves the transfusion of packed erythrocytes with high CD35 activity. This process is dependent upon complement consumption. Monitoring soluble CD35 levels during the treatment may aid in determining the effectiveness of the procedure.

Inada et al. has reported in a series of papers that erythrocyte CD35 has a functional role in the removal of circulating immune complexes in autoimmune patients and may thereby inhibit the deposition of immune complexes within body tissue constituents (Inada et al., 1989, Ann. Rheum. Dis. 4:287). Their findings also suggest detrimental loss of CD35 activity progressing from asymptomatic seropositive homosexuality volunteers to the prodromal spectrum of ARC and finally progressing to a total disappearance in overt AIDS (Inada et al., 1986, AIDS Res. 2:235). The measurement of soluble CD35 may provide a good indicator for predicting disease progression. There is an association of clinical disease state with a decreased CD35 activity rather than with levels of circulating immune complex (Inada et al., 1986, supra).

Hemodialysis

The measurement of CD35 expression by neutrophils is useful for the analysis of in vivo complement activation. All CD35 associated with erythrocytes, and most CD35 in B cells, is located at the plasma membrane. In contrast, in the unstimulated peripheral blood neutrophil and monocyte, 10% or less of the total cellular CD35 is at the plasma membrane, the rest being in an intracellular vesicular compartment. In vitro studies have demonstrated that CD35 can be elicited from this intracellular pool to the plasma membrane within seconds following stimulation of neutrophils with chemotactic peptides, such as C5a and formylmethionylleucylphenylalanine, certain cytokines and endotoxin. Thus, increased numbers of CD35 molecules at the plasma membrane of neutrophils in peripheral blood may be taken as evidence of in vivo cellular activation by one of these agents. This prediction was verified in studies of patients undergoing hemodialysis for chronic renal failure in whom there was a three-to five- fold increase in the amount of CD35 at the cell surface of neutrophils taken during dialysis with membranes that activated complement but not with non-complement activating membranes.

The use of a hemodialyzer also activates the alternative pathway. Levels of Bb, iC3b, C3a and C5a increase, but C4d levels do not change (Oppermann et al., 1988, Klin. Wochenscher 66:857–864; Kojima et al., 1989; Nippon Jenzo Gakkai Shi 31:91–97; Ueda et al., 1990, Nippon Jenzo Gakkai Shi 32:19–24). Terminal complement complex was demonstrated in the plasma (Kojima et al., 1989, supra), and on the membranes of granulocytes during dialysis (Deppisch et al., 1990, Kidney. Int. 37:696–706).

Cardiopulmonary Bypass

The use of pump-oxygenator systems in cardiopulmonary bypass and hemodialysis has been associated with a systemic inflammation reaction, which may result in profound organ dysfunction. These effects have been collectively termed as the post-pump syndrome or post perfusion syndrome. The clinical findings of this syndrome are similar to the biological activities of C3a and C5a. Indeed, elevated C3a has been demonstrated in patients undergoing prolonged extra corporeal circulation (Chenoweth et al., 1981, Complement 3:152–165). Increased plasma levels of SC5b-9 (Dalmasso et al., 1981, Complement Inflamm. 6:36–48), and terminal C5b-9 complexe deposits on erythrocytes and polymorphonuclear cells (Salama et al., 1988, N. Engl. J. Med. 318:408–414) have been observed in these patients.

Several lines of evidence showed that the complement system in cardiopulmonary bypass is activated primarily via the alternative pathway:
(1) C3a level was increased, but not C4a, suggesting that alternative pathway was predominantly responsible (Cavarocchi et al., 1986, Circulation 74: III 130–133; Chenoweth et al., 1986. Complement 3:152–165). However, protamine sulfate (a heparin antagonist) administration after cardiopulmonary bypass activated the classical pathway (Chenoweth et al., 1986, supra; Kirklin et al., 1986, Ann. Thorac. Surg. 41:193–199; Weiler et al., 1990, J. Allergy. Clin. Immunol. 85:713–719);
(2) Hack et al., (1988, J. Immunol. Methods, 108:77–84) showed that although C3a des arg was generated, C1-C1-inhibitor complexes, an indicative of classical pathway activation, did not increase.

Two types of oxygenators (bubble and membrane) have been used for cardiopulmonary bypass. The bubble oxygenator generated more C3a production than the membrane oxygenator (Cavarocchi et al., 1986, J. Thorac. Cardiovasc. Surg. 91:252–258). In an experimental model, the dogs which had bubble oxygenator developed higher risk of infection with *Staphylococcus aureus* than those with the membrane oxygenator, suggesting the decreased complement levels may impair the host defense during cardiopulmonary bypass (van Oeveren et al., 1987 Ann. Thorac. Surg. 44:523–528).

Three experimental models for cardiopulmonary bypass have been identified, rat (Alexander & Al Ani, 1983, J. Surg. Res. 35:28–34), pig (Nilsson et al., 1990, Artif. Organs 14:46–48) and cynomolgus monkey (Maeo, 1989, Nippon Kyobu Geka Gakkai Zasshi 37:2166–2174).

Thermal Injury (burn)

Most of the pathologic processes initiated by burns are inflammatory in nature. The main complications are shock, pulmonary edema, and infection. It has been shown that massive activation of the alternative complement pathway, but not the classical pathway, was observed in a model of burn injury in mice; cobra venom factor (CVF) pretreatment reduced burn mortality (Gelfand et al., 1982, J. Clin. Invest. 70:1170–1176). Elevations of plasma C3a des Arg and C4a des Arg were also detected in burn patients (Davis et al., 1987, Surgery 102:477–484).

Several small animal models of thermal injury regarding complement activation have been reported and can be used. Activated C3 was detected in plasma of a guinea pig model (Bjornson et al., 1986, J. Infect. Dis. 153:1098–1107). Complement-depletion diminished the generation of C5a (Oldham et al., 1988, Surgery 104:272–279) and burn edema (Friedl et al., 1989, Am. J. Pathol. 135:203–217) in a rat cutaneous burn model. In another rat model complement depletion also attenuated the systemic hemodynamics depression (Schirmer et al., 1989, J. Trauma 29:932–938). Furthermore, it has been suggested that neutrophil sequestration occurs very early in a sheep thermal injury animal model, probably as a result of oxidant initiated complement activation (Demling et al., 1989, Surgery 106:52–59). Thermal trauma appears to cause complement activation with anaphylatoxin release and mast cell secretion of histamine, leading to enhancement of xanthine oxidase activity and increased production of oxygen radicals by neutrophils which damage endothelial cells.

Neutrophil activation was also demonstrated in patients with thermal injury whose neutrophils have increased expression of CD35 for up to three weeks following the initial burn, and in whom infectious disease complications, such as sepsis or pneumonia, were associated with transient, further increases in CD35 expression by neutrophils.

Adult Respiratory Distress Syndrome (ARDS)

ARDS is a fulminant form of respiratory failure affecting many critically ill patients. Patients with sepsis, trauma, hypertransfusion, multiple fractures, gastric aspiration or pancreatitis are at risk of ARDS. The current therapy with high-dose methylprednisolone remains largely supportive and has had little impact on mortality (Luce et al., 1988, Am. Rev. Respir. Dis. 138:62–68). Both complement and leukocytes were implicated in the pathogenesis of ARDS. It has been reported that in the first 48 hours, complement activation occurred via the alternative pathway only and was later followed by activation via the classical pathway (Zilow et al., 1990, Clin. Exp. Immunol 79:151–157). Clr Cls-C1 inhibitor complex, C3b-P complex (Langlois et al., 1989, Heart Lung 18:71–84), and terminal complement complex (Langlois et al., 1988, Am. Rev. Respir. Dis. 138:368–375) were suggested to be useful to distinguish patients with ARDS from those without ARDS. Moreover, the amounts of C3a and C5a in patients with respiratory failure correlated with the severity of the eventual pulmonary insult (Weigelt et al., 1988, J. Trauma 28:1013–1019)

Several animal models are available to demonstrate the involvement of complement and the efficacy of sCD35 measurement for this disease entity. New Zealand white rabbits infused with activated complement developed clinical and morphological characteristics of the early phase of ARDS (Nuytinck et al., 1986, Brit. J. Exp. Pathol. 67:537–548). Cerulein-induced acute pancreatitis in rats is associated with an ARDS-like acute lung injury (Guice et al., 1988, Ann. Surg. 208:71–77). Decomplementation with cobra venom factor (CVF) in this model protected against lung injury (Guice et al., 1989, Ann. Surg. 210:740-747). Similarly, complement-depletion by CVF in a porcine model produced by infusion of live *Pseudomonas aeruginosa* developed less septic acute respiratory disease (Dehring et al., 1987, J. Trauma 27:615-625). When 5 cynomolgus monkeys (Macaca fascicularis) were made acutely septic with infusions of E. coli, severe sepsis and ARDS resulted (Stevens et al., 1986, J. Clin. Invest. 77:1812-1816). Three major early events occurred: generation of C5a, decrease in peripheral leuckocyte counts, and increase in the sequestration of leukocytes in the lungs (Hangen et al., 1990, J. Surg. Res. 48:196-203). In this model, ARDS was prevented with a rabbit anti-human polyclonal antibody to C5a des arg (Stevens et al., 1986, supra); the C3a and C4a levels were elevated, but not C5a (Hangen et al., 1989, J. Surg. Res. 46:195-199). This antibody was also shown to be able to inhibit polymorphonuclear chemotaxis and reduce the release of lysosomal enzymes (Hatherill et al., 1989, J. Biol. Response Mod. 8:614-624). These data indicate the important role of chemoattractant C5a in ARDS.

Sepsis

The mortality of sepsis is high, mainly due to complications such as shock and ARDS. Activation of the complement system via the classical pathway is suggested to be involved in the development of fatal complications in sepsis (Hack et al., 1989, Am. J. Med. 86:20-26). Elevated C3a and are associated with a fatal clinical outcome of sepsis. There are two animal models of sepsis reported; a rat cecal ligation and puncture model (von Allmen et al., 1990, J. Surg. Res. 48:476-480) and a sheep common bile duct contamination model (Barke et al., 1990, Arch. Surg. 125:437-440).

Barotrauma

It has been hypothesized that the phenomena of decompression sickness (DCS) are mediated by complement. The complement system is activated in rabbits with DCS. When these rabbits were pharmacologically decomplementing in vivo, they did not develop DCS (Ward et al., 1990, Undersea Biomed. Res. 17:51-66).

Therapy

In addition to the complement mediated diseases and treatments discussed Supra, it has been demonstrated that a recombinant produced soluble complement receptor type I (sCD35) functions as an in vivo inhibitor of complement and acts to suppress post-ischemic myocardial inflammation and necrosis (Weisman et al., 1990, Science, 340:146-151).

5.7. TOTAL LEUKOCYTE SURFACE MOLECULES

Prior to the instant invention, measurement of the amount of leukocytes positive for a leukocyte marker was carried out by direct analysis of cells. To date, investigators have primarily measured the amount of cell surface markers in enriched cell populations derived from whole blood. This involved separating whole blood into its serum (or plasma) and cell constituents followed by enrichment of the desired cells by procedures such as those involving the lysis of red blood cells and subsequent isolation of white blood cells on density gradients of polymers, such as Ficoll-Hypaque. The enriched cell populations can then be analyzed either by direct or indirect immunofluorescence involving flow cytometers or fluorescent microscopes, or alternatively lysed with appropriate buffers followed by analysis of either the total lysate or membrane and cytosolic components individually. Limitations to these procedures include (1) the requirement for fresh samples (2) the need to use enriched cell populations rather than whole blood, (3) the requirements of expensive equipment, (4) the time involved in preparing the samples and (5) the need for fairly large sample sizes or cell numbers for analysis, since cells are lost during the sample preparation steps and because flow cytometric analyses require that a statistically significant number of cells be analyzed for reliable measurements to be obtained. In diseases where the cells of interest are steadily declining, (for example, the decrease in the number of CD4 cells during HIV infection and progression to AIDS) larger sample volumes must be used in order to obtain a significant number of cells to analyze in the enriched cell population. The method provided by the present invention, set forth below, overcomes these limitations.

5.7.1. MEASUREMENT OF TOTAL LEUKOCYTE SURFACE MARKER

The present invention provides a method for determining the approximate amount in a sample of body fluid from a patient of leukocytes positive for a leukocyte marker; this is accomplished by measuring the total amount of the leukocyte marker in the sample. The total amount of a leukocyte surface molecule (hereinafter also termed leukocyte antigen) exists in three compartments, the cell membrane, intracytoplasmic and released/soluble compartments ("total marker"). One embodiment of this invention involves immunoassays that measure the total amount of a marker present in all three compartments. Further embodiments of the invention provide assays that will measure (1) the total amount of marker in the intracytoplasmic and membrane compartments for samples where the serum or cell culture supernatants have been removed and only cells are being analyzed; (2) the total amount of marker in the membrane compartment for samples where the intracytoplasmic and soluble compartments have been removed leaving just the cell membranes to be analyzed; or (3) the total amount of marker in the released/soluble compartment, i.e., serum, body fluid or culture media where the cells have been removed.

Total leukocyte antigens may be measured in samples consisting of or derived from a biological fluid, e.g., whole blood, plasma, serum, blood cells, saliva, urine, synovial fluid, pleural effusions, tumor and tissue infiltrates, amniotic fluid, spinal fluid or cranial fluid. In another embodiment, the biological fluid may be cell culture fluid.

The amount of total antigen can be determined in an immunoassay based upon the immunospecific recognition of a specific antigen by antibody(ies). To determine the total amount of a marker, a sample, such as whole blood, is first treated to solubilize the cellular components.

The preferred method of solubilizing cells without interfering with immunospecific binding is to treat the cells with concentrated non-ionic detergent or detergents followed by dilution prior to assay. Other methods of solubilizing cells, e.g., repeated freeze-thaw cycles, sonication or the addition of lower concentrations of detergents, are not as effective. Ionic detergents such as SDS are not effective, since SDS interferes with the subsequent antibody:antigen binding. In a preferred embodiment, cells are solubilized with Triton X-100, Nonidet P-40, and/or CHAPS. In a more preferred embodiment, cells are solubilized with 1% Triton X-100 and 1% Nonidet P-40 (NP-40). After solubilization, the sample is diluted with buffers prior to analysis in an immunoassay. This invention provides a method to solubilize cells without interfering in subsequent antibody-antigen binding.

In one embodiment, 100 μl of solubilized sample may be assayed for total leukocyte antigen. In a more preferred embodiment, 5–10 μl of solubilized sample may be used. Furthermore, a solubilized sample may be stored frozen, e.g., so that samples taken at different times may be assayed in a single experiment. In one embodiment, the sample is stored at −20° C. In a preferred embodiment, the sample is stored at −70° C.

Any method of detecting and measuring leukocyte antigens may be used in the practice of this invention. Thus, all of the methods described in section 5.6.1, supra, may be used to measure a total lymphocyte surface molecule. In a preferred embodiment, a sandwich immunoassay may be used. In a more preferred embodiment, the immunoassay may be a CELLFREE® assay kit.

A modification of the above-described method can also be used to assay any total leukocyte surface molecule or marker, i.e., leukocyte antigen, e.g., the markers described in Sections 2.1 and 2.2, supra. For example, and no by way of limitation, total CD4, total CD8, or total TCAR may be measured in the practice of this invention. In another embodiment, a plurality of two or more total leukocyte surface molecules or markers may be measured. In yet a further embodiments, the relative amount of one marker may be compared to another.

In a particular embodiment of the invention of total leukocyte surface marker or markers provides a method to detect, diagnose, or stage a disease in a subject, as described n Sections 5.2, 5.3, 5.4 or 5.5, supra. In another embodiment, measurement of total leukocyte surface marker or markers provides a method to monitor the effect or response to a therapeutic treatment, as described in Sections 5.1, 5.4 and 5.5, supra.

Measurement of the total amount of a marker is an improvement over measuring the cell bound, cell lysate or soluble marker for the following reasons. Firstly, the measurement can include the total amount of markers present in all three compartments, not just the amounts present in one or two compartments. Secondly, the measurement of total markers is easier than other procedures that involve greater sample preparation, complex equipment and more steps. Thirdly, small quantities of sample, e.g., 100 μl, and as little as 5 μl of whole blood, can be directly analyzed in a simple immunoassay format without prior enrichment of the samples. This represents a significant cost reduction per sample analyzed, and the elimination of an expensive equipment requirement, thereby making the analysis widely available to many laboratories or clinics. Fourthly, the measurement of total marker is an improvement, since it involves minimum sample preparation and does not create aerosols that are hazardous in the case of infectious samples from patients. Most important, for infectious samples such as those containing HIV, the solubilization procedure, i.e., treatment with concentrated detergent, inactivates the virus, thereby making subsequent analysis safer. Fifthly, the total marker assay does not require fresh samples. Each patient sample can be solubilized and stored frozen. This is especially useful for a series of samples obtained from the same patient over a period of time as in a longitudinal study. Each sample can quickly be solubilized and frozen so that all samples can be thawed and analyzed simultaneously. This is a definite improvement over flow cytometric analysis where the cells need to be fresh and intact. It also eliminates variance obtained in assay results that arise from interassay variability, since all of the assays may be performed at one time.

5.7.2. KITS AND ASSAYS FOR MEASUREMENT OF TOTAL LEUKOCYTE SURFACE MOLECULES

The instant invention provides a method to prepare a sample to measure total marker. Many different immunoassays and assay formats can be used to detect the immunologic determinant of interest. These include but are not limited to the immunoassays described in this application for measuring soluble markers. Kits for carrying out the assays for total marker include kits with components that allow the measurement of multiple total marker in one sample, for example the measurement of total CD4 and total CD8. In another embodiment, kits of this invention allow the measurement of total marker and soluble marker in the same sample, for example, measurement of total CD35 and soluble CD35.

5.7.2.1. TOTAL CD4 ASSAY

In a particular aspect, this invention also provides an immunoassay that measures total CD4 and allows a quantitative estimation of the number of CD4+ T cells in a sample. The correlation of total CD4 with the absolute number of CD4+ T cells is an important finding since a total CD4 assay can be used to monitor AIDS progression or treatment, and obviates the need for expensive, complex cytometers and their associated costs. Furthermore, the detergent treatment taught in the total CD4 assay inactivates HIV. Total CD4 measurements can be used to monitor AIDS patients, determine AZT eligibility, and monitor therapeutic treatments. For example, a total CD4 assay may be used to estimate the member of CD4+ T cells in a patient sample. If the amount of total CD4 correlates with a CD4+ T cell count of below 500 cells/mm$^3$ (Cowley et al, Jun. 25, 1990, Newseek, pp. 23–27; Mills & Masur, August, 1990, Scientific American, pp. 50–57; Fahey et al., 1990, New Engl. J. Med. 322:166–72; Goedert et al., 1989, New Engl. J. Med. 321:1141-8), then the patient is indicated for therapeutic intervention.

5.7.2.2. TOTAL CD8 ASSAY

In another aspect, invention is also directed to a method of preparing samples for use in an immunoassay that measures total CDS. The levels of total CD8 measured by this assay correlate to the absolute number of CD8+T cells in both normal individuals and AIDS patients. The same improvements that relate to the total CD4 assay (Section 7 infra) of cost effectiveness, safety, sample volume, etc. also apply to this total CD8 assay as well as to the total T cell antigen receptor assay described infra.

5.7.2.3. TOTAL T CELL ANTIGEN RECEPTOR ASSAY

This invention is also directed to the measurement of total T cell antigen receptor. Depending upon the choice of antibodies in the assay it is possible to detect either total $\alpha\beta$ or total $\gamma\delta$ T cell antigen receptor as well as any of the-V$\beta$, V$\alpha$, V$\gamma$ or V$\delta$ subsets of T cells. Thus, whole blood samples can now be analyzed quickly, safely and reliably for the amount of specific subsets of T cells. These measurements will directly relate to the detection or diagnosing of disease and to monitoring therapeutic efficacy (see Section 2.1.6 supra for disease correlations).

6. SOLUBLE CD4 ANTIGEN

In the examples detailed herein, a sandwich immunoassay is described for the preferential detection of the soluble form of CD4 antigen relative to the cell-surface form of CD4 antigen.

6.1. MATERIALS AND METHODS
6.1.1. ANTIBODIES

Antibody Leu3a, biotin or FITC labeled, was purchased from Becton Dickinson, Mountain View, Calif. Antibodies OKT4 and OKT4A were obtained from Ortho Diagnostics, Raritan, N.J. Antibody IOT4 was obtained from Immunotech, Cedex, France and further purified by ammonium sulfate precipitation. Antibodies B67.2 and B66.1 were from G. Trincherie, Wistar Institute. Antibody 3G2 was from Sanchex Madrid, Madrid, Spain. Antibody R2B7 was obtained from a fusion of rat spleen cells (carried out according to standard procedures), from an animal immunized with whole human peripheral blood lymphocytes, with mouse SP2/0 myeloma cells. Clone R2B7 was selected from this fusion based on its ability to stain populations of peripheral blood lymphocytes identical to these identified by OKT4.

Antibodies were purified either by ammonium sulfate precipitation or by protein A sepharose using the Biorad MPAS buffer system (BioRad Corporation, Richmond, Calif.). Horseradish peroxidase (HRP) conjugates were prepared essentially according to the method of Wilson and Nakane (1978, in Immunofluorescence and Related Techniques, Knapp, W., et al., eds. Elsevier, p. 215) using a molar HRP to antibody ratio of four.

Antibodies generated from a fusion of mice immunized with intact T cells (Jurkat) were screened for their ability to substitute for Leu3A in the assay as follows: Plates were coated with R2B7 as described, blocked and incubated with recombinant soluble CD4 for 2 hours at 37° C. Plates were washed and 50 $\mu$l of each hybridoma supernatant at 1-10 $\mu$g/ml were added followed by 50 $\mu$l of biotinyl Leu3A. Following a 2 hour incubation, plates were washed and 100 $\mu$l of streptavidin peroxidase (0.5 $\mu$g/ml) was added for 30 minutes. Plates were washed and developed as described below.

6.1.2. IMMUNOASSAY PROTOCOLS
6.1.2.1. INITIAL ASSAY

The enzyme immunoassay for the CD4 antigen was based on the sandwich immunoassay technique. Briefly, each well of a microtiter plate (Nunc, certified high binding) was coated overnight at 4° C. with a solution of murine monoclonal anti-human CD4 antibody in PBS, pH 7.4. Any remaining protein-binding sites on the microtiter wells were then blocked for two hours at 37° C. with 300 $\mu$l per well of a solution of BSA (1%) (Kirkegard and Perry Laboratories, Md.) and Tween 20 (0.05%) (Zymed Laboratories, South San Francisco, Calif.) in phosphate buffered saline (PBS), pH 7.4. The wells were then washed three times with 350 $\mu$l per well of PBS (pH 7.4) with 0.05% Tween 20. Following the final wash step, the wash solution was aspirated from the wells and 50 $\mu$l of a sample diluent consisting of 0.15M NaCl, 25 mM Tris (pH 7.4) supplemented with bovine proteins was added to each well. Fifty $\mu$l of standard or sample were added to the appropriate wells in duplicate. The solution in the wells was mixed thoroughly by gently tapping the side of the plate for fifteen seconds. The plate was then sealed and incubated at 37° C. for 2 hours. At the end of this incubation period, the solution was aspirated from the plate and each well was washed three times with 350 $\mu$l of PBS/Tween 20 as above. One hundred $\mu$l of horseradish peroxidase (HRP) conjugated murine monoclonal anti-human CD4 antibody was added to each well of the microtiter plate, and the plate was again incubated at 37° C. for 2 hours, as above. At the end of this incubation, the wells were once again washed three times with PBS/Tween 20 as above. One hundred $\mu$l of o-phenylenediamine (0.2%) dissolved in 0.1M sodium citrate buffer, pH 5.5, was then added to each well of the plate and incubated at 24° C.+2° C. for 30 minutes. At the end of this final incubation, 50 $\mu$l of 2N $H_2SO_4$ was added to each well to stop the reaction and the absorbance of each well was read at 490 nm.

For assays involving biotinylated antibodies, biotin conjugates were substituted for the HRP antibody conjugate. After the 2 hour incubation, wells were washed and 100 $\mu$l of streptavidin horseradish peroxidase (Zymed Laboratories) at 0.5 $\mu$g/ml in 1% bovine serum albumin in tris buffered saline was added. Following a 30 minute incubation at 37° C., wells were washed and color developed as described above.

Where indicated, assays were also performed as a single step assay in which conjugated antibody was added at the same time as the sample and incubated for 4 hours at room temperature on a rotating shaker platform, after which washing and color development were performed as described.

6.1.2.2. OPTIMIZED ASSAY

The configuration of the initial assay was modified by optimizing each of the assay reagents. This resulted in an improved sensitivity for the overall assay where much lower levels of soluble CD4 could be reliably and reproducibly detected. The optimized assay configuration is given in Table IV.

TABLE IV

COMPARISON OF INITIAL & OPTIMIZED ASSAY CONFIGURATIONS

| INITIAL ASSAY | OPTIMIZED ASSAY |
|---|---|
| Blocking Buffer: | |
| 1% BSA + 0.05% Tween 20 | 0.5% Casein, 0.008% NP-40, 0.005% EDTA |
| Sample Diluent* | |
| 0.15 M NaCl, 25 mM Tris, supplemented with bovine proteins | 0.25% NP-40, supplemented with bovine proteins in PBS |
| Conjugate Diluent* | |
| 25% FCS in Tris buffered | 15% FCS, 0.15% NP-40 |

TABLE IV-continued

COMPARISON OF INITIAL & OPTIMIZED ASSAY CONFIGURATIONS

| INITIAL ASSAY | OPTIMIZED ASSAY |
|---|---|
| | saline + 0.25% NP-40 |

*Aggregated IgG was added to both the sample diluent and the conjugate diluent to remove any effect of rheumatoid factors in various samples.

Occasionally, it was observed that the presence of rheumatoid factor (RF) in some of the samples led to erroneous determinations of soluble CD4 that appeared as false positives. To remove this effect, aggregated IgG was added to the sample and conjugate diluent buffers. The aggregated IgG was prepared by heating a 100 μg/ml solution of IgG in 100 mM sodium phosphate buffer, 0.9% NaCl, pH 5.56 at 56°–60° C. for 50 minutes, followed by neutralization with dibasic sodium phosphate, 0.9% NaCl, pH 8 to give a final pH of 7.4.

6.1.3. CELL PROCEDURES

For stimulation experiments, peripheral blood mononuclear cells were prepared using Ficoll Hypaque gradients. Cells were put into culture along with phytohemagglutinin (PHA) (0.5 μg/ml) or phorbol myristate acetate (1 ng/ml) and ionophore A2317 (0.1 ng/ml) or OKT3 (anti-T3 monoclonal antibody) (2 μg/ml). Samples were taken daily. For long term cultures of cells from rheumatoid arthritis or lung cancer patients, cells were maintained on IL-2. Cells were removed from culture supernatants by centrifugation followed by filtration through 0.22 μm filters and stored frozen until analysis.

Cell surface phenotyping was performed using a Cytofluorograph II (Ortho Diagnostic System, Westwood, Mass.) and FITC labeled OKT4 or OKT8 (Ortho Diagnostic Systems, Raritan, N.J.).

Recombinant soluble CD4 was obtained from cell culture supernatant of a chinese hamster ovary (CHO) cell line transfected with CD4 truncated at the transmembrane exon (Fisher, R. A., et al., 1988, Nature 331:76–78).

6.2. RESULTS
6.2.1. USING INITIAL ASSAY PROTOCOL

Table V shows the initial results of screening serum samples for released CD4 using OKT4 or OKT4A as capture reagent, and Leu3a as a detection reagent.

TABLE V

CD4 DETECTION*

| | Capture Antibody: | |
|---|---|---|
| Sample | OKT4 | OKT4A |
| HPB T Cell Lysate | | |
| 5 × 10⁶ cells/ml | 0.895 | 0.139 |
| 2.5 × 10⁶ cells/ml | 0.769 | 0.079 |
| 1.25 × 10⁶ cells/ml | 0.549 | 0.046 |
| T Cell Leukemia Patient Serum*** | | |
| Sample 1184 | 0.000 | 0.000 |
| Sample 1174 | 0.000 | 0.020 |
| Sample 1195 | 0.004 | 0.040 |
| Sample 1147 | 0.004 | 0.000 |

*Values shown are OD$_{490}$, using the indicated capture antibody and biotinylated Leu3a as detection antibody.
**The indicated numbers of HPB (human leukemia T cell line) cells were lysed in 1 ml detergent buffer.
***Serum from patients with acute HTLV I associated T cell leukemia While this assay could detect solubilized CD4 in cell lysates, no detectable soluble CD4 was observed in the sera of patients with HTLV I associated T cell leukemia, which is a disease characterized by an intense activated population of T cells.

Subsequent efforts were focused on determining whether antibodies could be selected which might preferentially recognize a released (soluble) form of the CD4. Recombinant CD4, with the transmembrane and cytoplasmic regions deleted at the gene level, was used as a model antigen. Antibodies were coated onto microtiter wells overnight and blocked as described. Samples containing either buffer, detergent solubilized CD4 from the Jurkat T cell line at two different dilutions, or recombinant CD4 were added, followed by a second incubation with HRP-conjugated antibodies (or biotinylated Leu3a followed by streptavidin HRP). Each antibody was evaluated on both a capture and detection mode with all other antibodies on each of the samples. The results are shown in Tables VI and VII.

TABLE VI

CD4 DETECTION IN CELL LYSATES*

| | Capture Antibody | | | | |
|---|---|---|---|---|---|
| Detection Antibody | 3G2 | B66.1 | R2B7 | B67.2 | OKT4 |
| 3G2 | 0.204 | 0.227 | 0.154 | 0.242 | >2.00/1.9 |
| B66.1 | 0.053 | 0.064 | 1.420 | 0.053 | >2.00/1.28 |
| R2B7 | 0.230 | >2.0/0.93 | 0.217 | 1.843 | >2.09/>2 |
| B67.2 | 0.027 | 0.030 | 0.110 | 0.008 | 1.50 |
| OKT4 | 0.037 | 0.024 | 0.040 | 0.000 | 0.008 |
| Leu3A | 0.196 | 0.206 | >2.00/1.94 | 0.279 | >2.00/>2 |

*Cell lysates contained 5 × 10⁶ cells/ml. Values shown are OD$_{490}$. For those antibody pairs where absorbance was >2.0 for 5 × 10⁶ cells/ml lysate, the value for 1 × 10⁶ cells/ml is shown in same box preceded by a slash.

TABLE VII

RECOMBINANT SOLUBLE CD4 DETECTION †

| | Capture Antibody* | | | | |
|---|---|---|---|---|---|
| Detection Antibody* | 3G2 | B66.1 | R2B7 | B67.2 | OKT4 |
| 3G2 | 0.002 | 0.003 | 0.074 | 0.000 | 0.230 |
| B66.1 | 0.002 | 0.012 | 0.170 | 0.004 | 0.010 |
| R2B7 | 0.000 | 0.036 | 0.059 | 0.013 | 0.300 |
| B67.2 | 0.000 | 0.000 | 0.008 | 0.000 | 0.009 |
| OKT4 | 0.001 | 0.000 | 0.010 | 0.002 | 0.000 |
| Leu3A | 0.008 | 0.000 | 1.765 | 0.000 | 0.231 |

† Values shown are OD$_{490}$.
*mAb B53.1 was also used, but showed no positive results when used as either capture or detection reagent.

The data presented in Tables VI and VII reveals a wide range of assay efficacies for the detection of solubilized cell-surface CD4 antigen (in cell lysate) or recombinant soluble CD4 antigen. Optimal combinations for detection of recombinant or lysate CD4 antigen are shown in Table VIII.

TABLE VIII

OPTIMAL PAIRS OF ANTIBODIES FOR DETECTION OF DETERGENT SOLUBILIZED OR RECOMBINANT CD4

| Capture Antibody | Detection Antibody |
|---|---|
| R2B7 | Leu3A |
| R2B7 | B66.1 |
| B66.1 | R2B7 |
| B67.2 | R2B7 |
| OKT4 | R2B7 |
| OKT4 | B66.1 |
| OKT4 | B67.2 |
| OKT4 | Leu3A |
| OKT4 | 3G2 |

Interestingly, only the combination of R2B7 as a capture antibody with Leu3A as a detection antibody gave signal with the recombinant CD4 substantially equivalent to that seen in lysate, suggesting this pair might preferentially recognize soluble CD4.

Antibodies were generated from a mouse immunized with whole T cells and screened for their ability to replace Leu3a in an assay. 500 hybridoma clones were screened and three clones meeting the above criteria were identified. One of these clones, termed 8F4, showed the ability to block binding of FITC labeled Leu3A to CD4 positive T cell surfaces.

Antibodies 8F4 and R2B7 were evaluated with regard to optimal configuration in the assay. Table IX shows that 8F4 used as capture antibody with R2B7 used as detection antibody produced a significantly greater ratio of signal observed using recombinant soluble CD4 to signal observed using detergent solubilized membrane CD4, compared to the ratio of signal observed with R2B7 as a capture antibody and 8F4 as detection.

TABLE IX

CD4 DETECTION

| SAMPLE | 8F4 Capture and R2B7 Detection | R2B7 Capture and 8F4 Detection |
|---|---|---|
| HPB Cell Lysate (cells/ml lysate) | | |
| $2 \times 10^6$ | 1.683 | 1.178 |
| $1 \times 10^6$ | 1.005 | 0.619 |
| $5 \times 10^5$ | 0.583 | 0.370 |
| $2.5 \times 10^5$ | 0.274 | 0.172 |
| $1.25 \times 10^5$ | 0.135 | 0.090 |
| $6.25 \times 10^4$ | 0.067 | 0.045 |
| 0 | 0.014 | 0.013 |
| Recombinant Soluble CD4 Dilutions* | | |
| 1:2 | >2.0 | 1.411 |
| 1:4 | >2.0 | 0.991 |
| 1:8 | >2.0 | 0.666 |
| 1:16 | 1.165 | 0.309 |
| 1:32 | 0.718 | 0.152 |
| 1:64 | 0.382 | 0.074 |
| T Cell Culture Supernatants | | |
| ST16** T cell line | 0.187 | 0.135 |
| 5B4** T4 clone | 0.152 | 0.104 |
| 6D11** T4 clone | 0.171 | 0.120 |
| 5C8** T4 clone | 0.331 | 0.246 |
| TIL** 5C4 T8 clone | 0.037 | 0.019 |

*Ratios represent the dilutions of cell culture supernatant of transfected CHO cells expressing the recombinant soluble CD4 antigen.
** Sample designation The antibody used by Doumerc et al. (1986, 6th Intl. Congress of Immunology, Toronto, Ontario, Canada, Jul. 6–11, 1986, Abstr. 5.54.6, p. 708), IOT4, was evaluated for its ability to measure the same form of CD4 antigen as that detected in the assay using 8F4 with R2B7. Table X shows the results when IOT4 antibody was used as both capture and detection reagent as was done by Doumerc et al.

TABLE X

| Capture Antibody | Detection Antibody | | |
|---|---|---|---|
| | 8F4 | IOT4 | R2B7 |
| CD4 DETECTION IN CELL LYSATE* | | | |
| 8F4 +NP40 | .037 | 0.051 | 0.545 |
| −NP40 | .013 | 0.035 | 0.423 |
| IOT4 +NP40 | .624 | 0.035 | 0.381 |
| −NP40 | .063 | 0.017 | 0.040 |
| R2B7 +NP40 | ND | 0.040 | 0.400 |
| −NP40 | ND | 0.049 | 0.320 |

TABLE X-continued

| Capture Antibody | Detection Antibody | | |
|---|---|---|---|
| | 8F4 | IOT4 | R2B7 |
| RECOMBINANT SOLUBLE CD4 DETECTION* | | | |
| 8F4 +NP40 | .003 | .142 | 1.341 |
| −NP40 | .005 | .155 | 1.421 |
| IOT4 +NP40 | .004 | .010 | 0.010 |
| −NP40 | .006 | .014 | 0.006 |
| R2B7 +NP40 | ND | .133 | 1.18 |
| −NP40 | ND | .134 | 1.18 |

*Values shown are $OD_{490}$. Where indicated, 0.25% NP40 was present in both the sample diluent and conjugate diluent of the sandwich immunoassay. Recombinant CD4 assays were carried out using a standard dilution of cell culture supernatant of transfected CHO cells.
ND: Not determined Antibodies were evaluated for CD4 detection using different combinations of capture and detection reagents in assay matrices. Assays were carried out using 25% fetal calf serum in tris buffered saline, with and without Nonidet P40 (NP40) in both sample and conjugate diluents (Table X). IOT4 reacted with detergent solubilized CD4 but failed to react with the recombinant soluble CD4. Also shown in Table X are antibodies 8F4 and R2B7 in combination with themselves and IOT4. When used as a capture reagent, IOT4 detected only CD4 in cell lysates. Interestingly, however, when IOT4 was used as a detection reagent with 8F4 or R2B7 used as capture reagent, a much stronger signal is seen for the recombinant CD4 antigen than is seen with solubilized CD4 in cell lysates. It should be noted that this signal (for recombinant CD4) is significantly less than the signal obtained when R2B7 is paired with 8F4 as either detection or capture reagent. R2B7 when paired with itself was capable of a strong signal for both recombinant and cell lysate samples. Inclusion of NP40 failed to disrupt this signal. In contrast, 8F4 did not show such behavior, reacting only weakly with both cell lysate and recombinant material when used in both parts of the sandwich. IOT4 also failed to give a significant signal when paired with B66.1 and B67.2 for both cell lysate and recombinant samples.

Table XI shows the results of screening culture supernatants from T cell lines or clones derived from patients with rheumatoid arthritis or lung cancer.

TABLE XI

SOLUBLE CD4 AND CD8 DETECTION

| Sample Designation | Phenotype | Soluble CD8 (U/ml)* | Soluble CD4 (U/ml)* |
|---|---|---|---|
| 1 | CD4+ clone | | 249 |
| 2 | CD4+ clone | | 241 |
| 3 | CD4+ clone | | 277 |
| 4 | CD8+ clone | 2,388 | |
| 5 | CD4+ clone | | 90 |
| 6 | CD4+, CD8+ clone | 4,000 | 70 |
| TI1 5 | CD4+, CD8+ mixed line | 568 | 61 |
| TI1 6 | CD4+, CD8+ mixed line | 4,000 | 238 |
| TI1 6 2 | CD4+, CD8+ mixed line | 4,000 | 120 |
| TI1 7 PBT | CD4+, CD8+ mixed line | | 51 |
| TI1 4 | B cell line | | |
| 5B4 | CD4+ clone | | 120 |
| 6G7 | CD4+ clone | | 240 |
| 5A1 | CD4+ clone | | 223 |
| 5C8 | CD4+ clone | | 115 |
| 6G7 | CD4+ clone | | 193 |
| 6D11 | CD4+ clone | | 116 |
| 5B4 | CD4+ clone | | 150 |
| 6D2 | CD4+ clone | 53 | 176 |
| 5C4 | CD4+ clone | | 117 |
| ST1 2H1 | CD4+ clone | 52 | 178 |
| ST1 1C10 | CD4+ clone | | 160 |
| ST1 13G11 | CD8+ clone | 3,217 | |

TABLE XI-continued

SOLUBLE CD4 AND CD8 DETECTION

| Sample Designation | Phenotype | Soluble CD8 (U/ml)* | Soluble CD4 (U/ml)* |
|---|---|---|---|
| ST2 13C6 | CD4+ clone | | 132 |
| ST 13C6 2 | CD4+ clone | | 53 |
| ST2 11C12 | CD8+ clone | 1,046 | |
| ST2 13A10 | CD4+ clone | | 369 | 94 |
| ST2 CM | CD4+, CD8+ mixed line | 221 | |
| ST2 13H1 | CD8+ clone | 3,428 | |
| ST2 14A5 | CD4+ clone | 72 | 142 |
| ST2 13A5 | CD4+ clone | 71 | 161 |
| ST 13 PB | CD4+, CD8+ mixed line | 4,000 | 50 |
| ST 16 | CD4+, CD8+ mixed line | 901 | 247 |
| ST5 PBT | CD4+, CD8+ mixed line | 240 | |
| ST5 | CD4+, CD8+ mixed line | | |
| TI14 PBT | CD4+, CD8+ mixed line | 4,000 | 71 |
| TI14 10F8 | CD4+, CD8+ mixed line | 1,217 | 70 |
| ST12 | CD4+, CD8+ mixed line | 4,000 | |
| ST11 | CD4+, CD8+ mixed line | 4,000 | 139 |

*Blank values indicate undetectable levels. CD4 units were defined in terms of the amount of absorbance of CD4 antigen found in a lysate of $10^3$ Jurkat T cells in 1% NP40 buffer, as measured using 8F4 as capture and R2B7 as detection reagents. CD8 units were based on a reference preparation of culture supernatant from Jurkat T cells used to standardize the CELLFREE ® T8 (T Cell Sciences, Cambridge, MA) assay.

Cell phenotype was determined by flow cytometry. Soluble CD4 was determined using 100 μl cell culture supernatant in a single-step assay using R2B7 as the antibody immobilized on the solid phase with biotinyl Leu3a and streptavidin peroxidase used for detection. A commercially available sandwich immunoassay kit (CELLFREE® T8 Test Kit, T Cell Sciences, Inc., Cambridge, Mass.) was used to measure soluble CD8. The CD8 antigen detected by this assay has been characterized previously as a 52–55 kD dimer composed of monomer polypeptides, each with a molecular weight of approximately 27 kD. As shown in Table XI, 21 of 21 CD4+ clones showed soluble CD4 in the supernatant. Zero of four CD8+ clones showed soluble CD4 in the supernatant. The cell lines showed varying mixes of soluble CD4 and soluble CD8. No correlation was observed between cell number and level of soluble CD4.

Table XII shows the rate of release of CD4 into the media after in vitro stimulation of peripheral blood mononuclear cells.

TABLE XII

SOLUBLE CD4 LEVELS AFTER IN VITRO CELL STIMULATION

| Experiment # | Type of Cell Stimulation* | Days in Culture | Soluble CD4 (U/ml)** |
|---|---|---|---|
| 1 | PHA | 1 | 4.4 |
| | | 2 | 6.4 |
| | | 3 | 15.0 |
| | | 4 | 17.4 |
| 1 | OKT3 | 1 | 1.8 |
| | | 2 | 4.4 |
| | | 3 | 7.6 |
| | | 4 | 11.5 |
| 1 | NONE | 1 | 1.1 |
| | | 2 | 1.1 |
| | | 3 | 4.8 |
| | | 4 | <1.0 |
| 2 | PHA | 1 | 7.6 |
| | | 3 | 24.3 |
| | | 4 | 43.9 |
| | | 5 | 41.6 |
| 2 | Phorbol myristate, acetate plus ionophore A2317 | 1 | 10.3 |
| | | 3 | 12.9 |
| | | 4 | 12.7 |
| | | 5 | 7.8 |

*Carried out as described in section 23.1.3, supra.
**CD4 units were as defined for Table XI.

In experiment #1, PHA showed significantly greater effect than stimulation with OKT3. Similarly, in experiment #2, PHA was significantly more effective than phorbol esters and ionophores at inducing CD4 release. No significant release occurred when cells were put into culture without mitogen, suggesting release is an active process and not merely due to cell death.

Table XIII shows levels of soluble CD4 detected in sera of individuals with HTLV-1 associated adult T cell leukemia.

TABLE XIII

DETECTION OF SOLUBLE CD4 IN PATIENT SERA

| Sample Designation | Disease | Soluble CD4 (units/ml)* |
|---|---|---|
| 1165 | Acute Adult T Cell leukemia | 3.51 |
| 1166 | Acute Adult T Cell leukemia | 37.56 |
| 1167 | Acute Adult T Cell leukemia | 7.90 |
| 1168 | Acute Adult T Cell leukemia | 5.61 |
| 1169 | Acute Adult T Cell leukemia | 1.41 |
| 1170 | Acute Adult T Cell leukemia | 1.07 |
| 1171 | Acute Adult T Cell leukemia | 0.08 |
| 1172 | Acute Adult T Cell leukemia | 0.52 |
| 1173 | Acute Adult T Cell leukemia | 9.41 |
| 1174 | Acute Adult T Cell leukemia | 9.54 |
| 1175 | Chronic Adult T Cell leukemia | 8.92 |
| 1176 | Chromic Adult T Cell leukemia | 0.66 |
| 1177 | Chronic Adult T Cell leukemia | 2.54 |
| 1178 | Chronic Adult T Cell leukemia | 0.23 |
| 1179 | Chronic Adult T Cell leukemia | 0.31 |
| 1180 | Chronic Adult T Cell leukemia | 0.23 |
| 1181 | Chronic Adult T Cell leukemia | 1.83 |
| 1182 | Chronic Adult T Cell leukemia | 3.36 |
| 1183 | Chronic Adult T Cell leukemia | 2.21 |
| 1184 | Chronic Adult T Cell leukemia | 3.78 |
| 1185 | Smoldering Adult T Cell leukemia | 0.87 |
| 1186 | Smoldering Adult T Cell leukemia | 0.59 |
| 1187 | Smoldering Adult T Cell leukemia | 0.24 |
| 1188 | Smoldering Adult T Cell leukemia | 0.31 |
| 1189 | Smoldering Adult T Cell leukemia | 1.34 |
| 1190 | Smoldering Adult T Cell leukemia | 1.01 |
| 1191 | Smoldering Adult T Cell leukemia | 1.61 |
| 1192 | Smoldering Adult T Cell leukemia | 0.91 |

*Detected using R2B7 as capture reagent and biotinylated Leu3A as detection reagent. CD4 units were as defined for Table XI.

Individuals with the most active stages of the disease had the highest levels of soluble CD4 in their sera.

FIG. 1 shows the levels of CD4 in sera of normal individuals and in patients from a number of disease groups. Levels of CD4 in synovial fluid of rheumatoid arthritis patients and in sera of lung cancer patients were elevated as compared to the levels in sera from normal individuals.

Table XIV shows CD4 levels in longitudinal samples from patients on IL-2 therapy.

TABLE XIV

SOLUBLE CD4 LEVELS IN PATIENTS UNDERGOING IL-2 THERAPY*

| Patient Designation | Date (mo./day) | Soluble CD8 (U/mL) | Soluble CD4 (U/ml) | Soluble IL2R (U/ml) |
|---|---|---|---|---|
| A | 4/27 | 184 | 7 | 1302 |
| A | 5/04 | 492 | 19 | >1600 |

TABLE XIV-continued
SOLUBLE CD4 LEVELS IN PATIENTS UNDERGOING IL-2 THERAPY*

| Patient Designation | Date (mo./day) | Soluble CD8 (U/mL) | Soluble CD4 (U/ml) | Soluble IL2R (U/ml) |
|---|---|---|---|---|
| A | 5/06 | 531 | 28 | >1600 |
| A | 5/10 | 529 | 27 | >1600 |
| A | 5/11 | 490 | 22 | >1600 |
| B | 1/29 | 325 | 10 | 385 |
| B | 2/04 | 595 | 19 | >1600 |
| B | 2/10 | 1221 | 12 | >1600 |
| B | 2/12 | 914 | 17 | >1600 |
| B | 2/20 | 452 | 16 | >1600 |
| C | 1/05 | 319 | 21 | 964 |
| C | 1/15 | 1232 | 26 | >1600 |
| C | 1/21 | 890 | 26 | >1600 |
| D | 1/15 | 269 | 10 | 294 |
| D | 3/04 | 271 | 7 | >1600 |
| D | 3/09 | 519 | 16 | >1600 |
| D | 3/10 | 484 | 10 | >1600 |
| E | 3/23 | 621 | 14 | >1600 |
| F | 3/22 | 315 | 165 | 627 |
| F | 3/29 | 615 | 102 | >1600 |
| F | 4/05 | 898 | 140 | >1600 |
| Patient 1 | | 333 | 9 | 494 |
| Patient 2 | | 222 | 22 | >1600 |
| Patient 3 | | 274 | 12 | 683 |
| Patient 4 | | 149 | 11 | 650 |
| Patient 5 | | 1492 | 49 | >1600 |
| Patient 6 | | 1008 | 74 | >1600 |
| Patient 7 | | 608 | 8 | >1600 |
| Patient 8 | | 2094 | 27 | >1600 |
| Patient 9 | | 779 | 16 | >1600 |
| Patient 10 | | 1400 | 31 | >1600 |
| Normal 1** | | 476 | 9 | 466 |
| Normal 2** | | 311 | 6 | 540 |
| Normal 3** | | 178 | 3 | 396 |
| Normal 4** | | | 5 | |
| Normal 5** | | | 3 | |
| Normal 6** | | | 4 | |
| Normal 7** | | | 6 | |
| Normal 8** | | | 6 | |
| Normal 9** | | | 8 | |
| Normal 10** | | | 3 | |

*Soluble CD8 was measured using the CELLFREE ™ T8 Test Kit (T Cell Sciences, Cambridge, MA). Soluble CD4 was detected using 8F4 capture, R2B7 detection. CD4 units were as defined for TABLE XI. Soluble IL2R was measured using the CELLFREE ™ IL2R Test Kit (T Cell Sciences, Cambridge, MA).
**Healthy blood donors (not undergoing IL-2 therapy)

The data of Table XIV shows that detectable levels of soluble CD4 are present in sera of patients being treated with IL-2. One of the events observed in IL-2 therapy is an increase in circulating activated CD4 positive lymphocytes. Soluble CD4 levels in these patients fluctuate throughout the course of therapy and may have prognostic value.

Table XV shows levels of soluble CD4, along with soluble IL2R, in renal transplantation patients.

TABLE XV
SOLUBLE CD4 LEVELS IN RENAL TRANSPLANTATION PATIENTS

| Patient Designation | Sample Date (mo./day) | Soluble CD4* (U/ml) | Soluble IL2R † (U/ml) |
|---|---|---|---|
| P | 4/07 | 6.4 | 455 |
|   | 4/09 | 7.6 | 493 |
|   | 4/14 | 20.4 | 4090 |
|   | 4/16 | 9.3 | 3865 |
|   | 5/02 | 6.8 | 1200 |
|   | 5/30 | 37.4 | 565 |
| H | 3/14 | 16.4 | 811 |
|   | 3/21 | 11.7 | 441 |
|   | 4/09 | 12.4 | 347 |
|   | 5/14 | 21.6 | 692 |
|   | 6/11 | 36.9 | 907 |
| L | 6/15 | 91.8 | 1965 |
|   | 6/16 | 29.2 | 2705 |
|   | 6/23 | 38.1 | 3990 |
|   | 6/30 | 48.8 | 7400 |
|   | 7/07 | 35.2 | 6300 |
| G | 4/30 | 26.1 | 1288 |
|   | 5/05 | 7.6 | 700 |
|   | 5/07 | 24.2 | 1845 |
|   | 5/09 | 32.6 | 3625 |
|   | 5/12 | 17.1 | 3635 |
|   | 5/14 | 18.8 | 3035 |
|   | 5/16 | 21.2 | 3040 |
|   | 5/21 | 20.0 | 4080 |
|   | 6/04 | 46.5 | 2475 |
|   | 6/25 | 19.4 | 1995 |
| S | 6/13 | 6.6 | 1090 |
|   | 6/16 | 13.7 | 680 |
|   | 6/18 | 13.1 | 930 |
|   | 6/20 | 11.1 | 1705 |
|   | 6/23 | 8.3 | 2708 |
|   | 6/25 | 19.5 | 5515 |
|   | 6/27 | 11.2 | 3460 |
|   | 6/30 | 9.9 | 2205 |
|   | 7/07 | 12.8 | 1825 |

*Detected using 8F4 capture, R2B7 detection
† Analyzed using CELLFREE ® IL2R Test Kit Elevated levels of CD4 did not show a correlation with IL2R but did, like IL2R, show increases during rejection episodes.

6.2.2. RESULTS USING OPTIMIZED ASSAY PROTOCOL

Once the soluble CD4 assay was optimized and any effects of rheumatoid factor eliminated, it was possible to detect much lower levels of soluble CD4. For normal healthy individuals, the range of soluble CD4 was 8 U/ml to 36 U/ml with a mean of 17.2 U/ml. This was determined from the assay of 189 normal samples. A high number of replicates was also run to achieve confidence at the low end of the range.

Using this improved assay, a series of renal transplant patients was analyzed, and the data is presented in Table XVI.

TABLE XVI
RENAL TRANSPLANT PATIENTS

| PATIENT | Diagnosis[1] | Soluble CD4 (U/ml)[2] | Soluble IL-2R (U/ml)[3] | Soluble CD8 (U/ml)[4] |
|---|---|---|---|---|
| C1 | CsA | 69 | 200 | 181 |
|    | CsA | 30 | 340 | 448 |
| B1 | Rejection | 15 | 240 | 47 |
| Z1 | Stable | 19 | 380 | 310 |
|    | Stable | 19 | 390 | 374 |
|    | Stable | 15 | 300 | 321 |
| R1 | Rejection | 24 | 420 | 481 |
|    | Rejection | 33 | 820 | 120 |
| M1 | CsA | 122 | 770 | 534 |
|    | CsA | 29 | 330 | 570 |
|    | CsA | 26 | 80 | 526 |
| L1 | Rejection | 43 | 1040 | ND |
|    | Rejection | 30 | 1120 | ND |
| S1 | Rejection | 25 | 680 | ND |
| P1 | Rejection | 44 | 2180 | 1894 |
|    | Rejection | 25 | 370 | 390 |
| S2 | CsA | 117 | 510 | 267 |
|    | CsA | 22 | 390 | 67 |
| A1 | Stable | 96 | 400 | 731 |
|    | Stable | 27 | 320 | 390 |
|    | Stable | 23 | 40 | 409 |
| L2 | Rejection | 23 | 1240 | 228 |

TABLE XVI-continued

RENAL TRANSPLANT PATIENTS

| PATIENT | Diagnosis[1] | Soluble CD4 (U/ml)[2] | Soluble IL-2R (U/ml)[3] | Soluble CD8 (U/ml)[4] |
|---|---|---|---|---|
| | Rejection | too high | 1000 | 1559 |
| | Rejection | 24 | 1050 | 452 |

[1]Diagnosis was either cyclosporin A toxicity (CsA), stable transplant, or rejection; multiple patient serum samples were taken at different times.
[2]Soluble CD4 was measured using the improved assay (Section 23.1.2.2, supra).
[3]Soluble IL2R was measured using the CELLFREE ® IL-2R Test kit (T Cell Sciences, Cambridge, MA).
[4]Soluble T8 was measured using the CELLFREE ® T8 Test kit (T Cell Sciences, Cambridge, MA).
ND: Not Determined.

The above data indicates that it was possible to detect soluble CD4 levels in renal transplant patients in the phases of rejection, toxicity and stability. It was also possible to detect elevated levels of other soluble T cell surface markers, such as soluble CD8 and soluble IL2R. This data shows that soluble receptors are present during the course of transplant episodes. It is expected that a longitudinal study of each of these patients will provide data that will indicate how the levels of each soluble marker change with toxicity, rejection or stability episodes. Thus, a change in the observed level for any particular marker, such as an increase or decrease or no change, may be of more value than the absolute level of a marker present at any one point in time, for the diagnosis or monitoring of treatment in disease (see Section 25, infra). For comparison, the change in the observed level of a marker must be compared to a baseline level which could either be the level seen in normal individuals with no disease, the pre-transplant level in the renal patient, the value present in a stable situation or during remission of symptoms, etc.

In a preferred embodiment, the diagnosis of disease or monitoring of treatments of patients with renal transplants or other diseases and states of immune activation will be through an analysis of a panel of soluble T cell markers, rather than from only one individual marker. Thus, for example, a better prognostic indicator can be a rise in one marker relative to a simultaneous fall in another marker. The resulting profile of soluble T cell marker expression should be an exquisite indicator of minute changes in the immune system as its function is modified by therapeutic treatments or disease progression (see Section 26, infra).

Table XVII gives the values of soluble CD4 levels seen during preliminary studies on patients with Acquired Immune Deficiency Syndrome (AIDS) and other stages of HIV-induced disease including Kaposi's Sarcoma (KS), AIDS related complex (ARC) or asymptomatic seropositive (ASYM).

TABLE XVII

LEVELS OF SOLUBLE RECEPTORS IN HIV-INFECTED PATIENTS

| PATIENT | Diagnosis | Soluble CD4* (U/ml) | Soluble IL-2R* (U/ml) | Soluble CD8* (U/ml) |
|---|---|---|---|---|
| 1 | AIDS | 10 | 699 | 1236 |
| 2 | AIDS | 10 | 792 | 2351 |
| 3 | AIDS | 20 | 1092 | 1099 |
| 4 | AIDS | 21 | 506 | 1706 |
| 5 | AIDS | 24 | 2105 | 1104 |
| 6 | AIDS | 56 | 1340 | 753 |
| 7 | AIDS | 25 | 2099 | 1440 |
| 8 | AIDS | 1 | 1760 | 1007 |
| 9 | AIDS | 20 | 1964 | 626 |
| 10 | AIDS | 3 | 1079 | 306 |
| 11 | AIDS | 1 | 1529 | 343 |
| 12 | AIDS | 13 | 1025 | 647 |
| 13 | AIDS | —1 | 2014 | 438 |
| 14 | AIDS | 16 | 747 | 507 |
| 15 | ARC | 71 | 1645 | 2646 |
| 16 | ARC | 23 | 967 | 7331 |
| 17 | ASYM | 11 | 489 | 487 |
| 18 | ARC | 23 | 563 | 4073 |
| 19 | ARC | 177 | 1508 | 1246 |
| 20 | ARC | —0 | 978 | 572 |
| 21 | ARC | 15 | 2093 | 1731 |
| 22 | ARC | 16 | 1742 | 1279 |
| 23 | ASYM | 15 | 740 | 2700 |
| 24 | ASYM | 28 | 1403 | 1583 |
| 25 | ASYM | 24 | 1392 | 3037 |
| 26 | ASYM | 13 | 1084 | 2290 |
| 27 | ASYM | 12 | 558 | 1915 |
| 28 | ASYM | 19 | 1182 | 5580 |
| 29 | ASYM | 14 | 1308 | 1702 |
| 30 | ASYM | 16 | 806 | 430 |
| 31 | ASYM | 17 | 1012 | 1386 |
| 32 | ASYM | 13 | 1541 | 5127 |
| 34 | ASYM | 42 | 1752 | 4022 |
| 34 | ASYM | 10 | 504 | 1598 |

*Assays as indicated for Table XVI.

From the above data, it is clear that although the values of soluble CD4 are low compared to the other soluble marker levels, they are easily detectable in sera from patients having different stages of HIV-induced disease. As discussed supra, improved prognostic indices based upon levels or changes in levels of these soluble markers are expected with longitudinal studies involving a panel of soluble receptor markers. Such studies should reveal a profile of soluble receptors that can be used to determine the stage of progression towards AIDS in patients or the response to treatment of such patients. A longitudinal study of the patients in Table XVII and others can be conducted to determine the soluble receptor profiles of the patients and to correlate these profiles with the efficacy of their ongoing azidodeoxythymidine treatment (see Section 25, infra).

Using the improved assay format, paired samples of synovial fluid and serum were analyzed for several patients with rheumatoid arthritis. This data is presented in Table XVIII.

TABLE XVIII

DETECTION OF SOLUBLE CD4 IN PAIRED SYNOVIAL FLUID AND SERUM SAMPLES FROM INDIVIDUAL PATIENTS

| PATIENT | Sample[1] | Soluble CD4 (U/ml) + HA[2] | Soluble CD4 (U/ml) + IgG[3] |
|---|---|---|---|
| 1 | serum | 16 | 13 |
| | fluid | 42 | 36 |
| 2 | serum | 15 | 12 |
| | fluid | 64 | 57 |
| 3 | serum | 15 | 14 |
| | fluid | 44 | 39 |
| 4 | serum | 21 | 16 |
| | fluid | 103 | 96 |
| 5 | serum | 23 | 19 |
| | fluid | 66 | 59 |
| 6 | serum | 19 | 14 |
| | fluid | 41 | 37 |
| 7 | serum | 22 | 22 |
| | fluid | 78 | 84 |
| 8 | serum | 15 | 13 |
| | fluid | 80 | 73 |
| 9 | serum | 15 | 13 |

TABLE XVIII-continued
DETECTION OF SOLUBLE CD4 IN PAIRED SYNOVIAL FLUID AND SERUM SAMPLES FROM INDIVIDUAL PATIENTS

| PATIENT | Sample[1] | Soluble CD4 (U/ml) + HA[2] | Soluble CD4 (U/ml) + IgG[3] |
|---|---|---|---|
| 10 | fluid | 87 | 90 |
|  | serum- | 19 | 15 |
|  | fluid | 129 | 125 |

[1] Samples were obtained from the serum or synovial fluid of each patient.
[2] HA = heat aggregated IgG added to remove any false positive problems associated with occassional high RF (rheumatoid factor) containing samples.
[3] IgG = unaggregated IgG control to detect samples that may have had RF problems.

The above data indicates that with the increased sensitivity of the employed assay, it was possible to detect soluble CD4 levels in both serum and synovial fluid samples of rheumatoid arthritis patients. The levels observed in serum samples were within the normal range, however. Furthermore, the levels of soluble CD4 were elevated in synovial fluid samples relative to serum samples form 10 of 10 patients analyzed. This suggests a localized production and release of CD4 antigen.

Figure 2:
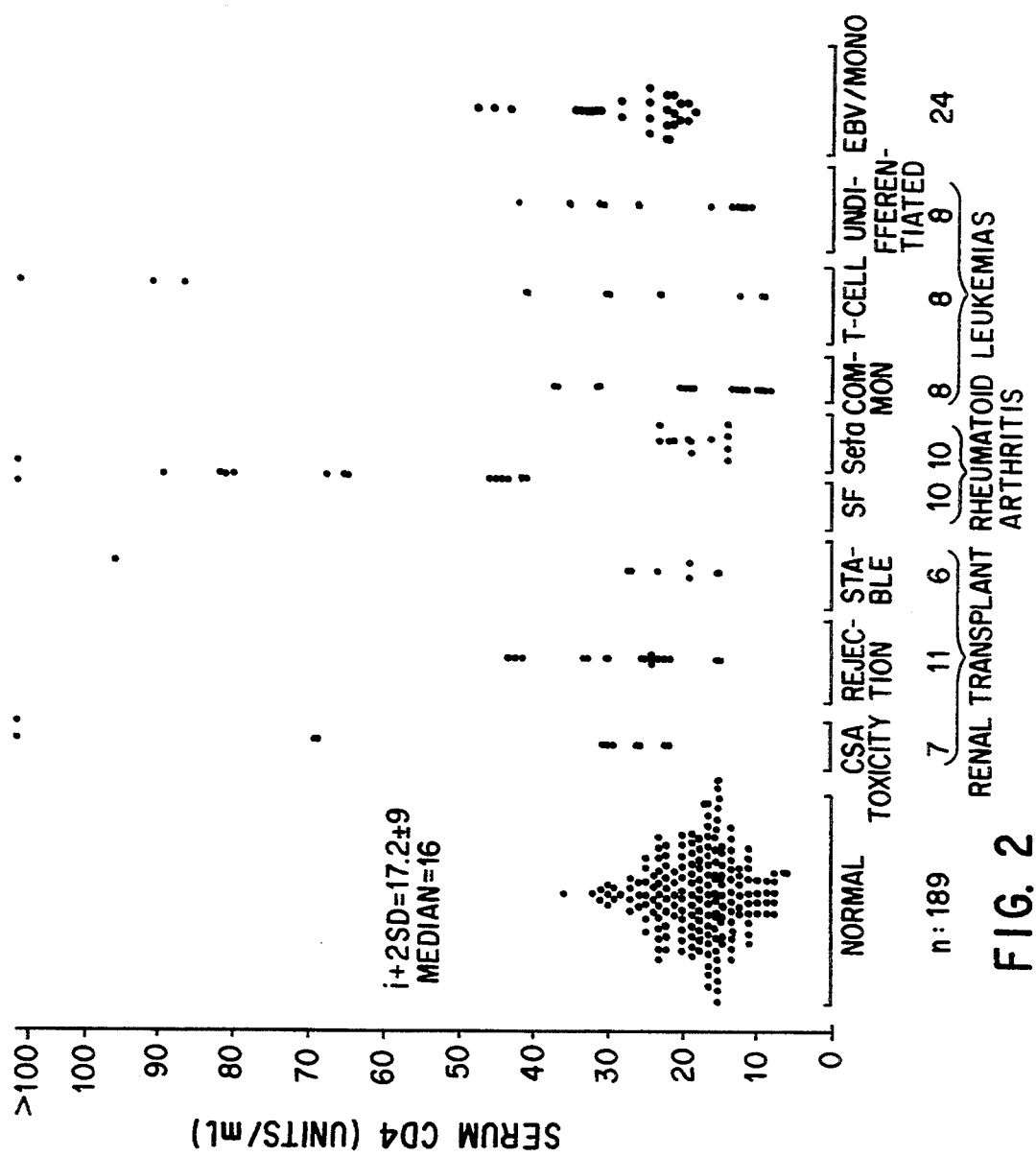
FIG. 2. Levels of soluble CD4 in sera of normal individuals and patients from a number of disease groups. The assay used was as described in Section 6.1.2.2 infra. SF: synovial fluid; EBV/mono: Epstein Barr Virus/mononucleosis.

Levels of soluble CD4 in sera of normal individuals and patients from a number of disease groups were measured, with the results shown in FIG. 2. Elevated levels of soluble CD4 were observed in renal transplant patients, synovial fluid of rheumatoid arthritis patients, in some patients with EBV infections, and in patients with various leukemias.

6.3. DISCUSSION

Assays have been described herein that allow the measurement of CD4 in a detergent solubilized membrane form, in a recombinant soluble form (genetically engineered to exclude the transmembrane region), and in a spontaneously released form from activated T cells. Nine different anti-CD4 antibodies, in a total of 63 different configurations (one configuration consisting of a single capture and a single detection antibody) were screened for suitability for detecting CD4 in cell lysates. Nine such suitable configurations were identified. Of these, only five configurations showed significant reactivity with soluble recombinant CD4. Three of these five configurations involved R2B7 as one of the antibodies. R2B7 when paired with 8F4 showed greatest sensitivity for detecting soluble CD4 both from recombinant and natural sources. The greatest ratio of signal from a soluble recombinant CD4 to signal from solubilized lysate CD4 is seen using 8F4 capture with R2B7 detection. This is roughly twice the ratio seen in the reverse configuration. It is possible that binding of one or more of the antibodies induces conformational changes in the molecule. This is supported by the observation that when IOT4 is used as a capture reagent, only solubilized lysate CD4 may be detected (using 8F4 or R2B7 detection), whereas when 8F4 or R2B7 are used as capture in combination with IOT4 as detection, soluble CD4 is preferentially detected over solubilized lysate CD4. Recombinant CD4 serves as a good model for released CD4 since those antibody combinations which work best with recombinant soluble CD4 also work best with the spontaneously soluble form of the molecule. Thus, selection of the antibodies and their configuration in the sandwich immunoassay is crucial to successful detection of released CD4.

Doumerc et al. (1986, 6th Intl. Congress of Immunology, Toronto, Ontario, Canada, Jul. 6–11, 1986, Abstr. 5.54.6, p. 708) have described an enzyme immunoassay based on the use of IOT4 as a capture and detection reagent to detect CD4 in serum. In our hands, this configuration works only to measure the membrane form of the molecule and fails to adequately measure the soluble recombinant or soluble spontaneously released form of the molecule described here. Doumerc et al. (id.) disclose increased serum CD4 during transient episodes of lymphocyte destruction. It is possible that the form of the molecule measured by Doumerc et al. represents a form still associated with pieces of membrane, not a truly soluble moiety. Such a membrane form will tend to aggregate or associate into micelles or vesicles, thus rendering it capable of detection in a sandwich immunoassay using the same antibody as both capture and detection reagent. Since soluble CD4 is not known to exist in multimeric structures, in the absence of repeating epitopes, the same antibody cannot be used as both capture and detection reagent for assay of soluble CD4. Doumerc et al. further suggest that the CD4 they measure correlates with total CD4 cell pool. We suggest that CD4 release, like CDS, is rather a function of activation of cells. This is supported by the kinetics of released CD4 observed during in vitro stimulation. Thus, the molecule described by Doumerc is significantly different from the molecule described herein.

CD4 release may be a function of the type and pathway of activation. Phytohemagglutinin and T3 stimulation both resulted in a release of small amounts of CD4. Stimulation with phorbol esters, known to cause phosphorylation and internalization of CD4, or with ionophores, resulted in significantly less released CD4 than did PHA stimulation, despite intense cellular activation. The kinetics of CD4 release were also significantly different between cells stimulated by phorbol esters and those stimulated by PHA. Release can also not be attributed to simple membrane turnover. No CD4 is released by resting cells in vitro.

Cloned IL-2 dependent CD4+ T cells or T cell lines containing CD4+ cells all showed detectable soluble CD4 in their culture supernatants. CD8+ cells showed only soluble CD8. Thus, the released molecules are an accurate reflection of the cell surface phenotype of the cells. No correlation was observed between levels of soluble CD4 and the number of cells.

Low levels of CD4 were seen in sera from normal individuals. Elevated soluble CD4 was observed in certain individuals with EBV infection, lung cancer and with T cell leukemias, and correlated overall with the stage of disease (FIG. 22, 23). Elevations in CD4 antigen levels were also observed in disorders due to HIV infection, and in some synovial fluid, but not sera, from patients with rheumatoid arthritis. Elevations were observed in certain patients on IL-2 therapy where there is activation of CD4+ as well as CD8+ cells and natural killer cells. Finally, elevations were observed in sera of some patients undergoing renal allograft rejection or cyclosporin A toxicity. Soluble CD4 levels may thus be of value in the diagnosis and monitoring of a pathologic event.

The relationship between spontaneously released CD4 and membrane CD4 can be determined from patterns of antibody reactivity. If the spontaneously released material were identical to the cell-surface polypeptide, it should behave in the assays, which have detergent incorporated into them, like solubilized CD4 in cell lysate. If they are more analogous to the recombinant truncated version of CD4 they should behave like it. The latter is the case; that is, those antibody pairs which afford suitable detection of solubilized lysate CD4, but not recombinant soluble CD4, yielded poor detection of the soluble CD4 from T cell culture supernatant, whereas those antibody pairs showing optimal reactivity with recombinant soluble CD4 also reacted optimally with the released material. It is clear from antibody reactivity patterns that the released form of the CD4 antigen differs significantly from the membrane form.

A key element in deriving a successful sandwich immunoassay for the detection of soluble CD4 was the strategy employed in antibody selection. A readily available model source of soluble CD4, recombinant truncated CD4, was used in a screening procedure to select antibodies with a preferential ability to identify the released form of the molecule. Using this criteria, a pair of antibodies was selected that could detect spontaneously released CD4 in sera and in culture supernatants. This strategy may be widely applicable to the detection and discovery of other released molecules.

7. TOTAL CD4 ANTIGEN AND ASSAY

First, a study was conducted to determine if detergent solubilized whole blood would yield measurements of total CD4 which correlated with the absolute number of CD4+ T cells/mm$^3$. After the properties of the total CD4 assay were established using healthy donors, further study was conducted to establish a relationship between the total CD4 as measured in the ELISA to the total number of CD4+ T cells in HIV infected individuals.

In an HIV-infected individual, the most useful single prognostic indicator for progression to overt AIDS is the absolute number of CD4+ T cells/mm$^3$ of whole blood. Currently, accurate measurement of CD4+ T cells requires the use of a flow cytometer, both costly and not widely available. In addition, federal guidelines define eligibility for AZT administration to AIDS infected individuals solely on the basis of the CD4+ T cell count (a T cell count which drops below 500 CD4+ T cells/mm$^3$) regardless of symptomology. However, the costly and largely unavailable flow cytometer leaves a large population of clinicians and patients without the means of proper immune status evaluation and therefore AZT treatment. Thus, the development of an assay which correlates total CD4 values with the absolute CD4+ T cell number is of great value in the treatment and monitoring of AIDS infected individuals.

Such a total CD4 ELISA has been developed. It demonstrates a statistically significant correlation between the measurement of total CD4 levels and total CD4+ T cell/mm$^3$ of whole blood in both HIV-infected individuals and normals. Uses of this total CD4 assay include improved monitoring and therapeutic intervention in HIV-infected individuals. It is economic, safe, and batch samples can be analyzed. It will be more widely available to clinicians than flow cytometric based procedures. It represents a significant improvement over the current method of flow cytometric analysis of CD4+ T cell to monitor diseases such as AIDS.

7.1. MATERIALS AND METHODS

Patient samples included 26 sero-positive HIV-infected individuals and 13 healthy adult volunteers.

Whole blood samples were prepared from two study groups as follows. Blood was obtained by venipuncture into a blood collection tube. 100 μl of anticoagulated blood was removed from the blood collection tube and mixed with 20 μl of 6× detergent (6% triton X-100, 6% NP-40 in distilled water) in a 12×75 mm glass tube. This mixture was then incubated for one minute at room temperature. After one minute the whole blood detergent lysate was either used in the total CD4 assay or stored at −70° C. until assayed. Samples stored at −70° C. were allowed to thaw at room temperature before use.

7.2. TOTAL CD4 ASSAY

Total CD4 was measured in the detergent treated whole blood samples using the commercially available CELLFREE® CD4 assay kit (T Cell Sciences, Inc. Cambridge, Mass., Section 6, supra) using a one-step, three hour format. Briefly, each well of a 96 well microtiter well plate was coated with 100 μl of the murine anti-CD4 coating antibody in phosphate-buffered saline (PBS) overnight at 4° C. Any remaining protein-binding sites were blocked with 300 μl per well of blocking buffer (0.5% casein, 0.008% NP-40, 0.005% EDTA in PBS) for 2 hours at 37° C. The wells were washed three times with 350 μl per well of wash buffer (PBS, ph 7.4, with 0.05% Tween 20). After aspirating the final wash buffer from the wells, 50 μl of horseradish peroxidase (HRP) conjugated murine monoclonal anti-human CD4 antibody (in PBS with 15% FCS and 0.15% NP-40) and 50 μl of sample or standard were added to each well of the microtiter plate in duplicate. Sample volumes were maintained at 50 μl by the addition of sample buffer (1% bovine serum albumin, phosphate buffered saline, 0.25% NP-40 and 0.01% thimerosal). The combined volume of sample and HRP conjugated antibody was 100 μl. After washing the plate as described above, 100 μl of OPD substrate (OPD tablets, BioDesign Intl, Catalogue #A45104T, dissolve 1 tablet in 4 ml citrate buffer-peroxide, BioDesign Intl, Kennebunkport, Me., Catalog number A45105B) was added to all the wells and incubated for 30 minutes at room temperature. At the end of this last incubation, 50 μl of 2N $H_2SO_4$ was added to each well to stop the reaction and absorbance of each well was read at 490 nm. Results were plotted as values obtained for each sample at O.D. 490 against total CD4+ cells/mm$^3$ or sample volume. Correlation coefficients were calculated using linear regression analysis.

Whole blood samples from normal and HIV-infected patients were assayed for absolute CD4+ T-cells/mm$^3$ using the formula:

Abs. CD4+ T cells/mm$^3$=WBC ×% Lymphocyte ×% CD4+ T cells WBC (White blood cell count) was determined using a hemacytometer. % Lymphocyte was determined by a differential count, and %CD4+ T cells were determined using the Ortho cytoflurograph II and Leu-3a (anti-CD4) fluorescein-conjugated antibody (Becton Dickinson, Mountain View, Calif.)

7.3. RESULTS

One assay configuration used to measure total CD4 in samples of whole blood was the CD4 assay described supra in Sections 6 and 7.2. Samples of whole blood were treated with a 6× detergent solution using a ratio of 20 μl detergent to 100 μl anticoagulated whole blood. Serial dilutions were made of these samples to produce a series of samples containing decreasing amounts of total CD4. These samples were then analyzed in the CD4 assay to determine which dilutions produced values that were linear with sample dilution. As the assay configuration became saturated with excess CD4, the optical density values representing total CD4 values became nonlinear.

Figure 3:
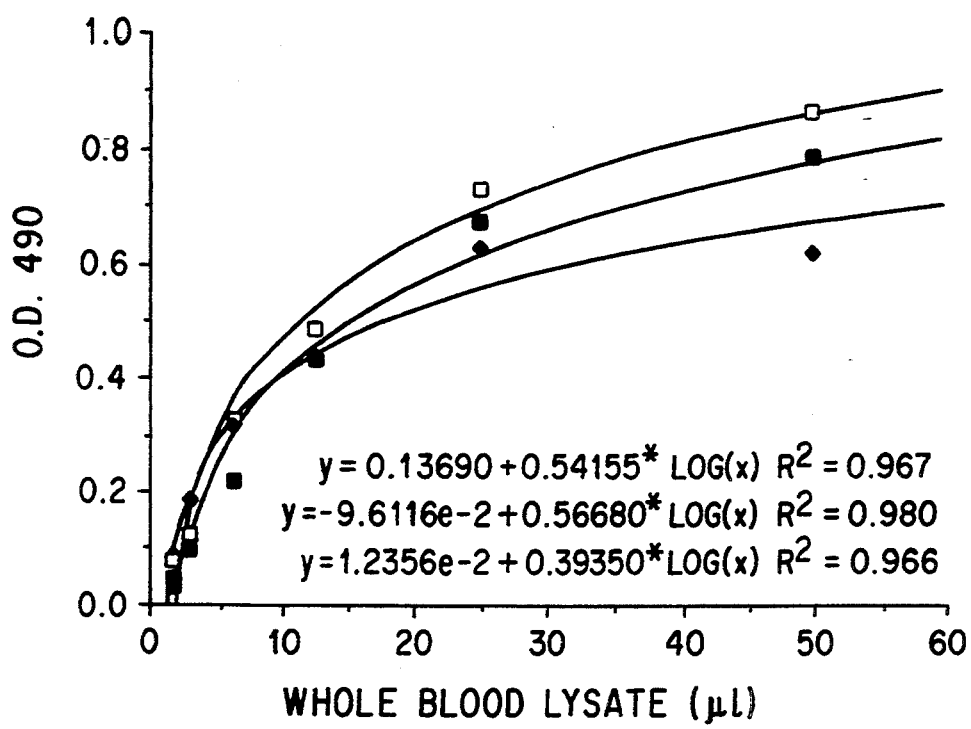
FIG. 3. The detection of total CD4 from whole blood using the CELLFREE CD4 assay kit. The three curves represent the detection of total CD4 (O.D. 490) from the blood of three normal individuals following serial dilutions of the samples.

The results of this experiment can be seen in FIG. 3. Total CD4 preparations made from three healthy volunteers were run at several different sample dilutions (1:2 dilutions). Sample volumes were maintained at 50 μl by dilution into sample buffer. Linear regression analysis demonstrated that samples containing less than 20 μl and preferably 5-10 μl of detergent treated whole blood are optimal for total CD4 measurement as they fall within the linear range. Samples containing greater than 20 μl of whole blood saturated the assay and total CD4 could not be accurately determined.

The ability of an anti-CD4 antibody to block the total CD4 signal detected in whole blood samples of three normal controls is presented in Table XIX. The assay was run as described in Section 7.2 supra. except before adding the HRP-conjugated murine anti-CD4 monoclonal antibody to the wells, 5 μl of the unconjugated murine anti-CD4 monoclonal antibody used in the coating procedure was added to the wells, followed by the HRP-conjugated antibody. The unconjugated antibody was able to block CD4 detection by 50%, 51% and 51% in samples #1, 2, and 3, respectively, at the level of competing antibody used. This demonstrates the specificity of the assay to detect total CD4. Other proteins released during detergent lysis of the whole blood samples (such as hemoglobin) do not interfere with the assay.

TABLE XIX

SPECIFICITY OF TOTAL CD4 DETECTION IN DETERGENT SOLUBILIZED WHOLE BLOOD

| | O.D. 495 | | |
|---|---|---|---|
| sample # | 10 μl* | 10 μl + anti-CD4** | % inhibition |
| 1 | 0.433 | 0.216 | 50% |
| 2 | 0.928 | 0.472 | 51% |
| 3 | 0.833 | 0.422 | 51% |

*10 μl of detergent treated whole blood prepared from normal uncoagulated whole blood
**5 μl of the anti-CD4 coating antibody from the CD4 assay was also added to compete for binding.

Figure 4:
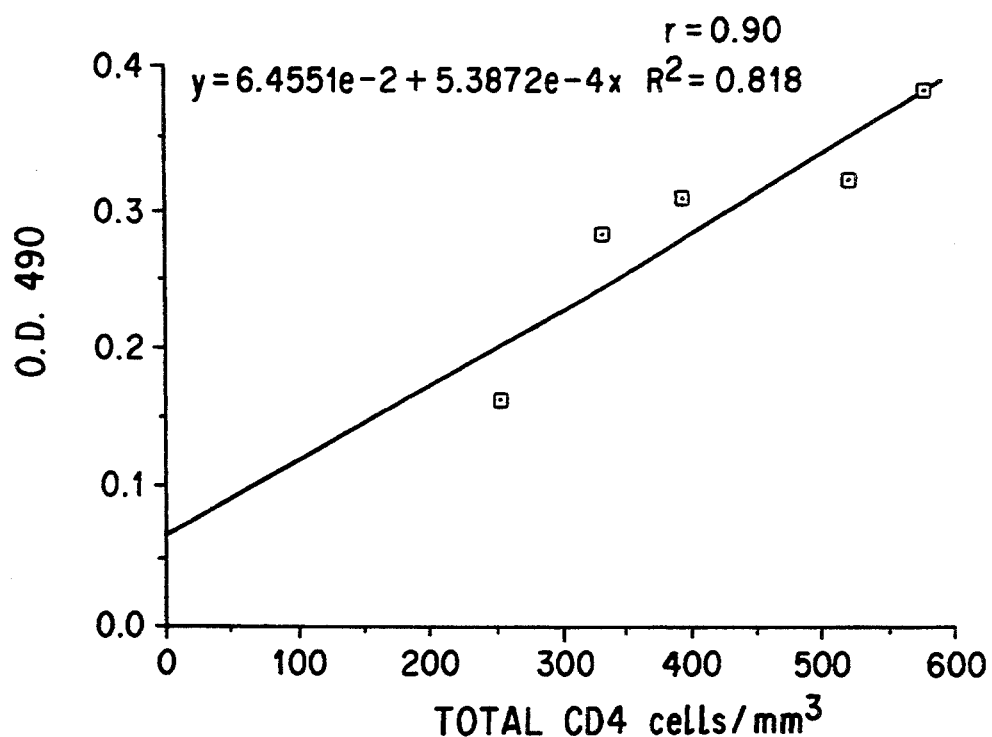
FIG. 4. The correlation between total CD4 as measured in a CD4 immunoassay and the total number of CD4 cells/mm$^3$ of blood. CD4 (O.D. 490) was measured from 10 ul of a whole blood lysate from five different normal individuals using the CELLFREE CD4 assay kit. Total CD4/mm$^3$ was measured from the blood samples of the five normal individuals three days after determination of total CD4 from the samples. Such total CD4 cells/mm$^3$ of blood appear lower than expected for normal individuals.

Data in FIG. 4 demonstrates a statistically significant correlation between CD4 measured in whole blood samples and the total number of CD4+ cells/mm³ of blood (r=0.904). Samples measured in this assay contained 2.5 μl of detergent treated whole blood from a total of five normal controls. The normal range of CD4 cells/mm³ is 800-1000 CD4+ cells/mm³ (The normal values in this assay appear lower than usual due to the fact that the WBC count used to determine the number of CD4 cells/mm³ was performed on the uncoagulated blood samples three days after the CD4 assay was run). The relationship between total CD4 detected in the assay and the total CD4+ cells/mm³ for each individual was determined by linear regression analysis and a statistically significant r value of 0.904 was obtained.

The total CD4 values of HIV-infected individuals and normals were determined using the whole blood sample preparation and CD4 assay on two separate occasions. The result of these experiments are presented in FIGS. 5 and 6. Ten μl of whole blood samples from either the disease group or control group were used to determine the total CD4 values. The total CD4+ cells/mm³ cells was determined on fresh uncoagulated blood samples on the day of the CD4 assay.

Figure 5:
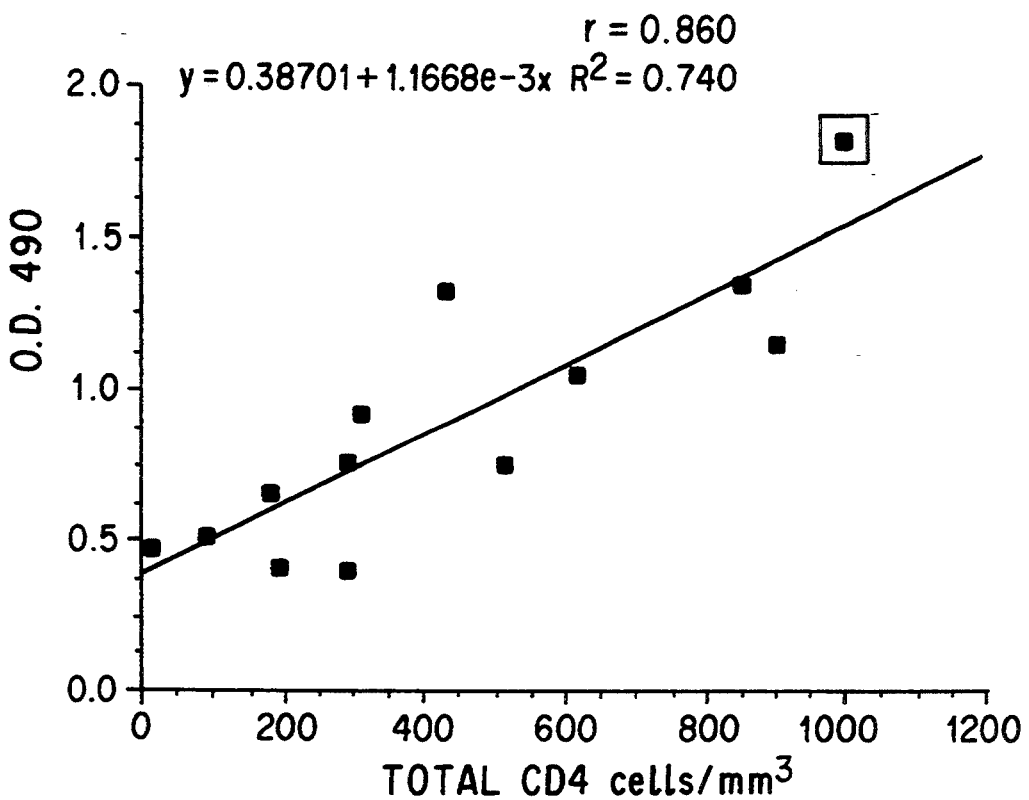
FIG. 5. The correlation between total CD4 measured from the whole blood lysate of HIV-infected individuals and one normal control and total CD4 cells/mm$^3$ of blood. HIV-infected individuals are represented by a single square and the normal by the double squares.
Figure 6:
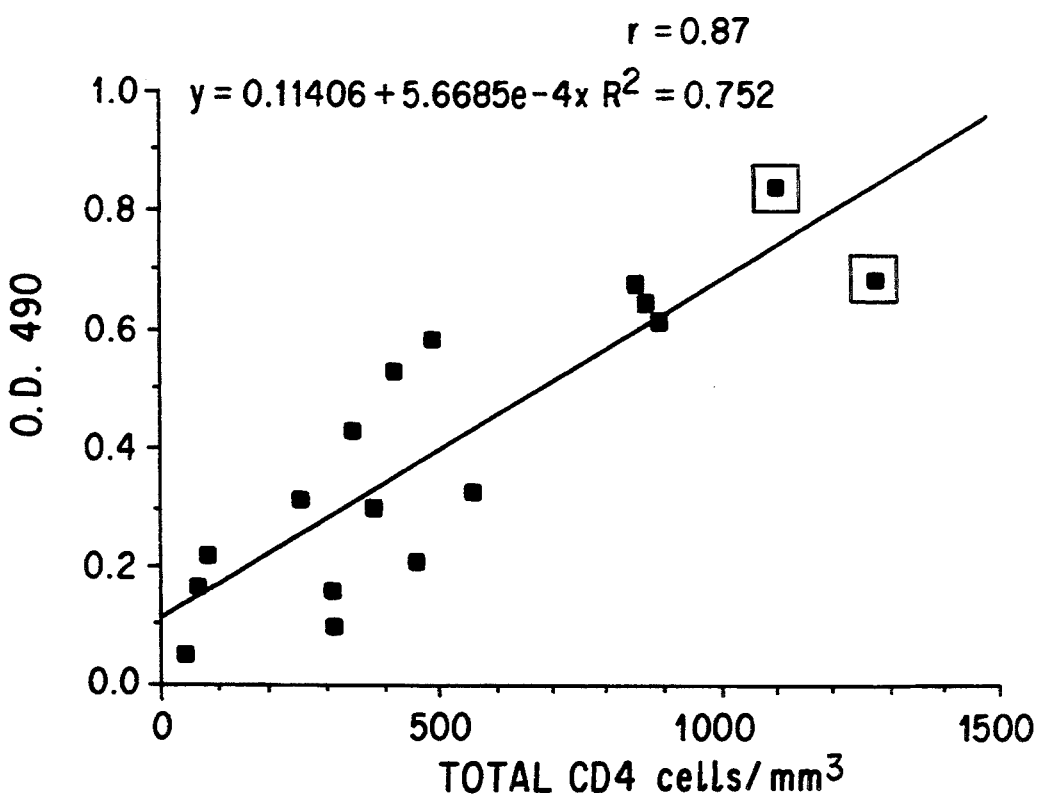
FIG. 6. The correlation between total CD4 measured from the whole blood lysates of HIV-infected individuals and normal controls and total CD4 cells/mm$^3$ of blood. HIV-infected individuals are represented by a single square and the normal by the double squares.

Both FIGS. 5 and 6 demonstrate a statistically significant correlation between total CD4 measured in the assay and the total CD4+ cells/mm³ for both the HIV-infected group (single squares) and the control group (double squares) (r=0.860 and 0,867 for FIGS. 5 and 6, respectively). Thus, the measurement of total CD4 from the detergent lysates of whole blood accurately reflects the absolute number of CD4+ T-cells in whole blood.

As described herein, we have developed a method that measures the level of total CD4 in a patient sample. Whole blood samples were detergent solubilized and assayed using a CD4 Assay Kit in a one-step, three hour format. It was demonstrated that total CD4 could be detected in whole blood samples of normal individuals by a simple detergent lysis step and CD4 immunoassay. Optimal detection could be measured using 10 μl or less of detergent solubilized whole blood samples. Accurate and reproducible measurements can be detained from 2.5 μl to 5 μl of whole blood. The detection of total CD4 was specific as a murine anti-CD4 monoclonal antibody was capable of blocking the total CD4 signal when added to the assay format. The release of other proteins during detergent lysis of whole blood did not interfere with the specificity of the assay. It was further demonstrated that the total CD4 values obtained in the ELISA correlated with the total CD4+ T cells/mm³ in the whole blood of normal donors (r=0.9).

A comparison between the total CD4 obtained in the CD4 ELISA and the total number of CD4+ T Cells/mm³ of whole blood yielded a statistically significant correlation in both HIV-infected individuals and normals. This comparisons was determined on two separate occasions using two different groups of HIV-infected individuals and normals. Both comparisons yielded statistically significant correlations between total CD4 values and total CD4+ T cells/mm³ (r=0.86 and 0.87).

8. SOLUBLE CD8 DETECTION IN PATIENTS

The following sections describe antibodies and assays that can be used to detect soluble CD8 antigen in patients.

8.1. MONOCLONAL ANTIBODIES

Anti-CD8 monoclonal antibody 5F4 was generated according to Reinherz et al. (1979, Proc. Natl. Acad. Sci. U.S.A. 76:4061-4065) by immunizing BALB/c mice with a human T cell line (Jurkat). Monoclonal antibody 5F4 recognizes an epitope on CD8 that is different from the epitope on CD8 which is recognized by mAb OKT8.

8.2. SOLUBLE CD8 ASSAY

Soluble CD8 was detected in samples using the procedure outlined below:
(a) Polystyrene microtiter wells (Flow Laboratory) were coated overnight at 4° C. with 100 μl of an anti-CD8 murine monoclonal antibody (2.5 ug/ml) of mAb OKT8 (Ortho Diagnostics, Raritan, N.J.) in PBS.
(b) Coating solution was discarded and wells were blocked for 1-2 hours at room temperature with 300 μl of 1% BSA in Tris-buffered saline containing 25 mM Tris pH 7.4 in 0.05% Tween 20 and 0.15M sodium chloride (NaCl).
(c) Wells were washed 3 times with 10 mM Tris, 0.05% Tween 20, pH 8.0 (Tris washing solution).

(d) 10 μl sample was added per well, followed by 90 μl diluent containing 50% FCS in Tris-buffered saline and 0.4% NP-40 (Sigma). Wells were incubated 2 hours at 37° C.

(e) Wells were washed 3 times with Tris washing solution.

(f) 100 μl of horseradish peroxidase conjugated anti-CD8 murine monoclonal antibody (0.2 μg/ml mAb 5F4) in 50% FCS, 25 mM Tris pH 7.4, 0.15M NaCl and 0.1% NP-40 was added to each well and incubated 2 hours at 37° C.

(g) Wells were washed 4 times with Tris washing solution.

(h) 100 μl of 0.2% o-phenylenediamine (OPD) and 0.015% of $H_2O_2$ in citrate-phosphate buffer was added per well. Plates were incubated for 30 minutes at room temperature.

(i) 50 μl of 2N $H_2SO_4$ was added to each well and the absorbance of each well was measured at 490 nm in a microtiter plate reader.

8.3. CD8 CONTROL STANDARDS

The supernatant of a tissue culture line (Jurkat) was used as the standard. The measured value was assigned a reference number of 2000 units/ml. The culture supernatant consisted of RPMI-1640 medium containing 10% FCS and 100 units of penicillin-streptomycin.

8.4. ENZYME IMMUNOASSAY FOR THE QUANTITATION OF CELL-FREE HUMAN T CELL CD8-LIKE MOLECULE

Using two monoclonal antibodies directed against distinct epitopes on the CD8 antigen, a human suppressor/cytotoxic T cell marker, we have developed a sensitive quantitative enzyme immunoassay for measuring the cell free form of a human T cell CD8-like antigen. Elevated levels of this antigen are observed in a number of diseases and conditions including certain leukemias, allograft transplantation, and autoimmune diseases such as rheumatoid arthritis and lupus. In longitudinal patient studies, increases in the serum level of cell-free CD8 are seen in a different time frame when compared to the expression of soluble interleukin-2 receptor (IL2R). In certain instances, elevations of cell-free CD8-like molecules are preceded by several days with elevations in serum IL2R levels. Increased levels of this cell-free CD8-like molecule may indicate the involvement of significant numbers of suppressor/cytotoxic T cells with a specific pathological event, distinct from immune activation as measured by a rise in cell-free IL2R. The presence of cell-bound CD8 and IL2R molecules is typically measured by cell surface staining. These cell-free assays may provide a more thorough understanding of certain immunological disorders.

The assay used for CD8 was a sandwich enzyme immunoassay, as described in Section 8.2, supra. An anti-CD8 mAb (mAb 1) was coated onto a solid substratum, e.g. microtiter wells. CD8 in the sample binds to the antibody-coated well; unreacted sample components are washed away. An enzyme-conjugated, second anti-CD8 mAb (mAb 2), recognizing a different epitope than that of mAb 1, binds to the CD8 antigen captured by the first antibody and completes the sandwich. Unbound mAb 2 was removed by washing. A substrate solution was added to the wells, and a colored product formed in proportion to the amount of CD8 present in the sample. The reaction was terminated by stop solution and the absorbance was measured. A standard curve is prepared from CD8 standards (See Section 8.3, supra). Unknown values were determined from the standard curve.

8.4.1. EVALUATION OF ANTI-CD8 MONOCLONAL ANTIBODIES AS A CAPTURE ANTIBODY

Various monoclonal antibodies (mAbs) directed against the CD8 antigen were tested for their suitability as a capture antibody in an enzyme immunoassay employing anti-CD8 mAb 5F4 as detection antibody (mAb 2).

Plates (Flow microstrips, Flow Laboratory, McClean, Va.) were coated overnight with 2.5 μg/ml of capture antibody. Non-reactive sites were blocked the next day with a solution containing 1% BSA in 0.15M NaCl, 0.025M Tris-Cl (pH 7.4), 0.01% thimerosal, 0.05% Tween 20. 100 μl sample was added, consisting of CD8-containing Jurkat cell supernatant, diluted 1:4 in 25% fetal calf serum, 0.25% Nonidet P-40 (NP-40) in Tris-buffered saline. After incubation for 90 minutes at 37° C., the plates were washed with 10 mM Tris, 0.05% Tween 20, pH 8.0. 100 μl of horseradish peroxidase (HRP)-conjugated mAb 5F4 (at 1:5000 dilution of a 1 mg/ml stock) in 25% fetal calf serum, 0.25% NP-40 in Tris-buffered saline was added. Plates were incubated for 90 minutes at 37° C. and washed as above. 100 μl of 0.2% o-phenylenediamine was added in 0.015% $H_2O_2$, and incubated for 30 minutes at room temperature, after which absorbance was read at 450 nm. Results are as shown in Table XX.

TABLE XX

| EVALUATION OF ANTI-CD8 MONOCLONAL ANTIBODIES AS A CAPTURE ANTIBODY[1] | | |
|---|---|---|
| Capture Antibody | Ability to Compete Binding of mAb 5F4 to CD8 | $OD_{450}$[2] |
| B98.1.1 | Partial | 0.028 |
| B116.1.1 | Yes | 0.027 |
| B99.1.1 | No | 0.039 |
| OKT8 | No | 0.413 |
| 4C9 | No | 1.106 |
| 5F4 | Yes | 0.042 |
| 62EC[3] (control) | Yes | 0.042 |

[1] With HRP-conjugated mAb 5F4 as detection antibody
[2] Readings at or below 0.042 (negative control) are considered negative
[3] Negative control mAb, directed against Keyhole limpet hemocyanin (Pacific Biolabs, CA)

The results of binding competition assays to mAb 5F4 are also shown in Table XX. These assays were carried out using the same protocol described supra, except that the capture antibody was OKT8 and the detection antibody was a mixture of 50 μl competing antibody (1 μg/ml) plus 50 μl HRP-conjugated mAb 5F4 (at 1:2500 dilution of a 1 mg/ml stock).

As shown in Table XX, the seven mAbs tested as capture antibodies can be classified into three groups, based on their ability to competitively inhibit binding of mAb 5F4 to CD8 antigen. As expected, use of the 5F4 mAb as both capture and detection antibody does not work (since capture antibody 5F4 competes out detection antibody 5F4 binding). Surprisingly, among the group of mAbs which did not competitively inhibit binding of 5F4 to CD8, 4C9 worked best, giving the highest assay results, followed by OKT8, whereas B99.1.1 was negative. Thus, it is not obvious, even based upon competition ability, to predict which anti-CD8 monoclonal antibodies will work in a sandwich immunoassay.

A comparison of the serum CD8 levels measured by use of mAb OKT8 versus mAb 4C9 as capture antibody was also done. mAb 5F4 was used as a detection antibody. The results, shown in Table XXI, demonstrate a greater CD8 detection level using 4C9 as capture antibody in the vast majority of cases.

TABLE XXI

COMPARISON OF CD8 LEVELS USING TWO DIFFERENT ANTI-CD8 CAPTURE ANTIBODIES[1]

| PATIENT GROUP | U/ml MEASURED USING OKT8 CAPTURE | MEASURED USING 4C9 CAPTURE |
|---|---|---|
| Normal | 96 | 143 |
| | 122 | 207 |
| | 211 | 211 |
| | 52 | 72 |
| | 146 | 209 |
| | 59 | 147 |
| | 20 | 72 |
| | 14 | 65 |
| | 76 | 270 |
| | 33 | 270 |
| | 52 | 261 |
| | 76 | 329 |
| | 63 | 394 |
| | 193 | 724 |
| | 14 | 96 |
| | 91 | 252 |
| | 33 | 188 |
| | 269 | 858 |
| | 57 | 292 |
| | 22 | 226 |
| Renal | 237 | 721 |
| Transplant | 229 | 620 |
| Patients | 393 | 1249 |
| | 303 | 687 |
| | 231 | 613 |
| | 488 | 1464 |
| | 824 | 1665 |
| | 351 | 1176 |
| | 381 | 1603 |
| | 432 | 1002 |
| | 202 | 171 |
| | 198 | 131 |
| | 455 | 248 |
| | 502 | 361 |
| | 98 | 110 |
| | 133 | 190 |
| | 324 | 377 |
| | 144 | 319 |

[1]With anti-CD8 mAb 5F4 as detection antibody

9. SERUM CD8 LEVELS IN EVALUATION OF DISEASES AND DISORDERS

A number of diseases and disorders can be staged or diagnosed by measuring serum soluble CD8 levels in patients. Examples are described in the subsections below.

9.1. DIFFERENTIAL DIAGNOSIS OF RHEUMATOID ARTHRITIS

Figure 7:
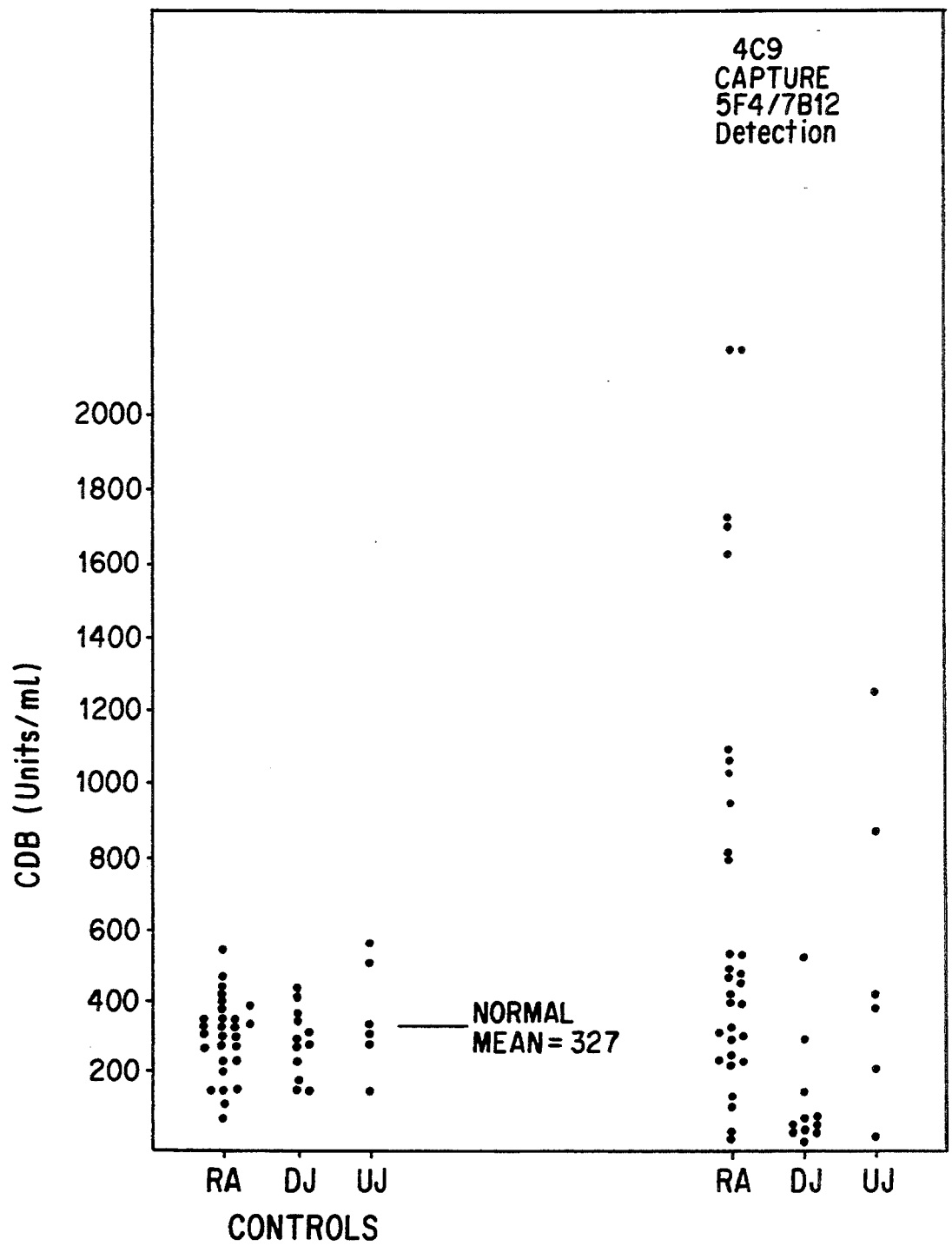
FIG. 7. Distribution of soluble CD8 levels in serum and synovial fluids among patients with rheumatoid arthritis (RA), degenerative joint disease (DJ) and unclassified joint disease (UJ). Data at left indicate soluble CD8 levels in control healthy patients for each series of assays.

Using the CD8 sandwich enzyme immunoassay described above one can distinguish rheumatoid arthritis from other joint diseases (FIG. 7). The results shown in FIG. 18 are based on the level of serum or synovial fluid CD8 concentration, measured using mAb 4C9 as capture antibody, and mAb 5F4 as detection antibody.

9.2. SERUM CD8 LEVELS IN A RENAL ALLOGRAFT RECIPIENT

Patient A was the recipient of a HLA nonidentical renal allograft from cadaver. The patient was transplanted on May 23, and maintained on cyclosporin A (CsA). From May 23 through May 31, the patient experienced CsA toxicity and some early rejection. On June 28, a rejection episode was diagnosed (based on a rise in creatinine level, and the patient was administered OKT3 mAb, at 5 mg doses intravenously four times a day, through July 7. On July 8, the creatinine level had decreased, and the patient had entered the process of recovery. On July 18, there was another rise in creatinine level that was treated by administration of prednisone, which resulted in a decrease in the creatinine level until August 26, at which time another dose of prednisone was administered.

Figure 8:
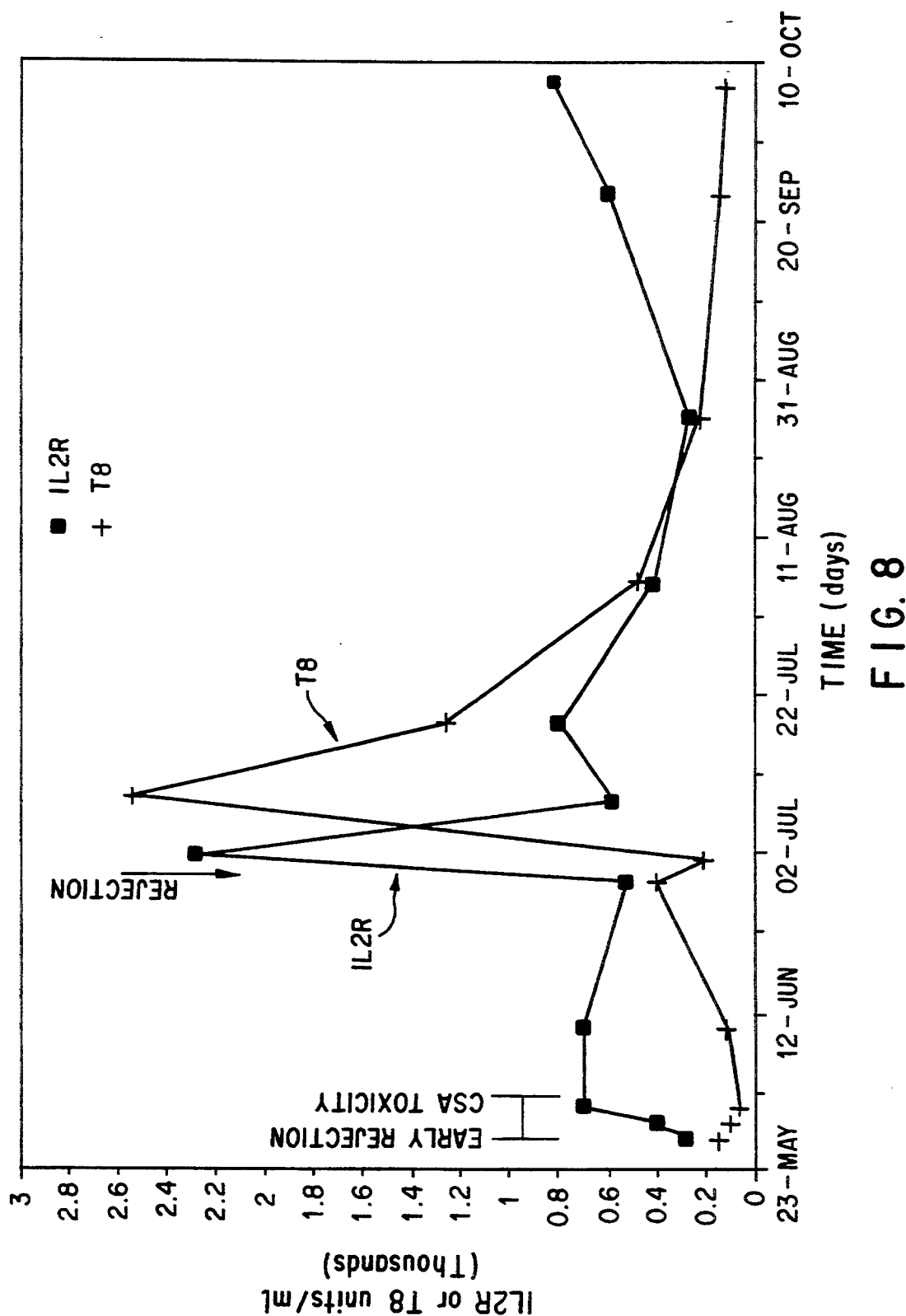
FIG. 8. Monitoring of a renal transplantation patient for serum CD8 and serum IL2R. Serum levels of either soluble IL2R or soluble CD8 are plotted against time. Episodes of CsA toxicity and rejection are indicated.

IL2R and CD8 levels in the patient serum were measured at suitable intervals from May 23 (transplant date) on, and are shown in FIG. 8 which shows a peak in serum CD8 levels after a rejection episode (but not after an episode of CsA toxicity). This is suggestive of a role for measurement of serum CD8 levels in the monitoring and differential diagnosis of renal transplant.

9.3. SERUM CD8 LEVELS IN CHILDREN WITH NON-HODGKIN'S LYMPHOMA

CD8 levels were measured in the serum of the children with non-Hodgkin's lymphoma (NHL) or B-cell acute lymphoblastic leukemia (ALL).

Figure 9:
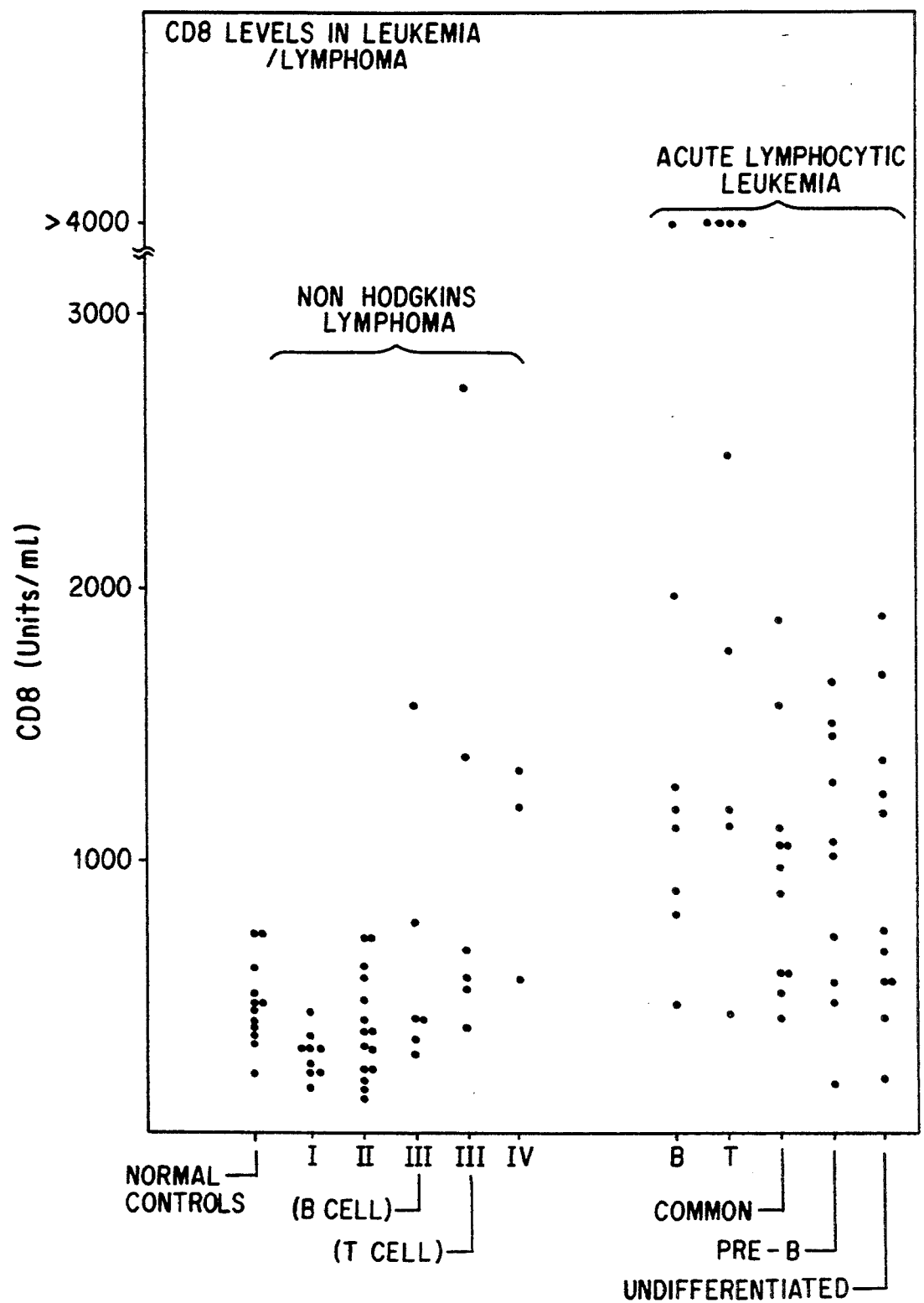
FIG. 9. Distribution of serum CD8 levels in children with non-Hodgkins lymphoma (NHL) and acute lymphoblastic leukemia (ALL). CD8 antigen was detected using mAb 4C9 as capture reagent and mAb 5F4/7B12 as detection reagent in a sandwich immunoassay.

The enzyme sandwich immunoassay, described above was used, with anti-CD8 mAbs 4C9 and 5F4 as the capture and detection antibodies, respectively. The results shown in FIG. 9 demonstrate that a detectable increase in the level of serum CD8 antigen in patients appears to be related to advanced disease and a poor outcome.

9.4. CD8 LEVELS IN INFECTIOUS DISEASE

Figure 10:
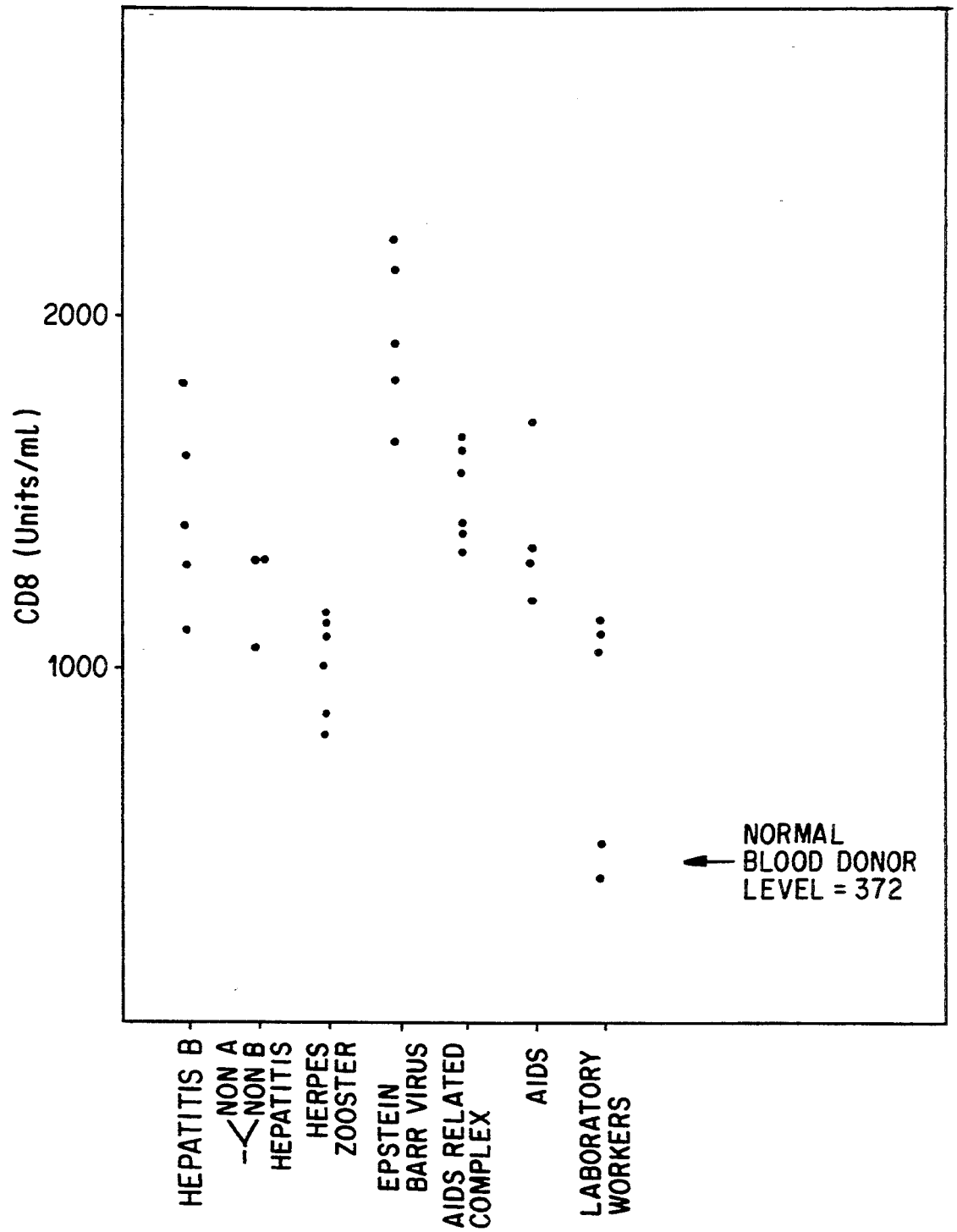
FIG. 10. Distribution of serum CD8 levels in patients with infectious disease. CD8 antigen was detected using mAb 4C9 as capture reagent and mAb 5F4/7B12 as detection reagent in a sandwich immunoassay.

The enzyme sandwich immunoassay, as described in Section 8.2., was used to measure CD8 levels in the serum of patients with an infectious disease. Anti-CD8 mAbs 4C9 and 5F4 were used as the capture and detection antibodies, respectively. The results, shown in FIG. 10, demonstrate an elevated level of the CD8 antigen, particularly in patients with Hepatitis B, Epstein Barr virus, AIDS related complex, and AIDS disorders.

9.5 SOLUBLE CD8 LEVELS AS A MEASURE OF THE IMMUNE RESPONSE TO DISEASE

In the example herein (Carrabis, S., et al., 9th Ann. European Immunology Mtg., Sep. 14–17, 1988, Rome Italy, poster presentation), we describe the results obtained using a sandwich enzyme immunoassay (CELL-FREE®T8 Test Kit, T Cell Sciences, Inc., Cambridge, Mass.) to measure soluble CD8 in cell culture supernatant and in patient sera.

The assay used has a range of 0–2,000 U CD8/ml of fluid and a sensitivity of 50 U/ml. No interference was seen in serum samples exhibiting high levels of protein, lipid, bilirubin, or hemoglobin.

The levels of released T8/CD8 measured by the ELISA assay were shown to correlate with the level of activation of CD8+ cells in vitro and in patients with EBV+ mononucleosis, a highly disseminated disease. The normal range of released T8/CD8, determined in 196 healthy individuals, was determined to be 138–533 U/ml.

The material reactive in the CD8 immunoassay was shown to be specifically released by CD8+ cell lines. The form of CD8 found in culture supernatant appeared to be a 52 kD homodimer, which is smaller than the 64 kD membrane bound molecule.

Levels of soluble CD8 were proportional to the degree of cellular activation, as measured by dual color immunofluorescence using fluorescent-tagged anti-CD8 and anti-HLA-DR antibodies, in PHA and anti-T3 antibody-stimulated peripheral blood mononuclear cell cultures.

In EBV-induced mononucleosis, changes in the levels of soluble CD8 paralleled changes in the proportion of peripheral T cells that were CD8+/HLA-DR+.

10. SERUM CD8 ANTIGEN AND INTERLEUKIN-2 RECEPTOR LEVELS IN CHILDHOOD HODGKIN'S DISEASE

We determined pre-treatment serum levels of soluble CD8 antigen and soluble IL2R in 90 children with newly diagnosed Hodgkin's disease. Our results (Table XXII) demonstrate that measurements of soluble CD8 antigen or IL2R can be used in the staging of Hodgkin's disease, that an increase in both soluble CD8 and IL2R is predictive of treatment failure, and that soluble CD8 levels can be relied on for monitoring treatment outcome.

TABLE XXII
LEVELS OF SOLUBLE CD8 AND SOLUBLE IL2R IN SERA OF CHILDREN WITH HODGKIN'S DISEASE

| Disease Characteristics | Soluble CD8 (U/ml) | Soluble IL2R (U/ml) |
|---|---|---|
| Stage I or II | 477 | 1098 |
| Stage III or IV | 675 | 3195 |
|  | p = 0.003 | P = 0.0001 |
| B symptoms | 622 | 3262 |
| All others | 494 | 999 |
|  | p = 0.005 | P = 0.0001 |
| Mixed cellularity | 847 |  |
| Nodular sclerosis | 509 |  |
|  | p = 0.005 |  |

In patients with stage II or IV disease, the median serum CD8 levels were significantly higher than in those with stage I or II disease: 675 vs. 477 U/ml, p=0.003. It was also higher in children with B symptoms compared to all others: 622 vs. 494 U/ml, p=0.005. Cases of mixed cellularity had significantly higher median levels of the antigen than did those of nodular sclerosis: 847 vs. 509 U/ml, p=0.005.

Similarly, the median IL2R level was significantly higher in patients with stage III or IV disease than in those with lower stages: 3195 vs. 1098 U/ml, p=0.0001. The median IL2R level for children with B symptoms was 3262 U/ml, compared with 999 U/ml for those lacking constitutional symptoms (p=0.0001). There was, however, only a moderate correlation between serum CD8 antigen and IL2R levels (r=0.47).

Increased probability of treatment failure was significantly associated with higher serum CD8 levels (>430 U/ml) (p=0.02) and with higher serum IL2R levels ($\geq$5000 U/ml) (p=0.01). The same relationship was evident in the analysis restricted to patients with stage III or IV disease.

Stepwise Cox regression analysis was employed to investigate the prognostic significance of serum CD8 antigen level, serum IL2R level, erythrocyte sedimentation rate, stage, presence of B symptoms, histology, age, sex and race after adjusting the effect of each other. In this multivariate model, serum CD8 antigen level was found to have the most important impact on treatment outcome (p=0.002) whereas among other factors, only male sex was marginally associated with a worse prognosis (p=0.09).

11. EVALUATION OF THE ROLE OF THE SOLUBLE CD8 RECEPTOR AND IL-2 RECEPTOR IN PATIENTS WITH HUMAN IMMUNODEFICIENCY VIRUS INFECTION

We evaluated the levels of soluble CD8 and IL2R in patients with HIV infection. The levels of CD8 and IL2R were compared with each other and with levels of plasma p24 antigen, CD4+ cells, CD8+ cells, and CD4/CD8 ratios.

11.1. METHODS

11.1.1. SAMPLE SELECTION

Stored serum from patients with HIV infection was examined using either the CELLFREE®IL-2R Test Kit or CELLFREE® T8 Test Kit (T Cell Sciences, Cambridge, Mass.). 63 patients with HIV infection and 7 normal controls were studied. Patients were divided into 4 groups depending upon the manifestations of HIV infection; these groups were: 21 assymptomatic seropositive (ASSYM), 19 AIDS related complex (ARC), 13 Kaposi's sarcoma (KS) and 10 AIDS with opportunistic infection. Stored sera from 15 patients followed longitudinally over a period of 2 years were also examined.

11.1.2. HIV p24 ANTIGEN ASSAY

This assay utilized a sandwich ELISA microplate format. Highly specific rabbit polyclonal antibodies to HIV p24 core antigen were immobilized on microtiter plate wells and used to capture HIV p24 core antigen present in 450 µl of plasma. The captured HIV p24 core antigen was complexed with biotinylated polyclonal antibodies to HIV p24 core antigen and probed with a streptavidin-horseradish peroxidase conjugate. This complex was visualized by incubation with ortho-phenyldiamine-HCl producing a color intensity directly proportional to the amount of HIV p24 core antigen captured. The results were also quantitated spectrophotometrically and compared against the absorbance of an HIV p24 core antigen standard curve.

11.1.3. CD4/CD8 RATIO

The CD4 and CD8 ratios were determined by standard flow cytometry.

11.2. RESULTS

Soluble CD8, soluble IL2R, p24 antigen, CD4/CD8 ratio, CD4+ cells and CD8+ cells were measured in samples from patients with AIDS, ARC, KS, ASSYM or normals, as shown in Table XXIII.

TABLE XXIII

| Measurement of Shed Receptors in Patients with Different Manifestations of AIDS* | | | | | | |
|---|---|---|---|---|---|---|
| Patient Group | Soluble CD8 | Soluble IL2R | p24 | CD4/CD8 | % CD4 | % CD8 |
| ASSYM | 1029 ± 89 | 783 ± 98 | 16.4 ± 9.0 | 0.73 ± 0.08 | 27.9 ± 2.9 | 50.2 ± 3.1 |

TABLE XXIII-continued

Measurement of Shed Receptors in Patients with Different Manifestations of AIDS*

| Patient Group | Soluble CD8 | Soluble IL2R | p24 | CD4/CD8 | % CD4 | % CD8 |
|---|---|---|---|---|---|---|
| KS | 1165 ± 131 | 970 ± 129 | 8.9 ± 2.3 | 0.59 ± 0.12 | 14.7 ± 1.6 | 50.0 ± 6.4 |
| ARC | 980 ± 118 | 1011 ± 119 | 9.7 ± 3.5 | 0.71 ± 0.11 | 28.3 ± 3.6 | 47.6 ± 2.9 |
| AIDS | 717 ± 115 | 1566 ± 157 | 19.7 ± 8.1 | 0.19 ± 0.05 | 9.9 ± 2.3 | 50.2 ± 3.4 |
| Normals | 508 ± 40 | 188 ± 28 | | | | |

*Expressed as mean ± standard mean; soluble CD8 and soluble IL2R expressed as units/ml; p24 expressed as pg/ml Using chi-square analysis, comparing each group with normal controls, the majority of patients with AIDS, ARC, ASSYM and KS showed levels of both IL2R and soluble CD8 which were greater than the upper 95% value of normal ($p < 0.00001$). IL2R was better than CD4 /CDS, %CD4, and p24 for discriminating ASSYM from AIDS ($p < 0.0001$), ASSYM from ARC ($p < 0.002$) and ARC from AIDS ($p < 0.0001$). Of interest is the observed difference in soluble CD8 between groups with ASSYM, KS and AIDS. This suggests that early on in the course of HIV infection, elevated soluble CD8 levels may reflect host immune response to HIV. It has been demonstrated that CD8 positive cells are able to control HIV infection in vitro by suppressing viral replication (Walker, C. M. et al., 1986, Science, 234, 1563–1566). Soluble CD8 levels may be an accurate measure of the immune system's attempts to suppress HIV infection. In addition, by using a combination of both soluble IL2R and soluble CD8 levels in each patient group, it was possible to distinguish between normal and assymptomatic patients.

In addition to determining the value of each soluble marker level, a comparison was also made between different soluble marker values to determine how they correlated with one another. The data presented in Table XXIV presents the correlation observed between several marker combinations. The samples analyzed for this table do not represent longitudinal samples obtained from individual patients, but samples from the population of people belonging to the different HIV-infected groups.

TABLE XXIV

CORRELATIONS BETWEEN THE BEHAVIOR OF DIFFERENT PARAMETERS IN AIDS PATIENTS*

| Correlation | ASSYM | ARC | KS | AIDS | Combined HIV Positive |
|---|---|---|---|---|---|
| sCD8 v sIL-2R | | | + | | + |
| sCD8 v CD4/CD8 | | − | | − | + − |
| sCD8 v % CD4 | | − | | | |
| sCD8 v % CD8 | + | | | | + |
| p24 v s IL2R | | + | | | + |
| sIL2R v CD4/CD8 | | | | − | − |
| sIL2R v % CD4 | | − | | | − |
| sIL2R v % CD8 | | | + | | |
| CD4/CD8 v % CD4 | + | + | + | + | + |
| CD4/CD8 v % CD8 | | − | − | − | − |
| % CD4 v % CD8 | − | − | | | − |

*Pearson Correlation is expressed as + (positive correlation between the two parameters) or − (negative correlation between the two parameters); blank values indicate that the correlation had a probability index > 0.05; s = soluble It is clear that the occurrence of soluble markers is not independent of one another or of other markers of the immune system. Thus, the combined behavior of these receptors should be even more valuable than the observance of any single receptor.

Figure 11A:
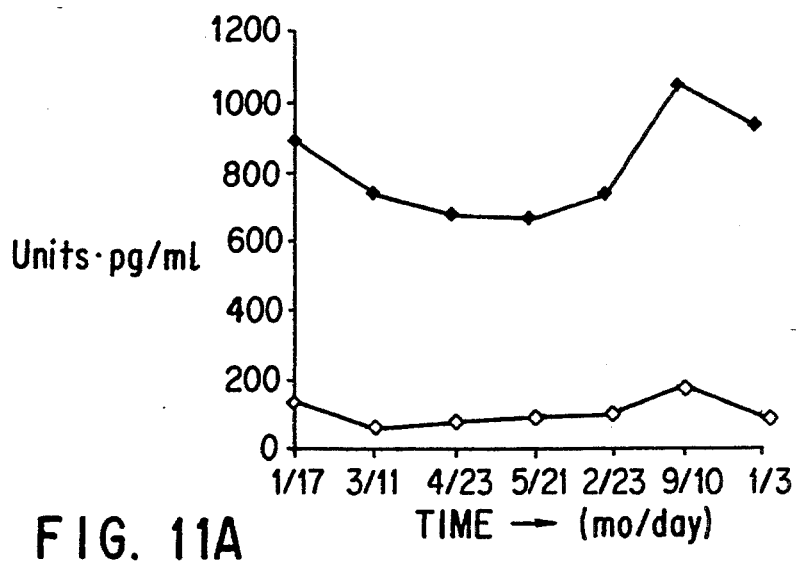
FIG. 11. Longitudinal studies of soluble CD8 levels in sera of patients with Kaposi's sarcoma (KS), shown in FIGS. 11A and 11B, or with AIDS-related complex (ARC), shown in FIG. 11C. Closed diamonds: soluble CD8 levels (U/ml); Open diamonds: HIV p24 levels (pg/ml)×10.
Figure 11B:
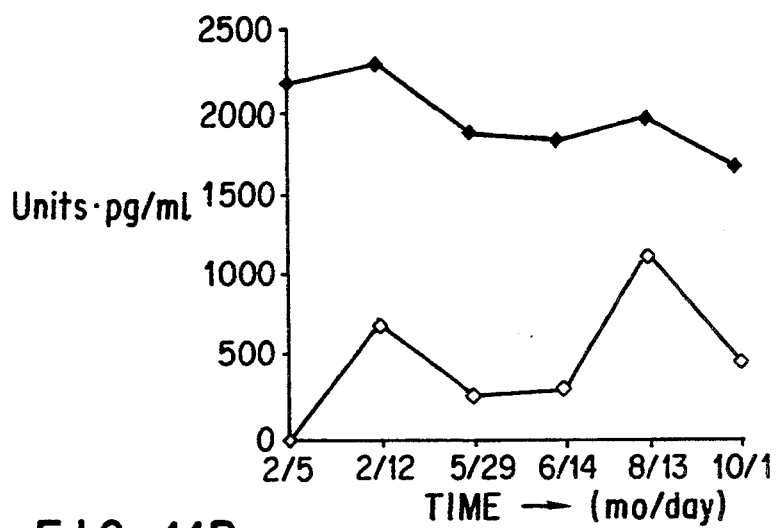
Figure 11C:
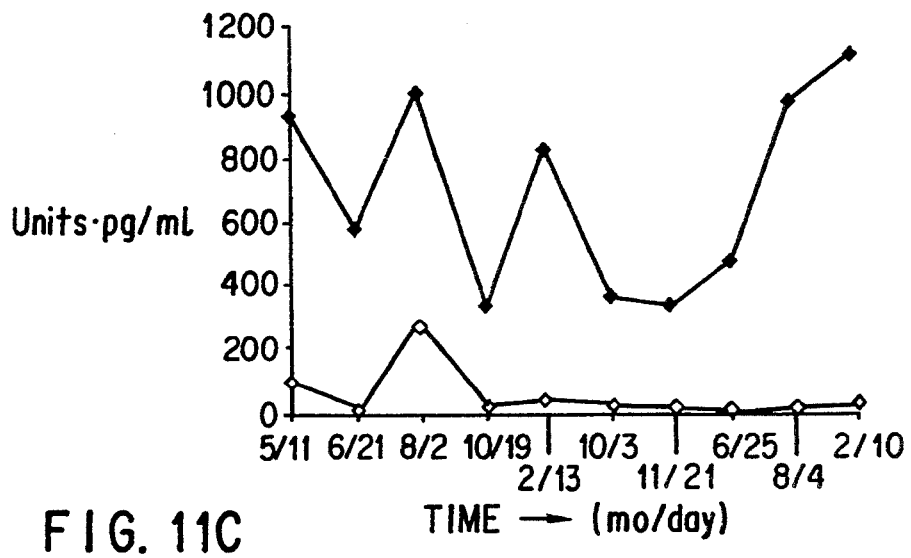

In addition to the patient samples analyzed above, one patient with ARC and two with KS were followed longitudinally as shown respectively in FIGS. 11C and 11A–11B. The results of this study indicated that soluble CD8 levels appeared to parallel the change in p24 core antigen levels. Since the p24 core antigen levels have not proved to be sensitive enough tests of the progression of AIDS, we propose that the soluble CD8 levels, which reflect the status of the immune system itself, can be a much better indicator.

12. MOLECULAR CHARACTERIZATION OF THE SOLUBLE CD8 ANTIGEN

Jurkat cell supernatants and cell lysates were immunoprecipitated with anti-CD8 mAbs, in order to study the molecular nature of the CD8 antigen in its soluble and cell-associated forms that is recognized by the antibodies.

12.1. METHODS $5 \times 10^6$ Jurkat cells in a Falcon T25 flask were pulse-labeled with 2 mCi $^{35}$S-methionine in met− RPMI 1640 medium. After six hours, the media was removed, cells were washed with the complete RPMI 1640 media, and cells were incubated in complete RPMI 1640 media for 16 hours before harvesting. Cells were pelleted by centrifugation. Supernatant samples were prepared by centrifuging cell culture supernatant at $20,000 \times g$ for 30 minutes, and filtering the supernatant through a 0.22 $\mu$m Millipore ™ filter. Cell lysates were prepared by resuspending $5 \times 10^6$ cells in 1 ml lysis buffer: 0.15M NaCl, 25 mM Tris-Cl (pH 8.0), 1 mM MgCl$_2$, 1% Nonidet P-40 (NP-40, polyoxyethylene (9) p-tert-octylphenol), 1 mM phenylmethylsulfonylfluoride (PMSF), 0.2 mg/ml alpha-2-macroglobulin, 10 mM iodoacetamide, 0.1 mg/ml ovomucoid trypsin inhibitor. Cells plus lysis buffer were allowed to stand for 0.5 hour at 4° C., centrifuged at $20,000 \times g$ for 30 minutes, and the supernatant (cell lysate sample) removed for immunoprecipitation.

Culture supernatants and cell lysates were purified by immunoprecipitating with anti-CD8 mAbs 5F4, 4C9, and OKT8. The immunoprecipitation was accomplished in two steps: a nonspecific adsorption step, and a specific binding step. To remove non-specifically bound material, the lysate or cell supernatant sample was incubated with 5% volume of packed Sepharose coupled to mouse immunoglobulin G (Affigel, Biorad, Richmond, Calif.) for 3 hours on a rocker at room temperature. After spinning out the Sepharose, the supernatant (either 1 ml culture supernatant sample or 0.2 ml lysate sample) was incubated with 10 $\mu$l packed Sepharose coupled to either mAb OKT8 or 4C9 or 5F4, or control mAb OKT3. Samples were agitated at room temperature for two hours, and then washed ten times with 1.5 ml phosphate-buffered saline. Samples were eluted into 200 $\mu$l 50 mM diethylamine, 0.15M NaCl, pH 11.0. The eluate was diluted with an equal volume of electrophoresis sample buffer. One-half of each eluate was then reduced by addition of dithiothreitol (DTT) to a concentration of 10 mM; one-half of each eluate was left unreduced. Samples were boiled and loaded onto a 10–20% sodium dodecyl sulfate-polyacrylamide gel. Gels were dried and exposed for autoradiography.

12.2. ANTI-CD8 MABS RECOGNIZE A SOLUBLE CD8 ANTIGEN OF 52-55 KILODALTONS

The nonreduced cell lysate immunoprecipitates contained predominantly a 52–55 kd form. This is somewhat smaller than the 66 kd cell surface form of the CD8 antigen previously reported (Fujimoto, J., et al., 1983, J. Exp. Med. 159:752–766). Surprisingly, the nonreduced cell culture supernatant immunoprecipitate contained only the 52–55 kd dimeric form of the CD8 antigen. This is in contrast to the results of Fujimoto et al., who detected only a 27 kd monomer form under either reducing or nonreducing conditions, of the soluble CD8 antigen in sandwich immunoassays (Fujimoto et al., supra). In the reduced supernatant immunoprecipitate described herein, the 27 kd CD8 monomer was observed, confirming the identity of the 52–55 kd soluble form as a dimer consisting of monomers each having a molecular weight of 27 kd as determined by SDS polyacrylamide gel electrophoresis. Thus, the anti-CD8 mAbs recognized a dimeric 52–55 kd form of the CD8 antigen as both a soluble and a cell-associated molecule.

When a reducing agent, DTT, was included in a sandwich enzyme immunoassay for CD8 antigen in supernatant samples, no binding was observed. Thus, reduction of the soluble dimeric form to monomer abolished the ability of the anti-CD8 mAbs to bind the soluble antigen, confirming that these anti-CD8 mAbs may bind only to a soluble CD8 dimer.

13. TOTAL CD8 ANTIGEN AND ASSAY

13.1. MATERIALS AND METHODS

Patient samples included 19 sero-positive HIV-infected individuals and 6 healthy adult volunteers. Whole blood samples were prepared as described in Section 7, supra.

13.2. TOTAL CD8 ASSAY

Total CD8 was measured in the detergent treated whole blood samples using the commercially available CELLFREE® CD8 assay kit (T Cell Sciences, Inc. Cambridge, Mass., Section 8, supra) using a one-step, three hour format. Briefly, each well of a 96 well microtiter plate was coated with 100 μl of the murine anti-CD8 coating antibody in phosphate-buffered saline overnight at 4° C. The coating buffer was removed and 300 μl of blocking buffer (0.5% casein, 0.008% NP-40, 0,005% EDTA in PBS) was added per well and incubated for 2 hours at 37° C. After washing the wells three times with 400 μl of wash buffer (PBS, pH 7.4, with 0.05% Tween 20), 50 μl of horseradish peroxidase (HRP) conjugated murine monoclonal anti-human CD8 antibody (10% FCS, 0.025% thimerosal, 0.01% gentamicin, 0.05% tween in Tris Buffered Saline, TBS) was added to all wells except those used as blanks. Ten μl of CD8 standard or whole blood lysate was added to 50 μl of sample diluent (1% bovine serum albumin, phosphate buffered saline, 0.25% NP-40 and 0.01% thimerosal) and 50 μl of this was added to the appropriate microtiter wells. The plate was covered with plate sealer and incubated for three hours at 20° C. shaking the plate at 150 rpms. After washing the plate as described above, 100 μl of OPD substrate was added to all the wells and incubated at 20° C. for 30 minutes. 50 μl of 2 N $H_2SO_4$ was added to all wells to stop the reaction and absorbance was read at 490 nm. A standard curve was constructed plotting O.D. against the concentration of the standards. The concentration of total CD8 in the whole blood samples was then determined from the standard curve. Correlation coefficients were calculated using linear regression analysis.

Whole blood samples from HIV-infected patients were assayed for absolute CD8 + T-cells/$mm^3$ using the formula: Abs. CD8+ T-cells/$mm^3$=WBC×% lymphocyte×% CD8+ T cells WBC (white blood cell count) was determined using a hemacytometer. % Lymphocyte was determined by a differential count, and %CD8+ T-cells were determined using the Ortho cytoflurograph II and Leu-2a⁻ (anti-CD[8]) fluorescein conjugated antibody (Becton Dickinson, Mountain View, Calif.)

13.3. RESULTS

Table XXV demonstrates CD8 levels (u/ml) obtained from whole blood lysates of five healthy volunteers. Since the percentage of CD8+ cells in the whole blood was not determined, O.D. values were analyzed against the total number of lymphocytes per $mm^3$ whole blood (total WBC×% lymphocytes). This value provides a reliable reflection of the absolute CD8+cells per $mm^3$ as seen in the equation in Section 13.2 supra. CD8 levels of four of the five samples correlated with total lymphocyte number (samples 1,2,3, and 5).

TABLE XXV

TOTAL CD8 ASSAY ON DETERGENT SOLUBILIZED WHOLE BLOOD FROM HEALTHY VOLUNTEERS

| Sample # | Total Lymphocytes* (Cells/μl blood) | CD8 (u/ml) |
|---|---|---|
| 1 | 2192 | 1098 |
| 2 | 2493 | 1301 |
| 3 | 2165 | 821 |
| 4 | 2282 | 1594 |
| 5 | 2747 | 1609 |

*Determined by total WBC x % lymphocyte

Figure 12:
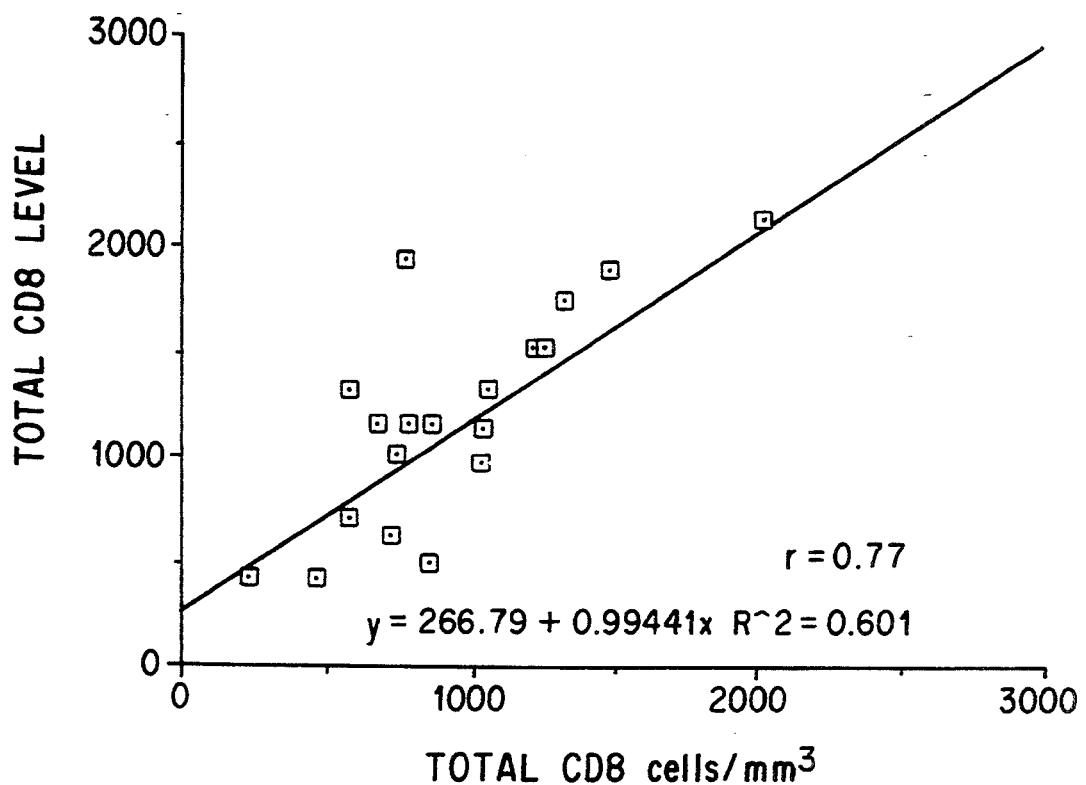
FIG. 12. Total CD8 assay on whole blood lysates of 19 HIV-infected sero-positive individuals.

Total CD8 values were also obtained from whole blood lysates of 19 HIV-infected, sero-positive individuals and compared to the total number of CD8+ T-cells/$mm^3$ of whole blood. FIG. 12 demonstrates a statistically significant correlation between total CD8 measured in the assay and the total number of CD8+ cells (r=0.77).

As described herein, we have developed a method that measures the level of total CD8 in a patient sample. Whole blood samples were detergent solubilized and assayed using a CD8 Assay Kit in a one-step, three hour format. Total CD8 values obtained in the ELISA correlated with total lymphocyte number, a reflection of total CD8+ T-cell number, in the whole blood of four out of five normal donors. In addition, a comparison between the total CD8 obtained in the CD8 ELISA and the total number of CD8+ T-cells/$mm^3$ of whole blood yielded a statistically significant correlation in HIV-infected individuals (r=0.77). As with the Total CD4 assay described in Section 7, supra, detergent solubilized whole blood samples can be used in the total CD8 assay to accurately determine the number of CD8+ T cells in whole blood. The total CD8 assay alone, or in combination with other soluble or total marker assays, can be used to monitor the immune profile of patients.

14. TOTAL TCAR ELISA

An assay to detect total T cell antigen receptor (TCAR) β chain or total Vβ5 specific TCAR chain was performed using detergent solubilized whole blood samples in a Total TCAR ELISA assay. Briefly, wells in a 96 well plate were coated with 5 ug/ml of coating antibodies which consisted of either a negative control antibody (δTCS-1 which is specific for the 82 region of the γδ T cell receptor), W76 which recognizes the constant region of the β chain (cβ), or a Vβ5 specific monoclonal antibody such as W112 (Tian et al., 1989, FASEB J. 3:A486 Abstr.) A horseradish peroxidase conjugated (HRP)-βF1 antibody which recognizes a different epitope of the β chain constant region (Cβ) than W76 was used as the detection antibody. Whole blood lysates were prepared as described in Section 7, supra. The assay format was similar to that described in U.S. Pat. No. 4,845,026, issued Jul. 4, 1989 and entitled "Assay Systems for Detecting Cell-Free T Cell Antigen Receptor Related Molecules and Clinical Utilities of the Assays." In addition, a one-step, three hour format as described in Section 13, supra, was performed with similar results. 25 ul of whole blood lysate was diluted in 75 ul of sample diluent for a starting dilution of 1:4. O.D. values from the negative control wells were subtracted from all values obtained (negative control wells using δ TCS-1 as the coating antibody averaged 0.10 and blank wells which had no antibody averaged 0.095).

Figure 13:
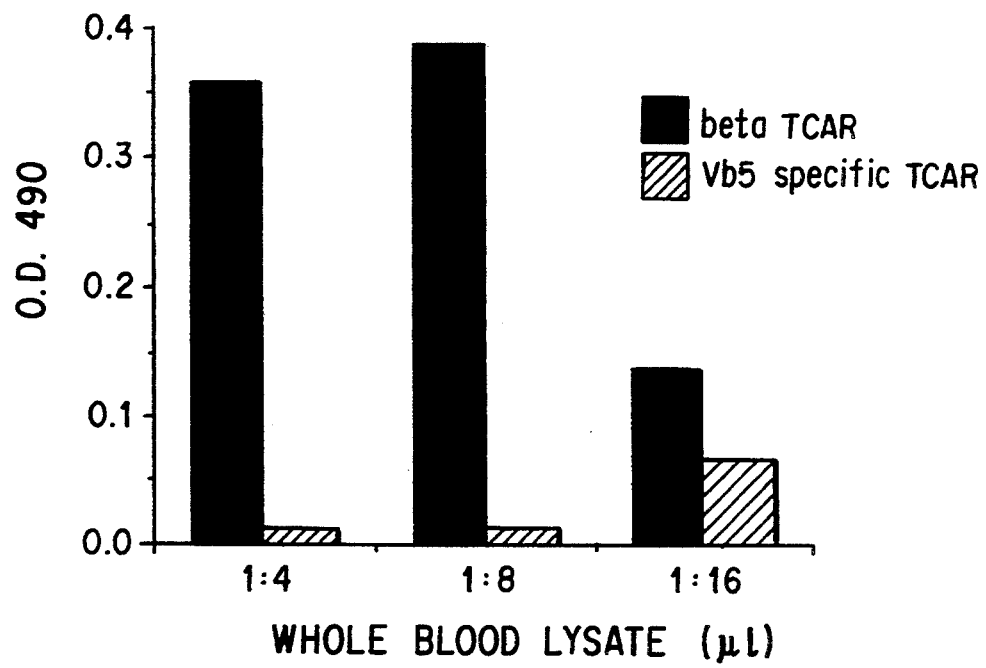
FIG. 13. Total T cell antigen receptor assay on the whole blood lysate of a normal healthy donor.

The results of the total TCAR assay can be seen in FIG. 13. TCAR β chain was optimally detected at dilutions of 1:4 and 1:8. Vβ5 specific TCAR was detected at low levels at 1:16 as well. Lower levels of Vβ5 were expected, since the Vβ5 positive subset of cells represents only a small portion of all β TCAR positive T cells. The assay demonstrated good specificity as the background O.D. was no higher when the control antibody TCS-1 was used as the coating antibody as compared to O.D.'s obtained from blank wells which contain no coating antibody (0.100 and 0.095 respectively).

This data demonstrates that whole blood lysates can be used in a TCAR ELISA to detect the total amount of TCAR β chain in a whole blood sample by using two monoclonal antibodies which recognize different regions of the constant region of the β chain. The total amount of β chain is an indication of the total amount of αβ positive T cells in the sample. Furthermore, specific subsets such as the Vβ5 family which represent only 1–5% of the total TCAR β chains in normal blood can be detected. Detection of the total amount of such subsets will be useful in correlating specific V region expression to disease state or treatment outcome. The success of this assay for measuring total β or Vβ amounts should easily extend to total Vα amounts, or to total γδ or to total Vγ, Vδ and related subset assay procedures as well.

15. SOLUBLE CD2 DETECTION

The supernatants of various cultured cells were assayed for soluble CD2 using two monoclonal antibodies which define different epitopes of the CD2 (T11) molecule. Samples were assayed using a sandwich immunoassay format as previously described, in which monoclonal antibodies B67.6.1.1. and B67.1.1.1. (Perussia, B., et al., 1983, J. Immunol. 130:2142) were used as the capture and detection antibodies, respectively, and vice versa.

A released form of CD2 was detected in supernatants of the following cultured cells which are CD2 surface positive: HPB-ALL, Jurkat, CEM and MOLT-4. By contrast, soluble CD2 was not detected in the supernatants of cultured cells which are CD2 surface negative such as DAUDI. Soluble CD2 was also not detected in the supernatant of cultured PEER cells, a T cell line which is weakly CD2 surface positive.

16. SOLUBLE CD35 ANTIGEN AND DETECTION IN PATIENTS

A number of disease and disorders involve complement. Measurement of soluble CD35 in these situations can be important for monitoring the effectiveness of treatment regimens, detecting a particular disorder or diagnosing a specific disease state. Some relevant complement-mediated diseases and disorders include but are not limited to inflammation, autoimmune diseases involving circulating immune complexes such as systemic lupus erythematosis (SLE) and rheumatoid arthritis, AIDS, hemodialysis, transplantation, blood transfusion, cardiopulmonary bypass, thermal injury (burn), adult respiratory distress syndrome, sepsis, and barotrauma (section 2.3, supra).

Measurements of soluble CD35 levels in patients would provide a good indicator for predicting disease progression. Furthermore, therapy of diseases and disorders amenable to treatment with soluble CD35 may be followed by measurement of soluble CD35 levels in patients. In addition to the complement-mediated diseases and treatments discussed above, it has been demonstrated that a recombinantly produced soluble complement receptor type 1 (sCD35) functions as an in vivo inhibitor of complement and acts to suppress post-ischemic myocardial inflammation and necrosis (Weisman et al., 1990, Science 340:146–151). The soluble levels of sCD35 can be measured in the sCD35 assay to determine pharmacokinetics and effectiveness of different treatment regimes. Thus, the soluble CD35 assay can detect both spontaneously released CD35 and recombinant soluble CD35 and aid in monitoring treatment regimens.

16.1. MATERIALS AND METHODS

Production of Polyclonal Rabbit anti-CD35

Two rabbits (#30 and #31) were subcutaneously injected with 250 μg of CD35 in 0.5 ml of CFA (Complete Freunds's adjuvant) followed by five intramuscular injections of CD35. The first intramuscular injection of 250 μg of CD35 in 0.5 ml of IFA (Incomplete Freund's adjuvant) was given two weeks after the initial subcutaneous injection. Four weeks later (on week 6) 125 μg of CD35 in 0.5 ml IFA was given, followed by three more identical intramuscular injections six weeks apart. At 26 weeks the rabbits were exsanguinated. One prebleed of 10 ml, one test bleed of 5 ml on week 4, and six production bleeds of 40 ml each (weeks 8, 10, 14, 16, 20, 22) were also collected during the immunization schedule and assayed for anti-CD35 antibody production by ELISA. Briefly, a 96 well plate was coated with each rabbit serum at 1:1000 followed by several serial dilutions in PBS. After blocking and washing the plates, purified sCR1 or PBS alone was added. This step was followed by the addition of HRP-conjugated YZ1 monoclonal antibody (section 16.3.2, infra). The plate was developed with OPD substrate and absorbance read at 490 nm.

Polyclonal antibodies that are produced from multiple bleeding of different rabbits can be tested to ensure CD35 reactivity of sufficient titer. Antibodies which yield an assay sensitivity of about 0.5 ng/ml are preferred for use.

Purification of Rabbit Polyclonal anti-CD35 Serum.

The rabbit polyclonal anti-CD35 serum was purified as follows. 10 ml of frozen rabbit serum was thawed. At 4° C., 10 ml of saturated $(NH_4)_2SO_4$ (76.1 g in 100 ml distilled $H_2O$) was added dropwise to the serum. After 2 hours at 4° C. the serum was spun at 3,000× g for 30 min at 4° C. The supernatant was discarded and the pellet resuspended in 5 ml of PBS. The resuspended pellet was then dialyzed in Spectrapor #2 membrane (12,000–14000 molecular weight cutoff) in 4 L of PBS overnight, changing the PBS one time.

To remove any salts still present after dialysis, a Sephadex G-25 column with a 30 ml bed volume was assembled and equilibrated with PBS. The dialyzed sample was applied to the column and washed with PBS. Fifteen 3 ml fractions were collected and samples read at O.D. 280. Samples with an O.D." 0.7 were pooled and subsequently run over an affi-gel column coupled to CD35.

The CD35 conjugated affinity column was prepared as follows. Three ml of Affi-Gel resin (Affi-Gel Active Ester Agarose, Bio-Rad, Richmond, Calif.) was washed 3 times with 10 ml each of isopropanol, followed by three 10 ml washes with 4° C. distilled $H_2O$. Five ml of sCD35 (11.5 mg) was added to the washed resin and incubated overnight at 4° C. 0.1 ml of 1M ethanolamine pH 7.0 was added to block residual active sites and incubated for one hour at 4° C. The coupled resin was then packed in a Bio-Rad Econo-column and allowed to settle. The resin was then washed twice with 5 ml of 0.1M hepes, pH 8.0, once with 5 ml of 20 mM $NaH_2PO_4$ with 0.7M NaCl, pH 12.0, and once with 20 ml of 0.1M HEPES +0.15M NaCl pH 7.4. The column was stored until use at 4° C. in 0.1M HEPES +0.15M NaCl pH 7.4+0.1% $NaN_3$.

After washing the CD35 coupled Affi-Gel column with elution buffer (0.7M NaCl, 20 mM $Na_2HPO_4$, pH 12 with 10N NaOH) and reequilibrating with PBS, the pooled fractions from the G-25 column were added to the washed gel and incubated on a rocker overnight at 4° C. The column was repacked and washed with 10× bed volumes with PBS (bed volume was 3 ml). The column was then eluted with 10× the bed volume with elution buffer, collecting 0.5 ml fractions for 30 tubes. The fractions collected were read at O.D. 280. Peaks were pooled separately, and dialyzed overnight in PBS at 4° C. Antibody concentration was then determined from the dialyzed fractions by the following formula:

$$\frac{(O.D. 280)}{1.4} = \text{concentration of antibody (mg/ml)}$$

The purified polyclonal rabbit anti-CD35 was then frozen in aliquots at −70° C. until needed.

Horse Radish Peroxidase Conjugation of anti-CD35 Antisera

The affinity purified polyclonal anti-CD35 (e.g. from rabbit #31) was concentrated by placing the antibody in dialysis tubing with a molecular weight cutoff of 12–14,000 (Spectrapor). This was then buried in PEG 8,000 and the volume in the tubing allowed to reduce. The tubing was then washed clean of PEG 8,000 and dialyzed against 50 mM $NaCO_3$ in distilled $H_2O$ (Baker Analytical), pH 9.5, overnight at 4° C.

10 mg of the HRP (horse radish peroxidase, Boehring-Manheim) was reconstituted in 1 ml of 1 mM Na Acetate (equal volumes of 1 mM Sodium Acetate and 1 mM Acetic Acid, pH to 4.4 with Acetic Acid), sheltering the HRP from light. 0.6 ml of reconstituted HRP was added to 0.4 ml of the 1 mM Na Acetate for a final concentration of 6 mg/ml of HRP. 21.4 mg of Na Periodate was dissolved in 1 ml of the 1 mM Na Acetate buffer and 0.2 ml of this solution was added to the 1 ml of the HRP solution. After incubating for 20 minutes at 20° C. on a rocker platform, the Na Periodate/HRP solution was dialyzed against Na Acetate Buffer overnight at 4° C. in the dark.

After determining the concentration of the antibody to be conjugated according to the above equation, the dialyzed HRP was added to the antibody at a ratio of 1:2 (mg of HRP:mg of Antibody) and allowed to incubate on a rocker platform for two hours at 20° C., sheltered from the light.

10 mg of sodium borohydride (Sigma) in distilled $H_2O$ was prepared just before use and 11 μl added for every ml of antibody-HRP solution. After incubating on ice for one hour, the mixture was dialyzed against PBS overnight at 4° C. in the dark. After dialyzing, 10% Thimerosol (Bio-Rad) solution was added for a final concentration of 0.01%. Heat-inactivated Fetal Bovine Serum (30 minutes at 57° C., Irving Scientific) was then added for a final concentration of 10%. The mixture was then spun at 5,000 xg for 10 minutes to remove aggregated antibody, aliquoted, and stored at 4° C. away from light.

Production and Purification of soluble CD35.

Recombinant soluble human CD35 was produced and purified according to the methods previously outlined in detail (Intl. Patent App;. #PCT#US8989#01358 published Oct. 5, 1989 as WO89/09220 and entitled "The Human C3b/C4b Receptor (CD35)" and H. F. Weisman, et al., Science Vol. 340, Jul. 13, 1990). Purified soluble human CD35 was used for the rabbit immunizations.

Soluble CD35 Bead Assay Protocol

One soluble CD35 Assay is a solid-phase (bead) sandwich immunoassay employing polyclonal capture and detection antibodies, with the detection antibody being Horse Radish Peroxidase (HRP) conjugated. The assay is carried out according to the following protocol.

50 μl of standard, control or serum specimen in duplicate was pipetted into designated 12×75 mm polystyrene tubes. The standards contained recombinant human CD35 in a buffered solution containing bovine serum and thimerosol at the following concentrations: 0, 5, 10, 20, 40, 60, and 80 ng/ml. 150 μl of the HRP conjugated rabbit polyclonal anti-human CD35 antibody was added to each test tube. Using non-metallic forceps, one rabbit polyclonal anti-human CD35 coated bead was then added to each tube. After shaking the tubes to ensure proper mixing of all reagents, they were incubated for 120 minutes at room temperature (22°–26° C.) on a rotator set at 150 rpm. At the end of the incubation, the beads were washed three times with 2 ml of deionized water. Just prior to use the chromogen solution was prepared by dissolving one chromogen tablet (containing O-Phenylenediamine +5.3 mM/L urea peroxide +thimerosol) per 5 ml of substrate diluent. 200 μl of the chromogen solution was pipetted into each tube and into two empty test tubes to be used as substrate blanks. After incubating the tubes for 30 minutes at room temperature (22°-26° C.) without shaking, 1.0 ml of the stop solution was added to each tube as well as the two blank chromogen tubes. The stop solution consisted of 1N sulfuric Acid, reagent grade, in deionized water. All tubes were then read on a spectrophotometer at 492 nm after adjusting absorbance to 0 using the chromogen solution blank tubes.

A standard curve was constructed by plotting mean absorbance on the vertical (Y) axis versus the corresponding CD35 concentration on the horizontal (X) axis, using rectilinear graph paper. An example of the standard curve is demonstrated in FIG. 14. Mean absorbance values of the specimen samples could then be determined from the standard curve.

Soluble Human CD35 Plate Assay

The development of another soluble CD35 Assay was initiated with monoclonal capture and detection antibodies utilizing a two-step solid phase (plate), enzyme immunometric assay. The evaluation of polyclonal antibodies used in combination with other polyclonal antibodies or monoclonal antibodies was evaluated in this plate assay according to the following procedure.

100 μl of monoclonal antibody J3D3 at 0.4 μg/ml in PBS or for example, purified Rabbit serum #30 at 1.0 μg/ml in PBS was added to each well of an Immulon II plate (Dynatech) for 24 hours at 4° C. The J3D3 antibody was obtained from AMAC, Inc., Westbrook, Me. (Cook, J., et al., 1985, Mol. Immunol. 22:531). The coating antibody was then discarded from each of the wells and 300 μl of blocking buffer added for 2 hours at 37° C. After washing three times in washing buffer, 100 μl of primary calibrators I and II (p.c.I and p.c. II) were added to the appropriate wells. Primary calibrators were comprised of recombinant soluble human CD35 diluted to 120 ng/ml and 80 ng/ml, respectively, in standard diluent. The starting concentrations of p.c.I and p.c. II were then diluted to 120, 100, 80, 40, and 20 ng/ml, and 80, 40, and 20 ng/ml respectively. After incubating for two hours at 37° C., the plates were washed three times with washing buffer and 100 ul of either a 1:5000 dilution of polyclonal anti-human CD35 (rabbit serum #31)-HRP conjugated or a 1:4000 dilution of monoclonal anti-human CD35 (YZ1)-HRP conjugated was added to the appropriate wells for 2 hours at 37° C. Five minutes before washing the wells, the chromogen substrate was prepared by dissolving one chromogen tablet (containing O-Phenylenediamine) per 10 ml of substrate diluent. The wells were washed three times and 100 ul of substrate added to each well. After 20 minutes at room temperature, the reaction was stopped by the addition of 50 ul of 2N $H_2O_4$ per well. Absorbance was read on a Dynatech MR 600 plate reader at O.D. 490, reference at 630 nm.

16.2. RESULTS 16.2.1. POLYCLONAL CD35 ANTIBODY PREPARATIONS

Polyclonal antibodies were generated in rabbits that received recombinant soluble CD35 as immunogen. The antibodies were subsequently purified using recombinant CD35 solid phase chromatography (Section 16.2, supra). The resulting polyclonal antibodies were specific to CD35, recognized multiple CD35 antigenic determinants, and were functional as evidence by their ability to bind to the CD35 column. The specificity of the CD35 column was enhanced due to the attachment of a single defined CD35 molecule to the column matrix. CD35 purified from erythrocyte membranes is still significantly less pure than the recombinantly produced form. The use of CD35 column purified polyclonal antibody is a substantial improvement over using total IgG polysera, as the percentage of CD35 specific antibodies relative to protein concentrations is much higher.

16.2.2. ASSAY CHARACTERISTICS

One soluble CD35 assay is a 1 step solid-phase sandwich immunoassay. The capture antibody is coated on a solid support such as a bead and then simultaneously incubated with the sample (or standard) and the conjugated detection antibody to form an antibody-antigen-antibody sandwich. Following the 1 step incubation, unbound reagents are washed away and the amount of sandwich is quantitated by the development of a color reaction. Both capture and detection antibodies are polyclonal antibodies.

The Characteristics of the assay are given in Table XXVI.

TABLE XXVI

CHARACTERISTICS OF A POLYCLONAL ANTIBODY BASED SOLUBLE CD35 ASSAY

*fully weighted mean intraassay CV of 4.0%
*mean inter-assay CV of 6.4%
*minimum detectable concentration (MDC) observed range of 0.35–0.62 ng/ml mean value of 0.47 ng/ml
*measuring range upper limit of 80 ng/ml
*dilution linearity for samples up to 2000 ng/ml
*CV of the slope of the standard curve for 65 assays performed was 3.7%

The development of a soluble CD35 assay was initiated with monoclonal capture and detection antibodies. Basic assay calibrators developed for this purpose ranged from 0–120 ng/ml of CD35. Monoclonal antibodies that were analyzed included YZ-1 (Changelian et al., 1985, J. Immunol. 134:1851) and J3D3 (Cook et al., 1985, Mol. Immunol.:22:531). These reagents were either tested as capture antibodies by coating them on microtiter plates during the 24 hours prior to the assay or tested as detection antibodies. In addition, two polyclonal antibody preparations (R30 and R31) were similarly analyzed and compared to the monoclonal antibody performances. Combinations of monoclonal and polyclonal antibodies in either capture or detection configurations were evaluated. Surprisingly, the configuration of polyclonal antibodies as both capture and detection antibodies provided a more sensitive assay than any other combination studied and yielded more consistent results. The results of 2 configurations are shown in Table XXVII.

TABLE XXVII

SOLUBLE CD35 ASSAY
POLYCLONAL vs. MONOCLONAL ANTIBODIES*

| CD35 | Polyclonal | | Monoclonal | |
|---|---|---|---|---|
| ng/ml | o.d. | % C.V. | o.d. | % C.V. |
| 0 | 0.006 | — | 0.008 | — |
| 20 | 0.657 | 2.7 | 0.292 | 3.6 |
| 40 | 0.902 | 3.1 | 0.580 | 6.5 |
| 80 | 1.163 | 3.6 | 1.179 | 8.3 |
| 100 | 1.226 | 3.0 | 1.417 | 4.5 |

TABLE XXVII-continued

SOLUBLE CD35 ASSAY
POLYCLONAL vs. MONOCLONAL ANTIBODIES*

| CD35 ng/ml | Polyclonal o.d. | Polyclonal % C.V. | Monoclonal o.d. | Monoclonal % C.V. |
|---|---|---|---|---|
| 120 | 1.321 | 3.5 | 1.619 | 5.3 |

*Polyclonal capture and detector antibodies versus monoclonal capture and detector antibodies in a 2-step plate assay.

We believe this unexpected result arises from two sources. Firstly, the polyclonal antibodies recognize multiple determinants on CD35 and may effectively capture or detect significantly more analyte. Secondly, we specifically selected for functional polyclonal antibodies that are specific for CD35 by purifying antisera on CD35 affinity columns. This selection probably resulted in a final product with a greater proportion of functional antibody as-compared to the overall protein concentration. Although there have been some publications of other CD35 assays (Schreiber, U.S. Pat. No. 4,672,044 issued Jun. 9, 1987; Yoon & Fearon, 1985, J. Immunol. 134, 3332; Fearon et al., International Patent Application Number PCT/US89/01358 published Oct. 5, 1989), none has achieved the level of sensitivity of the polyclonal based sandwich immunoassay. As indicated infra the polyclonal based assay has a minimum detectable CD35 concentration of about 0.5 ng/ml.

The polyclonal assay is a very reliable and reproducible assay for the measurement of soluble CD35. During optimization of the assay, it was noted that the overall binding affinity of the polyclonal CD35 specific antibodies was slightly less than the monoclonal antibodies used in other 1 step based assays. To correct for this, the primary incubation period (Capture Ab on bead +standard/specimen +conjugated antibody) was extended from 90 minutes to 2 hours.

This assured that the sandwich reaction would proceed to completion over the entire measuring range. This optimization was achieved by comparing the observed optical density changes over the range of the standard curve in fifteen (15) minute added increments.

As can be seen in Table XXVIII, the reaction began to stabilize during the 105 minute incubation period (111.3% change) and was fairly stabilized by 120 minutes (105.5% change).

Evidence that the soluble CD35 bead assay is functional was derived in a purified recombinant spike and recovery study. A normal human serum pool was initially assayed and found to contain 25.7 ng/ml of soluble CD35. Aliquots of this pool were then spiked with 500 or 250 ng/ml of CD35 and diluted with specimen diluent to three concentrations within the measuring range. The two spike specimens were diluted to different concentrations and yielded a mean recovery of 94.5% (Table XXIX).

TABLE XXVIII

SOLUBLE CD35 BEAD ASSAY INCUBATION KINETICS

| CD35 ng/ml | % Change in O.D. 105–120 min* | % Change in O.D. 120–135 min* |
|---|---|---|
| 10 | 111.7 | 105.6 |
| 20 | 116.6 | 104.4 |
| 30 | 109.4 | 106.1 |
| 50 | 107.3 | 106.8 |
| 80 |  | 104.6 |
| Mean | 111.3 | 105.5 |

*Primary incubation period (bead + standard + conjugate)

TABLE XXIX

SOLUBLE CD35 ASSAY SPIKE
AND RECOVERY FROM NORMAL HUMAN SERUM

| CD35 (ng/ml) | Dilution | Recovery Theoretical | Recovery Observed | % Recovery |
|---|---|---|---|---|
| 0 | — | — | 25.7 | — |
| 500 | 1:6.25 | 80 | 72.8 | 91.0 |
|  | 1:12.5 | 40 | 39.4 | 98.5 |
|  | 1:25.0 | 20 | 19.7 | 98.5 |
| 250 | 1:3.33 | 75 | 65.0 | 86.7 |
|  | 1:5.00 | 50 | 48.6 | 97.2 |
|  | 1:10.0 | 25 | 23.8 | 95.2 | n = 8 per dilution
Mean % Recovery:94.5%

Figure 14:
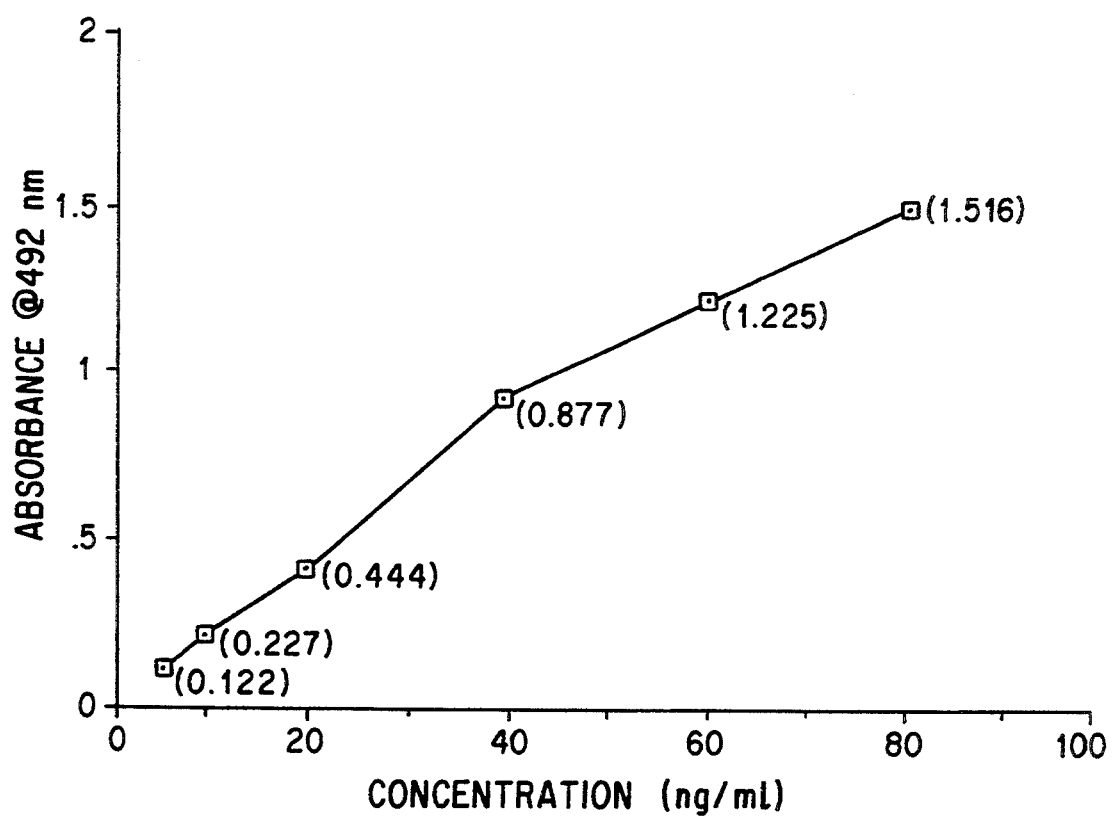
FIG. 14. Soluble CD35 assay standard curve.

The range of the assay for measuring soluble CD35 is seen from the standard curve (FIG. 14). As the assay is configured, the standard curve is generated from six standards of 5, 10, 20, 40, 60 and 80 ng/ml of CD35. The observed linear response is subjected to standard regression analysis. The results indicate a slope of approximately 1.8–1.9, an $r^2$ value of 0.997 and a Y-intercept of about zero. The standard curve evidenced excellent reproducibility with a CV of the slope of the standard curve for 65 assays performed of 3.7%. Replicate assays indicated a minimum detectable concentration of about 0.5 ng/ml as calculated by:

$$MDC = \frac{\overline{x}OD_0 + 2SD_0}{\overline{x}\,OD_{10} - \overline{x}OD_0} \times 10 \text{ ng/ml}$$

$SD_0$ = Standard deviation observed for 0 ng/ml point
$xOD_0$ = mean of the optical density at 9 ng/ml point
$xOD_{10}$ = mean of the optical density measured for 10 ng/ml The range of the MDC's observed was 0.35–0.62 ng/ml with a mean value of 0.47 ng/ml

16.2.3. DETECTION OF SOLUBLE CD35 IN PATIENT SERA

Following the development of a reliable CD35 immunoassay with greater sensitivity, various patient samples were analyzed. Normal serum values were evaluated from fifty two normal serum specimens to determine the normal serum range and mean value of soluble CD35 in serum. The normal range obtained based upon a 95% confidence interval is 22.5–65.1 ng/ml with a mean value of 44 ng/ml. Two specimens yielded values below this range and one above it. The observed range was 16.4 ng/ml to 68.3 ng/ml (FIG. 15).

Figure 15:
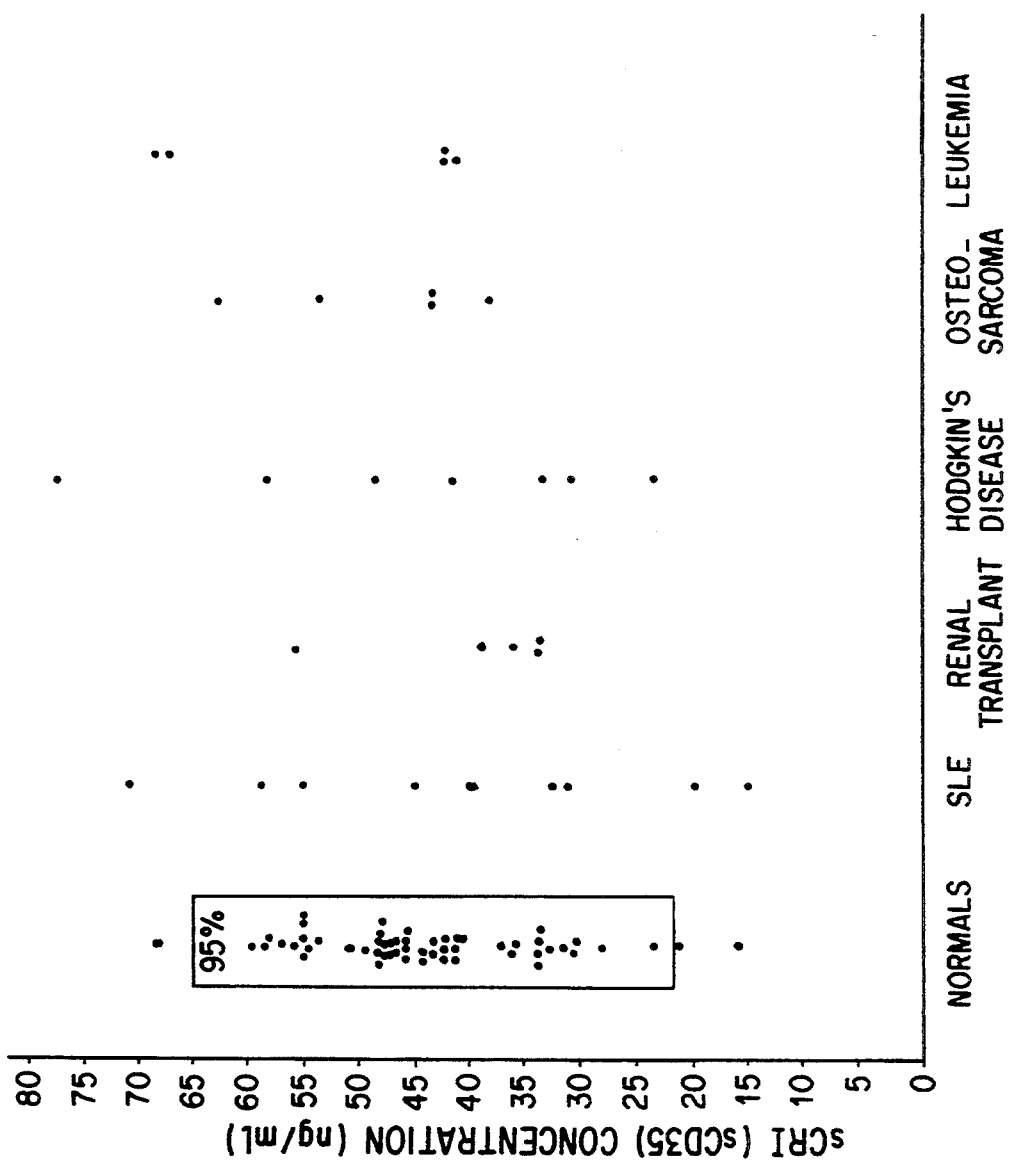
FIG. 15. Detection of soluble CD35 in normal and patient sera.

Once the normal range had been accurately determined, clinical specimen values were evaluated (FIG. 15). Serum samples from patients with systemic lupus erythematosus (SLE), renal transplants, Hodgkin's disease, osteosarcoma and unclassified leukemias were tested. Samples were tested undiluted and at a 1:3 dilution in the soluble CD35 assay. Of the thirty-one specimens evaluated, none produced values above the upper limit of the standard curve (80 ng/ml). Two of nine SLE serums evidenced a soluble CD35 level below the normal range, while one of nine yielded a value above the normal range. One of seven Hodgkin's Disease and two of five leukemia serums demonstrated levels above the normal range. These results clearly demonstrate that soluble CD35 levels can be detected in randomly selected patients with renal transplant, Hodgkin's disease, osteosarcoma, leukemia and lupus.

16.3. DISCUSSION

It has been clearly demonstrated that soluble CD35 can be detected in the sera of randomly selected patients with lupus, renal transplant, osteosarcoma, Hodgkin's disease and leukemia. Given this positive result, it is now possible to subdivide each patient population into subgroups by disease stage, type of disease, type of treatment, acute versus chronic symptoms such as the acute flareups of rheumatoid arthritis versus the more chronic longterm symptoms etc. The levels of sCD35 alone or in combination with other soluble or total markers can then be correlated with the disease state or treatment outcome.

17. DEPOSIT OF HYBRIDOMAS

The following hybridoma cell lines, producing the indicated monoclonal antibody, have been deposited with the American Type Culture Collection, Rockville, Md., and have been assigned the listed accession numbers:

| Hybridoma | Monoclonal Antibody | Accession Number |
|---|---|---|
| Cell line AM92/2R12 | AM92/2R12 (anti-IL2R) | HB 9341 |
| Cell line 7G7 | 7G7 (anti-IL2R) | HB 10242 |
| Cell line 4C9 | 4C9 (anti-CD8) | HB 9340 |
| Cell line 5F4/7B12 | 5F4/7B12 (anti-CD8) | HB 9342 |
| Cell line 8F4 | 8F4 (anti-CD4) | HB 9843 |
| Cell line R2B7 | R2B7 (anti-CD4) | HB 9842 |
| Cell line 8A3.31 | 8A3.31 ($\beta$F1) | HB 9283 |
| Cell line W4F.5B | W4F.5B (anti-C$\beta$) | HB 9282 |
| Cell line $\delta$TCS1 | $\delta$TCAR3 = $\delta$TCS1 | HB 9578 |
| Cell line W112 | W112(V$\beta$5 | HB 9927 |

The present invention is not to be limited in scope by the cell lines deposited since the deposited embodiments are intended as single illustrations of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entireties'.

What is claimed is:

1. A method for detecting or measuring soluble CD35 in a sample without the need to preconcentrate the sample comprising:
   (a) contacting the sample with a first anti-CD35 polyclonal antibody under conditions which allow immunospecific binding to occur;
   (b) contacting the sample with a second anti-CD35 polyclonal antibody under conditions which allow immunospecific binding to occur; and
   (c) detecting or measuring any immunospecific binding that occurs of a component in the sample with both the first and second polyclonal antibodies, in which immunospecific binding of a component of the sample with both the first and second polyclonal antibodies indicates the presence or amount of the soluble CD35 in the sample.

2. The method according to claim 1 in which the sample comprises a biological fluid from a patient.

3. The method according to claim 2 in which the biological fluid is selected from the group consisting of serum, plasma, saliva, urine, spinal fluid, synovial fluid, amniotic fluid and cranial fluid.

4. The method according to claim 2 in which the first and second antibodies are immunoaffinity purified prior to use by adsorption to immobilized CD35.

5. The method according to claim 2 in which soluble CD35 present in the sample in an amount as low as about 0.5 nanograms per milliliter can be detected.

6. The method according to claim 2 in which the first antibody is immobilized.

7. The method according to claim 6 in which the immobilized anti-CD35 polyclonal antibody is immobilized on a bead.

8. The method according to claim 6 in which the second antibody is labeled.

9. The method according to claim 8 in which the sample, the second antibody and a bead coated with the first antibody are added to one container at approximately the same time under conditions that allow immunospecific binding.

10. The method according to claim 2 in which the first and second antibodies are added to the sample at about the same time, and then the sample is incubated over a period of at least two hours in order to allow immunospecific binding to occur.

11. The method according to claim 1 in which the first antibody is immobilized.

12. The method according to claim 11 in which the immobilized anti-CD35 polyclonal antibody is immobilized on a bead.

13. The method according to claim 11 in which the second antibody is labeled.

14. The method according to claim 1 in which the first antibody is identical to the second antibody.

15. The method according to claim 1 in which the first and second antibodies are different.

16. The method according to claim 1 in which the first and second antibodies are rabbit antibodies.

17. The method according to claim 1 in which the soluble CD35 is spontaneously released soluble CD35.

18. The method according to claim 1 in which the soluble CD35 is recombinant soluble CD35.

* * * * *